US012807721B2

(12) United States Patent
Madden et al.

(10) Patent No.: US 12,807,721 B2
(45) Date of Patent: Nov. 24, 2026

(54) METHODS FOR THE TREATMENT OF THYROID EYE DISEASE

(71) Applicant: Horizon Therapeutics Ireland DAC, Dublin (IE)

(72) Inventors: David Madden, Mount Kisco, NY (US); Kathleen Gabriel, Voorhees, NJ (US); Guido Magni, Basel (CH); Richard Woodward, Phoenixville, PA (US)

(73) Assignee: HORIZON THERAPEUTICS IRELAND DAC, Dublin (IE)

( * ) Notice: Subject to any disclaimer, the term of this patent is extended or adjusted under 35 U.S.C. 154(b) by 416 days.

(21) Appl. No.: 18/490,687

(22) Filed: Oct. 19, 2023

(65) Prior Publication Data

US 2024/0301072 A1 Sep. 12, 2024

Related U.S. Application Data

(63) Continuation of application No. 18/182,182, filed on Mar. 10, 2023, now abandoned, which is a continuation of application No. 17/117,625, filed on Dec. 10, 2020, now abandoned, which is a continuation-in-part of application No. 16/293,293, filed on Mar. 5, 2019, now Pat. No. 11,208,490, and a continuation-in-part of application No. 16/256,221, filed on Jan. 24, 2019, now Pat. No. 11,208,489.

(60) Provisional application No. 62/946,239, filed on Dec. 10, 2019, provisional application No. 62/716,194, filed on Aug. 8, 2018, provisional application No. 62/638,689, filed on Mar. 5, 2018, provisional application No. 62/635,342, filed on Feb. 26, 2018, provisional application No. 62/621,201, filed on Jan. 24, 2018.

(51) Int. Cl.
*C07K 16/28* (2006.01)
*A61K 45/06* (2006.01)

(52) U.S. Cl.
CPC .......... *C07K 16/2863* (2013.01); *A61K 45/06* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,572,897 | B2 | 8/2009 | Graus et al. |
| 7,579,157 | B2 | 8/2009 | Graus et al. |
| 8,153,121 | B2 | 4/2012 | Smith et al. |
| 11,208,489 | B2 | 12/2021 | Madden et al. |
| 11,208,490 | B2 | 12/2021 | Madden et al. |
| 12,209,130 | B2 | 1/2025 | Madden et al. |
| 12,286,481 | B2 | 4/2025 | Madden et al. |
| 12,358,993 | B2 | 7/2025 | Madden et al. |
| 2007/0218514 | A1 | 9/2007 | Smith et al. |
| 2016/0287611 | A1 | 10/2016 | Dobak |
| 2019/0225696 | A1 | 7/2019 | Madden et al. |
| 2019/0270820 | A1 | 9/2019 | Madden et al. |
| 2021/0284741 | A1 | 9/2021 | Madden et al. |
| 2022/0324985 | A1 | 10/2022 | Madden et al. |
| 2022/0340667 | A1 | 10/2022 | Madden et al. |
| 2022/0356257 | A1 | 11/2022 | Sherman et al. |
| 2025/0051461 | A1 | 2/2025 | Madden et al. |
| 2025/0197512 | A1 | 6/2025 | Madden et al. |
| 2026/0035472 | A1 | 2/2026 | Madden et al. |

FOREIGN PATENT DOCUMENTS

| | | | |
|---|---|---|---|
| WO | WO 2016/064716 | A1 | 4/2016 |
| WO | WO 2019/173352 | A1 | 9/2019 |

OTHER PUBLICATIONS

Bagatell, R. et al., "Pharmacokinelically Guided Phase 1 Trial of the IGF-1 Receptor Antagonist RG1507 in Children with Recurrent or Refractory Solid Tumors", Clin Cancer Res., vol. 17(3), pp. 611-619 (2011).

Bahn, R. S., "Current Insights into the Pathogenesis of Graves' Ophthalmopathy", Horm Metab Res., vol. 47(10), pp. 773-778 (2015).

Bahn, R. S., "Graves' ophthalmopathy", N Engl J Med., vol. 362(8), pp. 726-738 (2010).

Bartalena, L. et al., "Consensus statement of the European Group on Graves' orbitopathy (EUGOGO) on management of GO", Eur J Endocrinol, vol. 158(3), pp. 273-285 (2008).

Bartelena, L. et al. "Efficacy and safety of three different cumulative doses of intravenous methylprednisolone for moderate to severe and active Graves' orbitopathy", J Clin Endocrinol Metab., vol. 97(12), pp. 4454-4463 (2012).

Chen, H. et al., "Teprotumumab, an IGF-1R blocking monoclonal antibody inhibits TSH and IGF-1 action in fibrocytes", J Clin Endocrinol Metab., vol. 99, pp. E1635-E1640 (2014).

Chen, X. L. et al., "Effects and Its Mechanism of IGF-1R on the Synthesis of Hyaluronic Acid in Orbital Fibroblasts of Thyroid Associated Ophthalmopathy", Sichuan Da Xue Xue Bao Yi Xue Ban, vol. 48(5), pp. 727-731 (2017).

Clinical Trials No. NCT01868997. Teprotumumab (RV 001) Treatment in Patients With Active Thyroid Eye Disease, Version 1. Reported date submitted: May 30, 2013. Date publicly available: Unknown. Date accessed: May 24, 2024. Available at https://classic.clinicaltrials.gov/ct2/history/NCT01868997?V_1=View#StudyPageTop.

(Continued)

*Primary Examiner* — Ruixiang Li
(74) *Attorney, Agent, or Firm* — Knobbe Martens Olson & Bear LLP

(57) ABSTRACT

The invention provides a method of treating or reducing the severity of thyroid-associated ophthalmopathy (TAO), also known as thyroid eye disease (TED) or Graves' ophthalmopathy or orbitopathy (GO), as well as antibodies, or antigen binding fragments thereof, and pharmaceutical compositions comprising them, useful in the methods.

15 Claims, 23 Drawing Sheets

Specification includes a Sequence Listing.

(56) References Cited

OTHER PUBLICATIONS

Clinical Trials No. NCT01868997. Teprotumumab (RV 001) Treatment in Patients With Active Thyroid Eye Disease, Version 10. Reported date submitted: Apr. 16, 2014. Date publicly available: Unknown. Date accessed: May 24, 2024. Available at: https://classic.clinicaltrials.gov/ct2/history/NCT01868997?V_10=View#StudyPageTop.
Clinical Trials No. NCT01868997. Teprotumumab (RV 001) Treatment in Patients With Active Thyroid Eye Disease, Version 11. Reported date submitted: Jul. 29, 2014. Date publicly available: Unknown. Date accessed: May 24, 2024. Available at: https://classic.clinicaltrials.gov/ct2/history/NCT01868997?V_11=View#StudyPageTop.
Clinical Trials No. NCT01868997. Teprotumumab (RV 001) Treatment in Patients With Active Thyroid Eye Disease, Version 12. Reported date submitted: Nov. 3, 2014. Date publicly available: Unknown. Date accessed: May 24, 2024. Available at: https://classic.clinicaltrials.gov/ct2/history/NCT01868997?V_12=View#StudyPageTop.
Clinical Trials No. NCT01868997. Teprotumumab (RV 001) Treatment in Patients With Active Thyroid Eye Disease, Version 13. Reported date submitted: Nov. 13, 2014. Date publicly available: Unknown. Date accessed: May 24, 2024. Available at: https://classic.clinicaltrials.gov/ct2/history/NCT01868997?V_13=View#StudyPageTop.
Clinical Trials No. NCT01868997. Teprotumumab (RV 001) Treatment in Patients With Active Thyroid Eye Disease, Version 14. Reported date submitted: Feb. 5, 2015. Date publicly available: Unknown. Date accessed: May 24, 2024. Available at: https://classic.clinicaltrials.gov/ct2/history/NCT01868997?V_14=View#StudyPageTop.
Clinical Trials No. NCT01868997. Teprotumumab (RV 001) Treatment in Patients With Active Thyroid Eye Disease, Version 15. Reported date submitted: Mar. 6, 2015. Date publicly available: Unknown. Date accessed: May 24, 2024. Available at: https://classic.clinicaltrials.gov/ct2/history/NCT01868997?V_15-View#StudyPageTop.
Clinical Trials No. NCT01868997. Teprotumumab (RV 001) Treatment in Patients With Active Thyroid Eye Disease, Version 16. Reported date submitted: Sep. 18, 2015. Date publicly available: Unknown. Date accessed: May 24, 2024. Available at: https://classic.clinicaltrials.gov/ct2/history/NCT01868997?V_16=View#StudyPageTop.
Clinical Trials No. NCT01868997. Teprotumumab (RV 001) Treatment in Patients With Active Thyroid Eye Disease, Version 17. Reported date submitted: Oct. 3, 2016. Date publicly available: Unknown. Date accessed: May 24, 2024. Available at: https://classic.clinicaltrials.gov/ct2/history/NCT01868997?V_17=View#StudyPageTop.
Clinical Trials No. NCT01868997. Teprotumumab (RV 001) Treatment in Patients With Active Thyroid Eye Disease, Version 18. Reported date submitted: Nov. 15, 2016. Date publicly available: Unknown. Date accessed: May 24, 2024. Available at: https://classic.clinicaltrials.gov/ct2/history/NCT01868997?V_18=View#StudyPageTop.
Clinical Trials No. NCT01868997. Teprotumumab (RV 001) Treatment in Patients With Active Thyroid Eye Disease, Version 19. Reported date submitted: Nov. 23, 2016. Date publicly available: Unknown. Date accessed: May 24, 2024. Available at: https://classic.clinicaltrials.gov/ct2/history/NCT01868997?V_19=View#StudyPageTop.
Clinical Trials No. NCT01868997. Teprotumumab (RV 001) Treatment in Patients With Active Thyroid Eye Disease, Version 2. Reported date submitted: Jun. 9, 2013. Date publicly available: Unknown. Date accessed: May 24, 2024. Available at https://classic.clinicaltrials.gov/ct2/history/NCT01868997?V_2=View#StudyPage Top.
Clinical Trials No. NCT01868997. Teprotumumab (RV 001) Treatment in Patients With Active Thyroid Eye Disease, Version 20. Reported date submitted: Mar. 20, 2017. Date publicly available: Unknown. Date accessed: May 24, 2024. Available at: https://classic.clinicaltrials.gov/ct2/history/NCT01868997?V_20=View#StudyPageTop.
Clinical Trials No. NCT01868997. Teprotumumab (RV 001) Treatment in Patients With Active Thyroid Eye Disease, Version 21. Reported date submitted: Aug. 10, 2017. Date publicly available: Unknown. Date accessed: May 24, 2024. Available at: https://classic.clinicaltrials.gov/ct2/history/NCT01868997?V_21=View#StudyPageTop.
Clinical Trials No. NCT01868997. Teprotumumab (RV 001) Treatment in Patients With Active Thyroid Eye Disease, Version 22. Reported date submitted: Mar. 27, 2018. Date publicly available: Unknown. Date accessed: May 24, 2024. Available at: https://classic.clinicaltrials.gov/ct2/history/NCT01868997?V_22=View#StudyPageTop.
Clinical Trials No. NCT01868997. Teprotumumab (RV 001) Treatment in Patients With Active Thyroid Eye Disease, Version 3. Reported date submitted: Jun. 13, 2013. Date publicly available: Unknown. Date accessed: May 24, 2024. Available at: https://classic.clinicaltrials.gov/ct2/history/NCT01868997?V_3=View#StudyPageTop.
Clinical Trials No. NCT01868997. Teprotumumab (RV 001) Treatment in Patients With Active Thyroid Eye Disease, Version 4. Reported date submitted: Jun. 21, 2013 Date publicly available: Unknown. Date accessed: May 24, 2024. Available at: https://classic.clinicaltrials.gov/ct2/history/NCT01868997?V_4=View#StudyPageTop.
Clinical Trials No. NCT01868997. Teprotumumab (RV 001) Treatment in Patients With Active Thyroid Eye Disease, Version 5. Reported date submitted: Jun. 27, 2013. Date publicly available: Unknown. Date accessed: May 24, 2024. Available at: https://classic.clinicaltrials.gov/ct2/history/NCT01868997?V_5-View#StudyPageTop.
Clinical Trials No. NCT01868997. Teprotumumab (RV 001) Treatment in Patients With Active Thyroid Eye Disease, Version 6. Reported date submitted: Aug. 9, 2013. Date publicly available: Unknown. Date accessed: May 24, 2024. Available at: https://classic.clinicaltrials.gov/ct2/history/NCT01868997?V_6=View#StudyPageTop.
Clinical Trials No. NCT01868997. Teprotumumab (RV 001) Treatment in Patients With Active Thyroid Eye Disease, Version 7. Reported date submitted: Sep. 12, 2013. Date publicly available: Unknown. Date accessed: May 24, 2024. Available at: https://classic.clinicaltrials.gov/ct2/history/NCT01868997?V_7=View#StudyPageTop.
Clinical Trials No. NCT01868997. Teprotumumab (RV 001) Treatment in Patients With Active Thyroid Eye Disease, Version 8. Reported date submitted: Jan. 20, 2014. Date publicly available: Unknown. Date accessed: May 24, 2024. Available at: https://classic.clinicaltrials.gov/ct2/history/NCT01868997?V_8=View#StudyPageTop.
Clinical Trials No. NCT01868997. Teprotumumab (RV 001) Treatment in Patients With Active Thyroid Eye Disease, Version 9. Reported date submitted: Mar. 17, 2014. Date publicly available: Unknown. Date accessed: May 24, 2024. Available at: https://classic.clinicaltrials.gov/ct2/history/NCT01868997?V_9=View#StudyPageTop.
Dolman, P. J. et al., "VISA Classification for Graves orbitopathy", Ophthalmic Plast Reconstr Surg, vol. 22(5), pp. 319-324 (2006).
Dolman, P. J., "Evaluating Graves' orbitopathy", Best Pract Res Clin Endocrinol Metab, vol. 26(3), pp. 229-248 (2012).
Douglas, R. et al., "Aberrant expression of the insulin-like growth factor-1 receptor by T cells from patients with Graves' disease may carry functional consequences for disease pathogenesis", J Immunol., vol. 178(5), pp. 3281-3287 (2007).
Douglas, R. et al., "B cells from patients with Graves' disease aberrantly express the IGF-1 receptor: implications for disease pathogenesis", J Immunol., vol. 181(8), pp. 5768-5774 (2008).

(56) References Cited

OTHER PUBLICATIONS

Douglas, R. et al., "Increased generation of fibrocytes in thyroid-associated ophthalmopathy", J Clin Endocrinol Metab., vol. 95(1), pp. 430-438 (2010).
Douglas, R., "Teprotumumab, an Insulin-Like Growth Factor-1 Receptor Antagonist Antibody, in the Treatment of Active Thyroid Eye Disease: A Focus on Proptosis", Eye (Lond), vol. 33(2), pp. 183-190 (2019).
Ezra, D. G. et al., Genome Level Microarray Expression Profiling Implicates IGF-1 and Wnt Signalling Dysregulation in the Pathogenesis of Thyroid Associated Ophthalmopathy, ARVO Annual Meeting Scientific Abstracts, in 2 pages (2011).
Gianoukakis, A. G. et al., "Immunoglobulin G from patients with Graves' disease induces interleukin-16 and RANTES expression in cultured human thyrocytes: a putative mechanism for T-cell infiltration of the thyroid in autoimmune disease". Endocrinology, vol. 147(4), pp. 1941-1949 (2006).
Görtz, G.-E. et al., "Pathogenic Phenotype of Adipogenesis and Hyaluronan in Orbital Fibroblasts from Female Graves' Orbitopathy Mouse Model", Endocrinology, vol. 157(10), pp. 3771-3778 (2016).
Gupta, S., "Intention-to-treat concept: A review", Perspect Clin Res, vol. 2(3), pp. 109-112 (2011).
Hansson, H., "Aspects of growth factors in exophthalmos", Acta Endocrinologica (Copenh), vol. 121(Suppl. 2), pp. 107-111 (1989).
Hoa, N. et al., "Nuclear Targeting of IGF-1 Receptor in Orbital Fibroblasts from Graves' Disease: Apparent Role of ADAM17", PLoS One, vol. 7(4), pp. e34173 (2012).
Hwang, C. J. et al., "Orbital fibroblasts from patients with thyroid-associated ophthalmopathy overexpress CD40: CD154 hyperinduces IL-6, IL-8, and MCP-1", Invest Ophthalmol Vis Sci., vol. 50(5), pp. 2262-2268 (2009).
Imai, Y. et al., "Effect of growth factors on hyaluronan and proteoglycan synthesis by retroocular tissue fibroblasts of Graves' ophthalmopathy in culture", Acta Endocrinol (Copenh), vol. 126(6), pp. 541-552 (1992).
Kabat, E. A. et al., *Sequences of Proteins of Immunological Interest*, NIH Pub. No. 91-3242. Public Health Service, National Institutes of Health, 5th edition, pp. 647-669 (1991).
Khong, J. J. et al., "Pathogenesis of thyroid eye disease: review and update on molecular mechanisms", Br J Ophthalmol., vol. 100(1), pp. 142-150 (2016).
Khoo, T. K. et al., "Pathogenesis of Graves' Ophthalmopathy: The Role of Autoantibodies", Thyroid, vol. 17(10), pp. 1013-1018 (2007).
Krieger, C. C. et al., "Thyroid Stimulating Hormone (TSH)/Insulin-like Growth Factor 1 (IGF1) Receptor Cross-talk in Human Cells", Curr Opin Endocr Metab Res, vol. 2, pp. 29-33 (2018).
Krieger, C. C. et al., "TSH/IGF-1 Receptor Cross-Talk Rapidly Activates Extracellular Signal-Regulated Kinases in Multiple Cell Types", Endocrinology, vol. 158(10), pp. 3676-3683 (2017).
Krieger, C. C. et al., "TSHR/IGF-1R Cross-Talk, Not IGF-1R Stimulating Antibodies, Mediates Graves' Ophthalmopathy Pathogenesis", Thyroid, vol. 27(5), pp. 746-747 (2017).
Kumar, S. et al., "A stimulatory thyrotropin receptor antibody enhances hyaluronic acid synthesis in graves' orbital fibroblasts: inhibition by an IGF-I receptor blocking antibody", J Clin Endocrinol Metab., vol. 97(5), pp. 1681-1687 (2012).
Kumar, S. et al., "Forkhead Transcription Factor FOXO1 Is Regulated by Both a Stimulatory Thyrotropin Receptor Antibody and Insulin-Like Growth Factor-1 in Orbital Fibroblasts from Patients with Graves' Ophthalmopathy", Thyroid, vol. 25(10), pp. 1145-1150 (2015).
Kurzrock, R. et al., "A Phase I Study of Weekly R1507, A Human Monoclonal Antibody Insulin-like Growth Factor-I Receptor Antagonist, in Patients with Advanced Solid Tumors", Clin Cancer Res, vol. 16(8), pp. 2458-2465 (2010).
Lovell, D. J. et al., "Adalimumab with or without Methotrexate in Juvenile Rheumatoid Arthritis", N Engl J Med, vol. 359, pp. 810-820 (2008).
Ma, H. et al., "The Adverse Events Profile of Anti-IGF-IR Monoclonal Antibodies in Cancer Therapy", Br J Clin Pharmacol, vol. 77(6), pp. 917-928 (2013).
Marcus-Samuels, B. et al., "Evidence that Graves Ophthalmopathy Immunoglobulins Do Not Directly Activate IGF-1 Receptors", Thyroid, vol. 28(5), pp. 650-655 (2018).
Mourits, M. et al., "Clinical activity score as a guide in the management of patients with Graves' ophthalmopathy", Clin Endocrinol (Oxf), vol. 47(1), pp. 9-14 (1997).
Mourits, M. et al., "Clinical criteria for the assessment of disease activity in Graves' ophthalmopathy: a novel approach", Br J Ophthalmol, vol. 73(8), pp. 639-644 (1989).
Naik, V. M. et al., "Immunopathogenesis of thyroid eye disease: emerging paradigms", Surv Ophthalmol., vol. 55(3), pp. 215-226 (2010).
Pappo, A. et al., "R1507, a Monoclonal Antibody to the Insulin-Like Growth Factor 1 Receptor, in Patients with Recurrent or Refractory Ewing Sarcoma Family of Tumors: Results of a Phase II Sarcoma Alliance for Research Through Collaboration Study", J Clin Oncol, vol. 29(34), pp. 4541-4547, (2011).
Pawlowski, P. et al., "Decreased Frequencies of Peripheral Blood CD4+CD25+CD127-Foxp3+ in Patients with Graves' Disease and Graves' Orbitopathy: Enhancing Effect of Insulin Growth Factor-1 on Treg Cells", Horm Metab Res., vol. 49(3), pp. 185-191 (2017).
Piantanida, E. et al., "Teprotumumab: A New Avenue for the Management of Moderate-to-Severe and Active Graves' Orbitopathy?", J Endocrinol Invest, vol. 40(8), pp. 885-887 (2017).
Place, R. F. et al., "Inhibiting thyrotropin/insulin-like growth factor 1 receptor crosstalk to treat Graves' ophthalmopathy: studies in orbital fibroblasts in vitro", Br J Pharmacol., vol. 174(4), pp. 328-340 (2017).
Pritchard, J. et al., "Igs from patients with Graves' disease induce the expression of T cell chemoattractants in their fibroblasts", J Immunol., vol. 168(2), pp. 942-950 (2002).
Pritchard, J. et al., "Immunoglobulin activation of T cell chemoattractant expression in fibroblasts from patients with Graves' disease is mediated through the insulin-like growth factor I receptor pathway", J Immunol., vol. 170(12), pp. 6348-6354 (2003).
Ramalingam, S. et al., "Randomized Phase II Study of Erlotinib in Combination with Placebo or R1507, a Monoclonal Antibody to Insulin-Like Growth Factor-1 Receptor, for Advanced-Stage Non-Small-Cell Lung Cancer", J Clin Oncol, vol. 29(34), pp. 4574-4580 (2011).
Salvi, M. et al., "Efficacy of B-cell targeted therapy with rituximab in patients with active moderate to severe Graves' orbitopathy: a randomized controlled study", J Clin Endocrinol Metab., vol. 100(2), pp. 422-431 (2015).
Salvi, M., "Immunotherapy for Graves' ophthalmopathy", Curr Opin Endocrinol Diabetes Obes., vol. 21(5), pp. 409-414 (2014).
Smith, T. et al., "Building the Case for Insulin-Like Growth Factor Receptor-I Involvement in Thyroid-Associated Ophthalmopathy", Front Endocrinol (Lausanne), vol. 7, Article 167, in 8 pages (2017).
Smith, T. et al., "Insulin-Like Growth Factor-I Regulation of Immune Function: A Potential Therapeutic Target in Autoimmune Diseases?", Pharmacological Rev., vol. 62(2), pp. 199-236 (2010).
Smith, T. et al., "Immunoglobulins from patients with Graves' disease induce hyaluronan synthesis in their orbital fibroblasts through the self-antigen, insulin-like growth factor-I receptor", J Clin Endocrinol Metab, vol. 89(10), pp. 5076-5080 (2004).
Smith, T. et al., "New Advances in Understanding Thyroid-Associated Ophthalmopathy and the Potential Role for Insulin-Like Growth Factor-I Receptor [version 1; referees: 2 approved]", F1000 Research 2018, 7(F1000 Faculty Rev):134 last updated Feb. 1, 2018, in 9 pages (2018).
Smith, T. et al., "Pathogenesis of Graves' orbitopathy: A 2010 update", J Endocrinol Invest., vol. 33(6), pp. 414-421 (2010).
Smith, T. et al., "Recognizing the Putative Role for TSH Receptor Expressing Fibrocytes in Thyroid-Associated Ophthalmopathy may solve several mysteries", Nat Rev Endocrinol., vol. 11(3), pp. 171-181 (2015).
Smith, T. et al., "Role of IGF-1 pathway in the pathogenesis of Graves' orbitopathy", Best Pract Res Clin Endocrinol Metab., vol. 26(3), pp. 291-302 (2012).

(56) References Cited

OTHER PUBLICATIONS

Smith, T. et al., "Teprotumumab for Thyroid-Associated Ophthalmopathy", N Engl J Med., vol. 376(18), pp. 1748-1761 (2017).
Smith, T. et al., "Unique attributes of orbital fibroblasts and global alterations in IGF-1 receptor signaling could explain thyroid-associated ophthalmopathy", Thyroid, vol. 18(9), pp. 983-988 (2008).
Song, D. et al., "Locally produced insulin-like growth factor-1 by orbital fibroblasts as implicative pathogenic factor rather than systemically circulated IGF-1 for patients with thyroid-associated ophthalmopathy", Graefes Arch Clin Exp Ophthalmol, vol. 250(3), pp. 433-440 (2012).
Stan, M. N. et al., "Randomized controlled trial of rituximab in patients with Graves' orbitopathy", J Clin Endocrinol Metab., vol. 100(2), pp. 432-441 (2015).
Terwee, C. B. et al., "Development of a disease specific quality of life questionnaire for patients with Graves' ophthalmopathy: the GO-QOL", Br J Ophthalmopathy, vol. 82, pp. 773-779 (1998).
Tsui, S. et al., "Evidence for an association between thyroid-stimulating hormone and insulin-like growth factor 1 receptors: a tale of two antigens implicated in Graves' disease", J Immunol, vol. 181(6), pp. 4397-4405 (2008).
Ugradar, S. et al., "Teprotumumab for non-inflammatory thyroid eye disease (TED): evidence for increased IGF-1R expression", Eye (Lond), vol. 35(9), pp. 2607-2612 (2021).
Ugradar, S. et al., "Teprotumumab for the treatment of chronic thyroid eye disease", Eye (Lond), vol. 36(8), pp. 1553-1559 (2022).
Varewijck, A. J. et al., "Circulating IgGs may modulate IGF-I receptor stimulating activity in a subset of patients with Graves' ophthalmopathy", J Clin Endocrinol Metab., vol. 98(2), pp. 769-776 (2013).
Weightman, D. R. et al., "Autoantibodies to IGF-1 binding sites in thyroid associated ophthalmopathy", Autoimmunity, vol. 16(4), pp. 251-257 (1993).
Werner, S., "Classification of the eye changes of Graves' disease", Am J Ophthalmol, vol. 68(4), pp. 646-648 (1969).
Werner, S., "Modification of the classification of the eye changes of Graves' disease", Am J Ophthalmol, vol. 83(5), pp. 725-727 (1977).
Wiersinga, W. M. et al., "Clinical assessment of patients with Graves' orbitopathy: the European Group on Graves' Orbitopathy recommendations to generalists, specialists and clinical researchers", European Journal of Endocrinology, vol. 155, pp. 387-389 (2006).
Wiersinga, W. M., "Management of Graves opthalmopathy", Nat Clin Pract Endocrinol Metab., vol. 3(5), pp. 396-404 (2007).
Xu, N. et al., "Comparative Efficacy of Medical Treatments for Thyroid Eye Disease: A Network Meta-Analysis", J Ophthalmol., 7184163, in 10 pages (2018).
Zhang, L. et al., "Possible Targets for Nonimmunosuppressive Therapy of Graves' Orbitopathy", J Clin Endocrinol Metab., vol. 99(7), pp. E1183-E1190 (2014).
Zhao, P. et al., "Insulin-like growth factor 1 promotes the proliferation and adipogenesis of orbital adipose-derived stromal cells in thyroid-associated ophthalmopathy", Exp Eye Res, vol. 107, pp. 65-73 (2013).
U.S. Appl. No. 16/256,221; Restriction Response, dated Oct. 16, 2020; 7 pages.
U.S. Appl. No. 16/256,221; Non-Final Office Action, dated Apr. 29, 2021; 28 pages.
U.S. Appl. No. 16/256,221; Notice of Allowance, dated Aug. 23, 2021; 12 pages.
U.S. Appl. No. 16/293,293; Restriction Requirement, dated Dec. 10, 2020; 5 pages.
U.S. Appl. No. 16/293,293; Non-Final Office Action, dated Apr. 29, 2021; 27 pages.
U.S. Appl. No. 16/293,293; Notice of Allowance, dated Aug. 20, 2021; 12 pages.
U.S. Appl. No. 17/117,625, Office Action, dated Sep. 14, 2022; 14 pages.
U.S. Appl. No. 17/531,365; Non-Final Office Action, dated Mar. 19, 2024; 18 pages.
U.S. Appl. No. 17/531,365; Final Office Action, dated Jul. 11, 2024; 15 pages.
U.S. Appl. No. 17/531,368; Restriction Requirement, dated Mar. 18, 2024; 5 pages.
U.S. Appl. No. 17/531,368; Non-Final Office Action, dated Jul. 11, 2024; 16 pages.
International Application No. PCT/US2019/020770; International Search Report and Written Opinion, date of mailing Jul. 9, 2019; 12 pages.
International Application No. PCT/US2019/020770; International Preliminary Report on Patentability, date of issuance Sep. 17, 2020; 9 pages.
Xu, N. et al., "Ocular Surface Characteristics and Impression Cytology in Patients with Active versus Inactive Thyroid Eye Disease", Eye Science, vol. 27, No. 2, pp. 64-68 (2012).
U.S. Appl. No. 17/531,365, Notice of Allowance, dated Sep. 13, 2024; 6 pages.
U.S. Appl. No. 18/929,510, Non-Final Office Action, dated Jan. 7, 2025; 15 pages.
U.S. Appl. No. 18/929,510, Notice of Allowance, dated Feb. 21, 2025; 6 pages.
U.S. Patent Application No. 17/531, 368; Notice of Allowance, dated Nov. 18, 2024; 7 pages.
U.S. Appl. No. 17/531,368; Notice of Allowance, dated Mar. 12, 2025; 6 pages.

METHODS FOR THE TREATMENT OF THYROID EYE DISEASE

This application is a continuation of U.S. application Ser. No. 18/182,182, filed Mar. 10, 2023, which is a continuation of U.S. application Ser. No. 17/117,625, which is a continuation-in-part of, and claims the benefit of priority of, U.S. application Ser. No. 16/293,293, filed Mar. 5, 2019, which claims the benefit of priority of U.S. Provisional Application No. 62/638,689, filed Mar. 5, 2018; is a continuation-in-part of, and claims the benefit of priority of, U.S. application Ser. No. 16/256,221, filed Jan. 24, 2019, which claims the benefit of priority of U.S. Provisional Applications No. 62/621,201, filed Jan. 24, 2018, No. 62/635,342, filed Feb. 26, 2018, and No. 62/716,194, filed Aug. 8, 2018; and claims the benefit of priority of U.S. Provisional Application No. 62/946,239, filed Dec. 10, 2019.

SEQUENCE LISTING

The instant application contains a Sequence Listing which has been submitted electronically in XML format and is hereby incorporated by reference in its entirety. Said XML copy, created on Oct. 18, 2023, is named 58651-813_302_SL.xml and is 11.4 KB in size, and is incorporated by references as if written herein in its entirety.

Thyroid-associated ophthalmopathy (TAO), also known as thyroid eye disease (TED), Graves' ophthalmopathy or orbitopathy (GO), thyrotoxic exophthalmos, dysthyroid ophthalmopathy, and several other terms, is orbitopathy associated with thyroid dysfunction. TED is divided into two types. Active TED, which typically lasts 1-3 years, is characterized by an ongoing autoimmune/inflammatory response in the soft tissues of the orbit. Active TED is responsible for the expansion and remodeling of the ocular soft tissues. The autoimmune/inflammatory response of active TED spontaneously resolves and the condition transitions into inactive TED. Inactive TED is the term used to describe the long-term/permanent sequelae of active TED.

The cause of TED is unknown. TED is typically associated with Graves' hyperthyroidism, but can also occur as part of other autoimmune conditions that affect the thyroid gland and produce pathology in orbital and periorbital tissue, and, rarely, the pretibial skin (pretibial myxedema) or digits (thyroid acropachy). TED is an autoimmune orbitopathy in which the orbital and periocular soft tissues are primarily affected with secondary effects on the eye and vision. In TED, as a result of inflammation and expansion of orbital soft tissues, primarily eye muscles and adipose, the eyes are forced forward (bulge) out of their sockets—a phenomenon termed proptosis or exophthalmos.

The annual incidence rate of TED has been estimated at 16 cases per 100,000 women and 2.9 cases per 100,000 men from a study based in one largely rural Minnesota community. There appears to be a female preponderance in which women are affected 2.5-6 times more frequently than men; however, severe cases occur more often in men than in women. In addition, most patients are aged 30-50 years, with severe cases appearing to be more frequent in those older than 50 years. Although most cases of TED do not result in loss of vision, this condition can cause vision-threatening exposure keratopathy, troublesome diplopia (double vision), and compressive dysthyroid optic neuropathy.

TAO may precede, coincide with, or follow the systemic complications of dysthyroidism. The ocular manifestations of TED include upper eyelid retraction, lid lag, swelling, redness (erythema), conjunctivitis, and bulging eyes (exophthalmos or proptosis), chemosis, periorbital edema, and altered ocular motility with significant functional, social, and cosmetic consequences.

Many of the signs and symptoms of TED, including proptosis and ocular congestion, result from expansion of the orbital adipose tissue and periocular muscles. The adipose tissue volume increases owing in part to new fat cell development (adipogenesis) within the orbital fat. The accumulation of hydrophilic glycosaminoglycans, primarily hyaluronic acid, within the orbital adipose tissue and the perimysial connective tissue between the extraocular muscle fibers, further expands the fat compartments and enlarges the extraocular muscle bodies. Hyaluronic acid is produced by fibroblasts residing within the orbital fat and extraocular muscles, and its synthesis in vitro is stimulated by several cytokines and growth factors, including IL-1β, interferon-γ, platelet-derived growth factor, thyroid stimulating hormone (TSH) and insulin-like growth factor I (IGF-I).

TAO is commonly considered to be the autoimmune orbital manifestation of Graves' Disease (GD). However, only approximately 30% of patients with Graves' hyperthyroidism manifest clinically relevant ocular pathology indicating there is mechanistic heterogeneity and differentiation between the conditions. The molecular mechanisms underlying TED remain unclear. It is accepted that the generation of autoantibodies that act as agonists on the thyroid-stimulating hormone receptor (TSHR) is responsible for Graves' hyperthyroidism. Pathogenic overstimulation of TSHR, leads to overproduction of thyroid hormones (T3 and T4) and accelerated metabolism of many tissues.

In active TED, autoantibodies trigger connective tissue and fat to expand, in part from stimulating excessive synthesis of hyaluronan. The expanded tissues are infiltrated with T and B cells, become inflamed, and get and extensively remodeled. It has been suggested that TSHR might have some pathogenic role in the development of active TED. Indeed, a positive correlation has been found between anti-TSHR antibodies and the degree of TED activity. However, no definitive link has been established, and a proportion of TED patients remain euthyroid throughout the course of their disease.

Antibodies that activate the insulin-like growth factor I receptor (IGF-1R) have also been detected and implicated in active TED. Without being bound to any theory, it is believed that TSHR and IGF-1R form a physical and functional complex in orbital fibroblasts, and that blocking IGF-1R appears to attenuate both IGF-1 and TSH-dependent signaling. It has been suggested that blocking IGF-1R using an antibody antagonist might reduce both TSHR- and IGF-I-dependent signaling and therefore interrupt the pathological activities of autoantibodies acting as agonists on either receptor.

IGF-1R is a widely expressed heterotetrameric protein involved in the regulation of proliferation and metabolic function of many cell types. It is a tyrosine kinase receptor comprising two subunits. IGF-1Rα contains a ligand-binding domain while IGF-1Rβ is involved in signaling and contains tyrosine phosphorylation sites. Monoclonal antibodies directed against IGF-1R have been developed and assessed as a therapeutic strategy for several types of solid tumors and lymphomas.

Management of hyperthyroidism due to Graves' disease is imperfect because therapies targeting the specific underlying pathogenic autoimmune mechanisms of the disease are lacking. Even more complex is the treatment of moderate-to-severe active TED. Although recent years have witnessed a better understanding of its pathogenesis, TED remains a therapeutic challenge and dilemma. There are no approved drugs to treat active TED. Intravenous glucocorticoids (ivGCs) and oral glucocorticoids are used to treat patients with moderate-to-severe active TED, but results are seldom satisfactory. Partial responses are frequent and relapses (rebound) after drug withdrawal are not uncommon. Adverse events do occur and many patients eventually require rehabilitative surgery conducted when their condition has transitioned to inactive TED.

Recently, attention has been focused on the use of biologicals, which might specifically intervene on the pathogenic mechanisms of TED. In 2015 two small, monocenter, randomized clinical trials (RCTs) investigated the effects of rituximab, a CD20+B cell-depleting agent, versus placebo or ivGCs, respectively. The results from the two trials were conflicting; they were negative (no differences with placebo) in the first trial, but positive (beneficial effects comparable to ivGCs) in the second one. The effectiveness of rituximab for moderate-to-severe active TED therefore remains to be determined. The recent guidelines published by the European Thyroid Association/European Group on Graves' Orbitopathy (EUGOGO) indicate rituximab as a possible second-line treatment for patients poorly responsive to a first course of ivGCs. As with rituximab, there is no dependable evidence concerning other potential therapeutic agents, such as adalimumab, etanercept, infliximab, or monoclonals or small molecules blocking the TSH receptor. The use of the interleukin-6 receptor monoclonal antibody, tocilizumab, based on an ongoing RCT also remains to be determined.

As stated above, medical therapies for moderate-to-severe TED that have proved to be effective and safe in adequately powered, prospective, placebo-controlled trials are lacking. Previous clinical trials, which were rarely placebo-controlled, suggest that high dose glucocorticoids, alone, or with radiotherapy, can reduce inflammation-related signs and symptoms in patients with active ophthalmopathy, but only minimally affect proptosis and can cause dose-limiting adverse reactions.

Immunoglobulins that activate IGF-1R signaling have been detected in patients with GD and TED. Furthermore, IGF-I synergistically enhances the actions of thyrotropin. IGF-IR, a membrane-spanning tyrosine kinase receptor with roles in development and metabolism, also stimulates immune function and thus might be targeted therapeutically in autoimmune diseases. IGF-1R is overexpressed by orbital fibroblasts and by T cells and B cells in persons with GD and TED. It forms a signaling complex with TSHR through which it is transactivated. In vitro studies of orbital fibroblasts and fibrocytes show that IGF-1R-inhibitory antibodies can attenuate the actions of IGF-I, thyrotropin, thyroid-stimulating immunoglobulins, and immunoglobulins isolated from patients with GD and TED.

These observations prompted a trial of teprotumumab, a fully human IGF-1R-inhibitory monoclonal antibody, in patients with active, moderate-to-severe TED. Although this trial of teprotumumab proved successful and reduced proptosis by at least 2 mm and reduced the clinical activity score (CAS) by at least 2 points in several patients, there were some patients who either did not respond to this treatment or, responded to the treatment and later relapsed.

Accordingly, provided herein are antibodies against insulin-like growth factor I receptor (IGF-1R) for use in the treatment of thyroid eye disease (TED; GO or TAO).

Also provided herein is a method of reducing proptosis (e.g., by at least 2 mm) in a subject with thyroid eye disease (TED; GO or TAO) comprising administering to the subject an effective amount of an antibody, or an antigen binding fragment thereof, wherein the antibody specifically binds to and inhibits insulin-like growth factor-I receptor (IGF-1R).

Also provided herein is a method of reducing the clinical activity score (CAS) in a subject with thyroid eye disease (TED; GO or TAO) comprising administering to the subject an effective amount of an antibody, or an antigen binding fragment thereof, wherein the antibody specifically binds to and inhibits insulin-like growth factor-I receptor (IGF-1R).

Also provided herein is a method of reducing proptosis (e.g., by at least 2 mm) and reducing the clinical activity score (CAS) in a subject with thyroid eye disease (TED; GO or TAO) comprising administering to the subject an effective amount of an antibody, or an antigen binding fragment thereof, wherein the antibody specifically binds to and inhibits insulin-like growth factor-I receptor (IGF-1R).

Also provided herein is a method of treating or reducing the severity of thyroid eye disease (TED; GO or TAO) comprising administering to a subject in need thereof an effective amount of an antibody, or an antigen binding fragment thereof, wherein the antibody specifically binds to and inhibits IGF-1R, and wherein the antibody (i) reduces proptosis by at least 2 mm; and/or (ii) reduces the CAS in the subject by at least 2 points (on the 7-point version of the scale—as described below).

Also provided herein is a method of reducing proptosis by at least 4 mm in a subject with thyroid eye disease (TED; GO or TAO) comprising administering to the subject an effective amount of an antibody, or an antigen binding fragment thereof, wherein the antibody specifically binds to and inhibits IGF-1R.

Also provided herein is a method of treating or reducing the severity of thyroid eye disease (TED; GO or TAO) comprising administering to a subject in need thereof an effective amount of an antibody, or an antigen binding fragment thereof, wherein the antibody specifically binds to and inhibits IGF-1R, and wherein the antibody reduces proptosis by at least 4 mm.

Also provided herein is a method of treating or reducing the severity of diplopia in a subject with thyroid eye disease (TED; GO or TAO), comprising administering to the subject, an effective amount of an antibody, or an antigen binding fragment thereof, wherein the antibody specifically binds to and inhibits IGF-1R.

Also provided herein is a method of treating or reducing the severity of constant diplopia (CD) in a subject with thyroid eye disease (TED; GO or TAO) comprising administering to the subject an effective amount of an antibody, or an antigen binding fragment thereof, wherein the antibody specifically binds to and inhibits IGF-IR (e.g., teprotumumab). In some embodiments, the treatment with teprotumumab improves the CD QoL in patients with severe TED.

Also provided herein is a method of treating or reducing the severity of diplopia in a subject with thyroid eye disease (TED; GO or TAO) comprising administering to the subject an effective amount of an antibody, or an antigen binding fragment thereof, wherein the antibody specifically binds to and inhibits IGF-1R (e.g., teprotumumab), that results in improved diplopia relative to placebo which is sustained out to 51 weeks after drug discontinuation.

The antibodies and methods disclosed are also useful in patients who previously received treatment an antibody, or an antigen binding fragment thereof, that specifically binds to and/or inhibits insulin like growth factor-I receptor (IGF-1R) and either did not respond to said prior treatment or responded to said prior treatment and later relapsed.

Accordingly, also provided herein is a method of reducing proptosis in an eye in a subject with thyroid eye disease (TED; GO or TAO) who has previously undergone prior treatment with an antibody, or an antigen binding fragment thereof, that specifically binds to and/or inhibits insulin like growth factor-I receptor (IGF-1R) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-1R).

Also provided herein is a method of reducing proptosis by at least 2 mm in an eye without a deterioration of 2 mm or more in the other (or fellow eye) in a subject with thyroid eye disease (TED; GO or TAO) comprising administering to said subject an effective amount of an antibody, or an antigen binding fragment thereof, wherein said antibody specifically binds to and inhibits Insulin Like Growth Factor-I Receptor (IGF IR). The subject is one who has undergone prior treatment with said antibody or antigen binding fragment thereof, and either did not respond to said prior treatment or relapsed after said prior treatment.

Also provided herein is a method of reducing Clinical Activity Score (CAS) of thyroid eye disease (TED; GO or TAO) in a subject who has undergone prior treatment with an antibody, or an antigen binding fragment thereof, that specifically binds to and inhibits IGF-1R, and either did not respond to said prior treatment or relapsed after said prior treatment, comprising administering to a subject in need thereof an effective amount of an antibody, or an antigen binding fragment thereof, wherein said antibody specifically binds to and inhibits IGF-1R.

In some embodiments, CAS is reduced in said subject to either one (1) or zero (0) (on the 7-point version of the CAS scale—as described below).

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points. In yet another embodiment, the reduction in CAS is by 5 or more points.

In one embodiment, as a result of the treatment, the CAS is reduced to one (1). In another embodiment, as a result of the treatment, the CAS is reduced to zero (0).

Also provided herein is a method of treating or reducing the severity of thyroid eye disease (TED; GO or TAO) comprising administering to a subject who has undergone prior treatment with an antibody, or an antigen binding fragment thereof, that specifically binds to and inhibits IGF-1R, and either did not respond to said prior treatment or responded to said prior treatment and later relapsed, the antibody, or an antigen binding fragment thereof, wherein said antibody specifically binds to and inhibits IGF-1R. The antibody may be administered, e.g., in the following amounts: about 10 mg/kg antibody as a first dose; and about 20 mg/kg antibody in subsequent doses.

Also provided herein is a method of treating or reducing the severity of thyroid eye disease (TED; GO or TAO) in a subject who has undergone prior treatment with an antibody, or an antigen binding fragment thereof, that specifically binds to and/or inhibits insulin like growth factor-I receptor (IGF-1R) and either did not respond to said prior treatment or relapsed after said prior treatment comprising administering to a subject in need thereof an effective amount of an antibody, or an antigen binding fragment thereof, wherein said antibody specifically binds to and inhibits IGF-1R, and wherein said antibody (i) reduces proptosis by at least 2 mm in an eye; (ii) is not accompanied by a deterioration of 2 mm or more in the other (or fellow eye); and (iii) reduces the CAS in said subject to either one (1) or zero (0) (on the 7-point version of the scale—as described below.

Also provided herein is a method of treating or reducing the severity of thyroid eye disease (TED; GO or TAO) comprising administering to a subject in need thereof an effective amount of an antibody, or an antigen binding fragment thereof, wherein said antibody specifically binds to and inhibits IGF-IR, and wherein said antibody reduces proptosis by at least 2 mm as well as reduces the CAS to either one (1) or zero (0). As stated above, the subject is one who has undergone prior treatment with said antibody or antigen binding fragment thereof, and either did not respond to said prior treatment or relapsed after said prior treatment.

Also provided herein is a method of treating or reducing the severity of thyroid eye disease (TED; GO or TAO) in a subject with TED who has previously undergone prior treatment with an antibody, or an antigen binding fragment thereof, that specifically binds to and/or inhibits insulin like growth factor-I receptor (IGF-1R) and either did not respond to said prior treatment or responded to said prior treatment and later relapsed, comprising administering to a subject in need thereof an effective amount of a pharmaceutical composition comprising an antibody that specifically binds to and inhibits IGF-1R, or an antigen binding fragment thereof, and a pharmaceutically acceptable excipient or diluent or carrier.

Also provided herein is a method of reducing proptosis in an eye in a subject with thyroid eye disease (TED; GO or TAO) who has previously undergone prior treatment with an antibody, or an antigen binding fragment thereof, that specifically binds to and/or inhibits insulin like growth factor-I receptor (IGF-1R) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-1R).

Also provided herein is a method of treating or reducing the severity of thyroid eye disease (TED; GO or TAO) comprising administering to a subject who has undergone prior treatment with an antibody, or an antigen binding fragment thereof, that specifically binds to and inhibits IGF-1R, and either did not respond to said prior treatment or responded to said prior treatment and later relapsed, the antibody, or an antigen binding fragment thereof, wherein said antibody specifically binds to and inhibits IGF-1R.

Also provided herein is a method of improving the quality of life in a subject with thyroid eye disease (TED; GO or TAO) who has undergone prior treatment with an antibody, or an antigen binding fragment thereof, that specifically binds to and inhibits IGF-1R, and either did not respond to said prior treatment or responded to said prior treatment and later relapsed, comprising administering to the subject an effective amount of an antibody, or an antigen binding fragment thereof, wherein the antibody specifically binds to and inhibits IGF-1R.

Also provided herein is a method of treating or reducing diplopia or the severity of diplopia in a subject with thyroid eye disease (TED; GO or TAO) who has undergone prior treatment with an antibody, or an antigen binding fragment thereof, that specifically binds to and inhibits IGF-1R, and either did not respond to said prior treatment or responded to said prior treatment and later relapsed, comprising administering to the subject an effective amount of an antibody, or an antigen binding fragment thereof, wherein the antibody specifically binds to and inhibits IGF-1R.

In some embodiments, the diplopia is constant diplopia. In some embodiments, the diplopia is inconstant diplopia. In some embodiments, the diplopia is intermittent diplopia.

In some embodiments, the improvement in or reduction in severity of diplopia is sustained at least 20, 30, 40, or 50 weeks after discontinuation of antibody administration. In some embodiments, the improvement in or reduction in severity of diplopia is sustained 20-30, 30-40, 40-50, or 50-60 weeks after discontinuation of antibody administration. In some embodiments, the improvement in or reduction in severity of diplopia is sustained at least 20 weeks after discontinuation of antibody administration. In some embodiments, the improvement in or reduction in severity of diplopia is sustained at least 50 weeks after discontinuation of antibody administration.

Also provided herein is a method of treating or reducing the severity of constant diplopia (CD) in a subject with thyroid eye disease (TED; GO or TAO) who has undergone prior treatment with an antibody, or an antigen binding fragment thereof, that specifically binds to and inhibits IGF-1R, and either did not respond to said prior treatment or responded to said prior treatment and later relapsed, comprising administering to the subject an effective amount of an antibody, or an antigen binding fragment thereof, wherein the antibody specifically binds to and inhibits IGF-1R (e.g., teprotumumab). In some embodiments, the treatment with teprotumumab improves the CD QOL in patients with severe TED.

Also provided herein is a method of treating or reducing the severity of diplopia in a subject with thyroid eye disease (TED; GO or TAO) who has undergone prior treatment with an antibody, or an antigen binding fragment thereof, that specifically binds to and inhibits IGF-1R, and either did not respond to said prior treatment or responded to said prior treatment and later relapsed, comprising administering to the subject an effective amount of an antibody, or an antigen binding fragment thereof, wherein the antibody specifically binds to and inhibits IGF-1R (e.g., teprotumumab), that results in improved diplopia relative to placebo which is sustained out to 51 weeks after drug discontinuation.

In some embodiments, the antibody, or an antigen binding fragment thereof, that is administered to the subject comprises: (i) heavy chain complementarity determining region (CDR) 1, 2 and 3, i.e., CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively. In some embodiments, the antibody, or an antigen binding fragment thereof, that is administered to the subject comprises the heavy chain CDRs and the light chain CDRs of teprotumumab.

In some embodiments, the antibody, or an antigen binding fragment thereof, that is administered to the subject comprises: (i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12. In some embodiments, the antibody, or an antigen binding fragment thereof, that is administered to the subject comprises the heavy chain variable region and light chain variable region of teprotumumab.

In some embodiments, the antibody that is administered to the subject is antibody 1 or antibody 2, as disclosed herein, or an antigen binding fragment thereof. In some embodiments of the invention, antibody 1 is teprotumumab.

Also provided herein is a method of reducing the severity of thyroid eye disease (TED; GO or TAO) comprising administering to a subject in need thereof an effective amount of a pharmaceutical composition comprising an antibody that specifically binds to and inhibits IGF-1R, or an antigen binding fragment thereof, and a pharmaceutically acceptable excipient or diluent or carrier. In some embodiments, the antibody, or an antigen binding fragment thereof, comprises the complementarity determining regions or heavy and/or light chain variable regions as disclosed herein.

DESCRIPTION OF FIGURES

FIG. 1 shows the screening, randomization to teprotumumab therapy or placebo, completion, and follow-up of patients from the trial of patients from the trial.

FIGS. 2-4 show the primary efficacy endpoints of the clinical studies for the teprotumumab and placebo groups.

FIG. 2 compares the onset of response amongst responders in teprotumumab and placebo groups.

FIG. 3 compares the proportion of patients who had a response between the teprotumumab and placebo groups at weeks 6, 12, 18, and 24.

FIG. 4 compares the level of response between the teprotumumab group than in the placebo group FIGS. 5-10 show the secondary efficacy end points for the teprotumumab group and the placebo group from the trial. In FIGS. 5, 6, 8, and 9, means±SE are shown, and P values were calculated with the use of a mixed model of repeated-measurements analysis involving the intention-to-treat population (45 patients in the placebo group and 42 patients in the teprotumumab group). P values shown in FIGS. 7 and 10 were calculated with the use of the chi-square test comparing data from patients who had a response with data from those who did not.

FIG. 5 shows the change in proptosis from baseline.

FIG. 6 shows the change in the Clinical Activity Score from baseline.

FIG. 7 shows the results of the post hoc analysis of the percentage of patients with a Clinical Activity Score of 0 or 1 through week 24.

FIG. 8 shows the change in the visual-functioning subscale of the Graves' ophthalmopathy-specific quality-of-life scale (GO-QOL) from baseline. Scores on the visual-functioning subscale range from 0 to 100, and a change of 8 points is considered to be clinically relevant.

FIG. 9 shows the change in the GO-QOL appearance subscale from baseline. Scores on the appearance subscale range from 0 to 100, and a change of 8 points is considered to be clinically relevant.

FIG. 10 shows the response with respect to subjective diplopia. In this assessment, patients are categorized according to four grades, and a change of one grade or more is considered to be clinically relevant.

FIGS. 11-24 are from the Phase 3 study disclosed below in Example 2.

FIG. 11 shows proptosis responder analysis (percent of patients with ≥2 mm reduction in proptosis from baseline in study eye).

FIG. 12 shows change from baseline in proptosis (least squares mean±standard error).

FIG. 13 shows percent of patients with clinical activity score (CAS) of 0 or 1 in study eye.

FIG. 14 shows overall responder rate (percent of patients with ≥2-point reduction in CAS and ≥2 mm reduction in proptosis from baseline in study eye).

FIG. 15 shows diplopia response (percent of patients with improvement of at least 1 grade from baseline).

FIG. 16 shows change from baseline in transformed GO-QOL score (least squares mean±standard error).

FIG. 17 shows the mean change from baseline in GO-QOL visual functioning subscale score (least squares, [SE]), in teprotumumab (top black line, circles) vs. placebo (bottom gray line, squares.

FIG. 18 shows the mean change from baseline in GO-QOL visual appearance subscale score (least squares, [SE]), in teprotumumab (top black line, circles) vs. placebo (bottom gray line, squares.

FIG. 19 shows Coronal T1 post fat saturation in FIG. 17A, pre-treatment, and FIG. 17B, post-treatment with teprotumumab.

FIG. 20 shows the percent of patients who showed at least a 2 mm improvement in proptosis from baseline to week 24 and maintained the improvement at week 72.

FIG. 21 shows the percent of patients who showed at least a one-grade improvement in diplopia from baseline to week 24 and maintained the improvement at week 72.

FIG. 22 shows the percentage of patients who achieved a≥1 grade improvement and who achieved compete resolution of diplopia; in each pair of bars, the left bar is teprotumumab and the right is placebo.

FIG. 23 compares the durability in response of teprotumumab to other biologics in different disease states. 1) The SILIQ (brodalumab "Response" was sPGA of 0 or 1; data from Trial 1 (randomized withdrawal study). 2) The HUMIRA (adalimumab) "Response" was ACR Pedi 30 from trial DE038; see, e.g., N Engl J Med 2008. 3) The ENTYVIO (vedolizumab) "Response" was clinical response, defined as reduction in complete Mayo score of ≥3 points and ≥30% from baseline with an accompanying decrease in rectal bleeding subscore of ≥1 point or absolute rectal bleeding subscore of ≤1 point (week 6 from UC Trial I; off treatment from UC Trial II). 4) The HUMIRA (adalimumab) "Response" was clinical response, defined as decrease in CDAI≥70 (week 4 and off treatment from CD-III trial).

Figure 1:
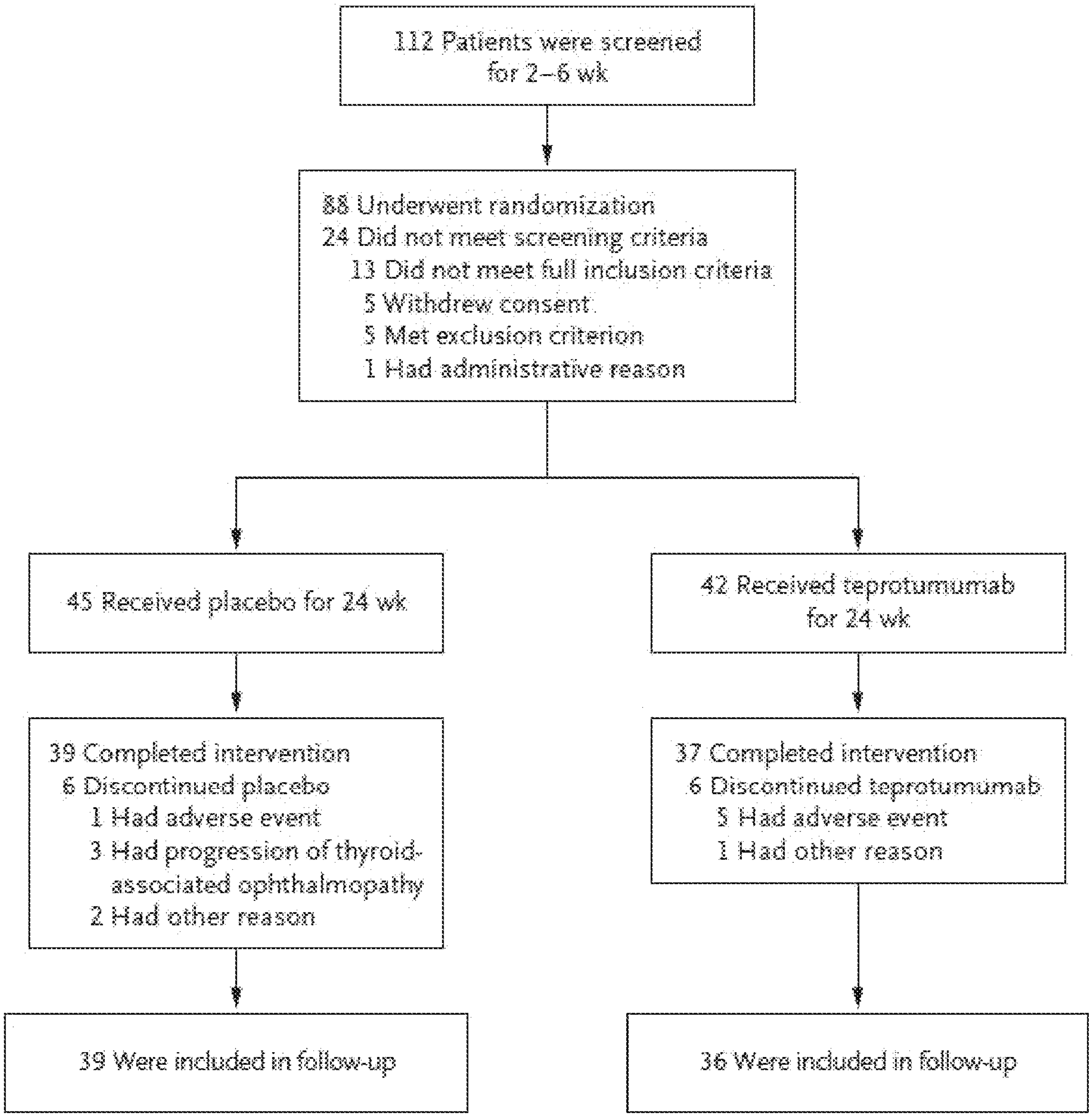
FIGS. 1-10 are from the Phase 2 study disclosed below in Example 1.

The Figures are discussed further below.

DETAILED DESCRIPTION

Certain antibodies are able to decrease TSHR and IGF-1R display by orbital fibroblasts and fibrocytes and attenuate the actions of IGF-1, TSH, thyroid-stimulating immunoglobulins, and immunoglobulins isolated from patients with GD and/or TED.

As described above, TED (TAO or GO) remains inadequately treated. Current medical therapies, which primarily consist of glucocorticoids, have limited efficacy and present safety concerns. It is well known that broad immunosuppressive treatments for TED, e.g. glucocorticoids and rituximab, cause a limited reduction in exophthalmos. In the largest RCT using three different cumulative doses of ivGCs (2.25 g, 4.98 g. 7.47 g of methylprednisolone), the mean reduction in proptosis was 0.6 mm, even using the highest dose. Results were not different using rituximab. Further, advanced cases of TED usually call for more invasive surgical treatment such as orbital decompression. Provided herein, is an extremely effective, significantly less invasive method of treating TED (TAO or GO) that also has an improved side effects profile.

Until the present disclosure, therapies for the treatment of TED (TAO or GO) had, as stated above, not only limited efficacy, but also safety concerns. As stated by one of skill in the art, "[t]he most striking and unexpected effect of [the methods disclosed herein] is the treatment-related decrease in exophthalmos [i.e., proptosis]. It is well known that immunosuppressive treatments for GO cause a limited reduction in exophthalmos, [but with the methods disclosed herein] exophthalmos decreased by an average of 2.46 mm (vs. 0.15 mm in the placebo group), . . . . These results, never achieved with whatsoever medical treatment, are comparable to those obtained with orbital decompression" (Piantanida, E. and Bartalena, L. *J Endocrinol Invest,* 2017, 40, 885-887).

Accordingly, provided herein is a method of reducing proptosis by at least 2 mm and reducing the clinical activity score (CAS) in a subject with TED (TAO or GO). The method comprises administering to the subject an effective amount of an antibody, or an antigen binding fragment thereof, wherein the antibody specifically binds to and inhibits IGF-1R (e.g., teprotumumab).

Also provided herein is a method of treating or reducing the severity of TED (TAO or GO). The method comprises administering to a subject in need thereof, an effective amount of an antibody, or an antigen binding fragment thereof, wherein the antibody specifically binds to and inhibits IGF-1R (e.g., teprotumumab), and wherein the antibody (i) reduces proptosis by at least 2 mm; and (ii) reduces the CAS in the subject by at least 2 points (on the 7-point version of the scale).

In some embodiments, the reduction in proptosis or exophthalmos could be greater than 2 mm, for example, 2.2 mm, 2.4 mm, 2.5 mm, 2.6 mm. 2.8 mm, 3 mm, 3.2 mm, 3.4 mm, 3.5 mm, 3.6 mm, 3.8 mm, 4 mm, 4.1 mm, 4.2 mm, 4.3 mm, 4.4 mm, 4.5 mm, 4.6 mm, 4.7 mm, 4.8 mm, 4.9 mm, 5 mm or more than 5 mm.

In some embodiments, the reduction in CAS is by 2 points or more, for example, by 3, 4, 5, 6, or 7 points. In one embodiment, the reduction in CAS is by 2 or more points. In another embodiment, it is by 3 or more points. In yet another embodiment, the reduction in CAS is by 4 or more points.

Also provided herein is a method of reducing proptosis by at least 4 mm in a subject with TED (TAO or GO). The method comprises administering to the subject an effective amount of an antibody, or an antigen binding fragment thereof, wherein the antibody specifically binds to and inhibits IGF-1R (e.g., teprotumumab).

Also provided herein is a method of treating or reducing the severity of TED. The method comprises administering to a subject in need thereof an effective amount of an antibody, or an antigen binding fragment thereof, wherein the antibody specifically binds to and inhibits IGF-1R (e.g., teprotumumab), and wherein the antibody reduces proptosis or exophthalmos by at least 3 mm. Also provided herein is a method of treating or reducing the severity of TED. The method comprises administering to a subject in need thereof, an effective amount of an antibody, or an antigen binding fragment thereof, wherein the antibody specifically binds to and inhibits IGF-1R (e.g., teprotumumab), and wherein the antibody reduces proptosis or exophthalmos by at least 4 mm.

Also provided herein is a method of treating or reducing the severity of diplopia associated with TED (in a subject with TED and diplopia), comprising administering to the subject, an effective amount of an antibody, or an antigen binding fragment thereof, wherein the antibody specifically binds to and inhibits IGF-1R (e.g., teprotumumab).

Also provided herein is a method of treating or reducing the severity of diplopia in a subject with thyroid eye disease (TED), comprising administering to the subject an effective amount of an antibody, or an antigen binding fragment thereof, wherein the antibody specifically binds to and inhibits IGF-1R (e.g., teprotumumab).

When TED is severe, this active autoimmune disease, characterized by orbital tissue remodeling from activation of TSH and IGF-1 receptors, results in excess extracellular matrix and proptosis/diplopia, a major quality of life (QoL) issue for TED patients. The severity and long-term diplopia response from a masked, placebo-controlled trial of teprotumumab in TED are presented herein, and the results showed that diplopia improved relative to placebo and was sustained out to 51 weeks after drug discontinuation.

Accordingly, also provided herein is a method of treating or reducing the severity of constant diplopia (CD) in a subject with thyroid eye disease (TED), comprising administering to the subject, an effective amount of an antibody, or an antigen binding fragment thereof, wherein the antibody specifically binds to and inhibits IGF-IR (e.g., teprotumumab). In some embodiments, the with teprotumumab to improve the CD QOL in patients with severe TED. Also provided herein is a method of treatment of diplopia comprising administering to the subject, an effective amount of an antibody, or an antigen binding fragment thereof, wherein the antibody specifically binds to and inhibits IGF-1R (e.g., teprotumumab), that results in improved diplopia relative to placebo which is sustained out to 51 weeks after drug discontinuation.

It should be noted that not all subjects respond to administration of the antibody, or an antigen binding fragment thereof, in the same manner. When administered to a population of patients, about 20%, 25%, 30%, 35%, 40%, 45%, 50%, 55%, 60%, 65%, 70%, 75%, 80%, 85%, 90%, 95% or 100% of the patients may respond with a reduction in proptosis or exophthalmos by at least 2 mm, a reduction in the CAS of at least 2 points, an improvement in quality of life as measured by the GO-QOL or either the functioning or appearance subscale thereof or any individual measure thereof, a reduction in diplopia or the severity of diplopia or constant diplopia, or any combination of the foregoing measures. In some embodiments, the response is seen in at least 20%, or at least 25%, or at least 30%, or at least 35%, or at least 40%, or at least 45%, or at least 50%, or at least 55%, or at least 60%, or at least 65%, or at least 70%, or at least 80% of the patients.

In some embodiments, the antibody, or an antigen binding fragment thereof, reduces proptosis by at least 3 mm in at least 25%, 30%, 35%, 40%, 45%50%, 55%, 60%, 65%, 70%, 75%, 80%, or 85% of the subjects. In some embodiments, the antibody, or an antigen binding fragment thereof, reduces proptosis by at least 3.5 mm in at least 25%, 30%, 35%, 40%, 45% 50%, 55%, 60%, 65%, 70%, 75%, 80%, or 85% of the subjects. In some embodiments, the antibody, or an antigen binding fragment thereof, reduces proptosis by at least 4 mm in at least 25%, 30%, 35%, 40%, 45%50%, 55%, 60%, 65%, 70%, 75%, 80%, or 85% of the subjects. In some embodiments, the antibody, or an antigen binding fragment thereof, reduces proptosis by at least 4 mm in about 40% of the subjects.

The antibody, or an antigen binding fragment thereof, can be administered in a single dose or in multiple doses. In one embodiment, the therapeutic antibody is administered to the subject in a single dose. In another embodiment, the therapeutic antibody is administered to the subject in multiple doses, spread out over the course of a few days, weeks or months. In some embodiments the antibody, or an antigen binding fragment thereof, is administered every week or every 2 weeks or every 3 weeks or every 4 weeks or every 5 weeks or every 6 weeks or every 7 weeks or every 8 weeks or every month or every 2 months or every 3 months.

In some embodiments the antibody, or an antigen binding fragment thereof, is administered in multiple doses and the dosage is the same each time. In some embodiments the antibody, or an antigen binding fragment thereof, is administered in multiple doses and the dosage at the time of first administration is different (could be higher or lower) from those at subsequent times. In some embodiments the antibody, or an antigen binding fragment thereof, is administered in multiple doses and the dosage is adjusted at each administration based on the subject's response to the therapy.

The dosage may further vary between patients, based on different factors such as the age, gender, race, and body weight of each patient. In one embodiment, the dosage varies by body weight of the patient. The dosage could range from about 1 mg of the antibody, or an antigen binding fragment thereof, per kilogram of body weight to about 100 mg of the antibody, or an antigen binding fragment thereof, per kilogram of body weight. The dosage, could for example, be 1 mg, 2 mg, 3 mg, 5 mg, 7 mg, 10 mg, 12 mg, 15 mg, 17 mg, 20 mg, 22 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg, of the antibody, or an antigen binding fragment thereof, per kilogram of body weight.

In some embodiments, the dosage is about 1 mg/kg to about 5 mg/kg of the antibody, or an antigen binding fragment thereof. In some embodiments, the dosage is about 5 mg/kg to about 10 mg/kg of the antibody, or an antigen binding fragment thereof. In some embodiments, the dosage is about 10 mg/kg to about 15 mg/kg of the antibody, or an antigen binding fragment thereof. In some embodiments, the dosage is about 15 mg/kg to about 20 mg/kg of the antibody, or an antigen binding fragment thereof.

In some embodiments where the antibody, or an antigen binding fragment thereof, is administered in multiple doses and the dosage at the time of first administration is different from those at subsequent times, the dosage at the time of first administration is about 1 mg/kg to about mg/kg of the antibody, or an antigen binding fragment thereof; or about 5 mg/kg to about mg/kg of the antibody, or an antigen binding fragment thereof; or about 10 mg/kg to about mg/kg of the antibody, or an antigen binding fragment thereof; or about 15 mg/kg to about mg/kg of the antibody, or an antigen binding fragment thereof; or about 20 mg/kg to about mg/kg of the antibody, or an antigen binding fragment thereof. The subsequent dose(s) could be higher or lower than the first dose. In some embodiments, the subsequent dose is about 1 mg/kg to about 5 mg/kg of the antibody, or an antigen binding fragment thereof; or about 5 mg/kg to about 10 mg/kg of the antibody, or an antigen binding fragment thereof; or about 10 mg/kg to about 15 mg/kg of the antibody, or an antigen binding fragment thereof; or about 15 mg/kg to about 20 mg/kg of the antibody, or an antigen binding fragment thereof; or about 20 mg/kg to about 25 mg/kg of the antibody, or an antigen binding fragment thereof.

The duration of the treatment would depend on the subject's response to the therapy and can range from about one month or 4 weeks to about 2 years or 100 weeks. In different embodiments, the treatment may be provided over a total duration of about 1 month, 2 months, 3 months, 4 months, 5 months, 6 months, 7 months, 8 months, 9 months, 10 months, 11 months, 1 year, 14 months, 16 months, 18 months, 20 months, 22 months or 2 years. In other embodiments, the treatment may be provided over a total duration of 4, 6, 8, 10, 12, 14, 16, 20, 22, 24, 26, 28, 30, 32, 34, 36, 38, 40, 42, 44, 46, 48, 50, 52 weeks, or extended to 56, 64, 72, 80, 88, 96 or 104 weeks.

In one embodiment, the antibody, or an antigen binding fragment thereof, is administered for a duration of 24 weeks at intervals of 3 weeks starting with an initial dose of 10 mg per kilogram of body weight, followed by 20 mg per kilogram for seven additional infusions.

The antibody, or an antigen binding fragment thereof, may be administered by any suitable route including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions disclosed herein. Typically, the therapeutic antibody may be prepared as a freeze-dried (lyophilized) powder or as an injectable, either as a liquid solution or suspension. Solid forms suitable for solution in, or suspension in, liquid vehicles prior to injection may also be used.

Enumerated Embodiments

Provided herein are the following specific embodiments.

Provided as Embodiment 1 is a method of a) reducing proptosis by at least 2 mm and/or b) reducing the clinical activity score (CAS) in a subject with thyroid eye disease (TED), comprising administering to the subject an effective amount of an antibody, or an antigen binding fragment thereof, wherein the antibody specifically binds to and inhibits insulin like growth factor-I receptor (IGF-1R).

Embodiment 2: The method of Embodiment 1, wherein CAS is reduced by at least 2 points.

Embodiment 3: The method of Embodiment 1, wherein proptosis is reduced by at least 3 mm and CAS is reduced by at least 3 points.

Embodiment 4: The method of Embodiment 3, wherein proptosis is reduced by at least 4 mm in at least 40% of the subjects.

Provided as Embodiment 5 is a method of reducing proptosis by at least 4 mm in a subject with TED, comprising administering to the subject an effective amount of an antibody, or an antigen binding fragment thereof, wherein the antibody specifically binds to and inhibits IGF-1R.

Provided as Embodiment 6 is a method of treating or reducing the severity of diplopia in a subject with thyroid eye disease (TED), comprising administering to the subject an effective amount of an antibody, or an antigen binding fragment thereof, wherein the antibody specifically binds to and inhibits IGF-1R.

Embodiment 7: The method of Embodiment 6, wherein the diplopia is constant diplopia.

Embodiment 8: The method of Embodiment 6, wherein the diplopia is inconstant diplopia.

Embodiment 9: The method of Embodiment 6, wherein the diplopia is intermittent diplopia.

Embodiment 10: The method of any of Embodiments 6-9 wherein the improvement in or reduction in severity of diplopia is sustained at least 20 weeks after discontinuation of antibody administration.

Embodiment 11: The method of any of Embodiments 6-9 wherein the improvement in or reduction in severity of diplopia is sustained at least 40 weeks after discontinuation of antibody administration.

Embodiment 12: The method of any of Embodiments 6-9 wherein the improvement in or reduction in severity of diplopia is sustained at least 20 weeks after discontinuation of antibody administration.

Provided as Embodiment 13 is a method of reducing the Clinical Activity Score (CAS) in a subject with thyroid eye disease (TED) to 0 or 1, comprising administering to the subject an effective amount of an antibody, or an antigen binding fragment thereof, wherein the antibody specifically binds to and inhibits IGF-1R.

Embodiment 14: The method of Embodiment 13, comprising administering to the subject the effective amount of the antibody, or antigen binding fragment thereof, for a period of at least 12 weeks.

Embodiment 15: The method of Embodiment 13, comprising administering to the subject the effective amount of the antibody, or antigen binding fragment thereof, for a period of at least 18 weeks.

Embodiment 16: The method of Embodiment 13, comprising administering to the subject the effective amount of the antibody, or antigen binding fragment thereof, for a period of at least 24 weeks.

Provided as Embodiment 17 is a method of improving the visual functioning of a subject with thyroid eye disease (TED) by at least 8 points, comprising administering to the subject an effective amount of an antibody, or an antigen binding fragment thereof, wherein the antibody specifically binds to and inhibits IGF-1R.

Embodiment 18: The method of Embodiment 17, wherein the visual functioning is measured by the Graves' Ophthalmopathy Quality of Life (GO-QOL) visual functioning subscale.

Provided as Embodiment 19 is a method of improving the visual appearance of a subject with thyroid eye disease (TED) by at least 8 points, comprising administering to the subject an effective amount of an antibody, or an antigen binding fragment thereof, wherein the antibody specifically binds to and inhibits IGF-1R.

Embodiment 20: The method of Embodiment 19, herein the visual functioning is measured by the Graves' Ophthalmopathy Quality of Life (GO-QOL) visual appearance subscale.

Provided as Embodiment 21 is a method of treating or reducing the severity of diplopia in a subject with thyroid eye disease (TED), comprising administering to the subject an effective amount of an antibody, or an antigen binding fragment thereof, wherein the antibody specifically binds to and inhibits IGF-1R.

Embodiment 22: The method of Embodiment 21, wherein the diplopia is constant diplopia.

Embodiment 23: The method of Embodiment 22, wherein the improvement in or reduction in severity of diplopia is sustained at least 20 weeks after discontinuation of antibody administration.

Embodiment 24: The method of Embodiment 22, wherein the improvement in or reduction in severity of diplopia is sustained at least 40 weeks after discontinuation of antibody administration.

Embodiment 25: The method of Embodiment 22, wherein the improvement in or reduction in severity of diplopia is sustained at least 50 weeks after discontinuation of antibody administration.

Embodiment 26: The method of Embodiment 21, wherein the diplopia is inconstant diplopia.

Embodiment 27: The method of Embodiment 21, wherein the diplopia is intermittent diplopia.

Embodiment 28: The method of any one of Embodiments 1-27, wherein the antibody is administered at a dosage of about 1 mg/kg to about 5 mg/kg antibody as a first dose.

Embodiment 29: The method of any one of Embodiments 1-27, wherein the antibody is administered at a dosage of about 5 mg/kg to about 10 mg/kg antibody as a first dose.

Embodiment 30: The method of either of Embodiments 28 and 29, wherein the antibody is administered at a dosage of about 5 mg/kg to about 20 mg/kg antibody in subsequent doses.

Embodiment 31: The method of any one of Embodiments 1-30, wherein the antibody is administered in the following amounts:

about 10 mg/kg antibody as a first dose; and about 20 mg/kg antibody in subsequent doses.

Provided as Embodiment 32 is a method of treatment of thyroid eye disease (TED), comprising administering to a subject in need thereof an antibody, or an antigen binding fragment thereof, wherein the antibody specifically binds to and inhibits IGF-1R, wherein the antibody is administered in the following amounts:

about 10 mg/kg antibody as a first dose; and about 20 mg/kg antibody in subsequent doses.

Embodiment 33: The method of any of Embodiments 30, 31, and 32, wherein the subsequent doses are administered every three weeks for at least 21 weeks.

Embodiment 34: The method of any one of Embodiments 1-33, wherein the antibody, or an antigen binding fragment thereof, has a binding affinity ($K_D$) of $10^{-8}$ M or less for the IGF-1R.

Embodiment 35: The method of any one of Embodiments 1-33, wherein the antibody, or an antigen binding fragment thereof, has a binding affinity ($K_D$) of $10^{-13}$ to $10^{-9}$ M for the IGF-1R.

Embodiment 36: The method of any one of Embodiments 1-33, wherein the antibody, or an antigen binding fragment thereof, has an $IC_{50}$ values for the binding of IGF-I and IGF-II to IGF-1R of no more than about 2 nM.

Embodiment 37: The method of any one of Embodiments 1-36, wherein the antibody, or an antigen binding fragment thereof, comprises a heavy chain comprising CDR1, CDR2 and CDR3 and a light chain comprising CDR1, CDR2 and CDR3, wherein the heavy chain CDR1, CDR2, and CDR3 amino acid sequences and light chain CDR1, CDR2, and CDR3 amino acid sequences are at least 90% identical to (i) the amino acid sequences of SEQ ID NOs: 1-6, respectively; or (ii) the amino acid sequences of SEQ ID NOs: 1, 9, 3, 4, 10, 6, respectively.

Embodiment 38: The method of any one of Embodiments 1-36, wherein the antibody, or an antigen binding fragment thereof, comprises:

(i) heavy chain CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively.

Embodiment 39: The method of either of Embodiments 37 or 38, wherein the antibody, or an antigen binding fragment thereof, comprises:

(i) a heavy chain variable region having at least 80% sequence identity to the amino acid sequence of SEQ ID NO: 7 and a light chain variable region having at least 80% sequence identity to the amino acid sequence of SEQ ID NO: 8; or (ii) a heavy chain variable region having at least 80% sequence identity to the amino acid sequence of SEQ ID NO: 11 and a light chain variable region having at least 80% sequence identity to the amino acid sequence of SEQ ID NO: 12.

Embodiment 40: The method of Embodiment 39, wherein the antibody, or an antigen binding fragment thereof, comprises:

(i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12.

Embodiment 41: The method of any one of Embodiments 1-40, wherein the antibody is antibody 1 or antibody 2, or an antigen binding fragment thereof.

Embodiment 42: The method of any one of Embodiments 1-41, wherein the antibody is teprotumumab.

Embodiment 43: The method of any one of Embodiments 1-42, wherein the antibody, or an antigen binding fragment thereof, is a human antibody, a monoclonal antibody, a human monoclonal antibody, a purified antibody, a diabody, a single-chain antibody, a multi-specific antibody, Fab, Fab', F(ab')2, Fv or scFv.

Embodiment 44: The method of any one of Embodiments 1-43, wherein the antibody, or an antigen binding fragment thereof, is administered in a pharmaceutical composition that additionally comprises a pharmaceutically acceptable diluent or excipient or carrier.

Embodiment 45: The method of Embodiment 44, wherein the pharmaceutical composition further comprises one or more pharmaceutically active compounds for the treatment of TED.

Embodiment 46: The method of Embodiment 45, wherein the pharmaceutical composition further comprises corticosteroids; rituximab or other anti-CD20 antibodies; tocilizumab or other anti-IL-6 antibodies; or selenium, infliximab or other anti-TNFα antibodies or a thyroid-stimulating hormone receptor (TSHR) inhibitor.

Embodiment 47: The method of any one of Embodiments 1-46, wherein the treatment is efficacious for at least 4 weeks beyond the last administered dose.

Embodiment 48: The method of any one of Embodiments 1-46, wherein the treatment is efficacious for at least 6 weeks beyond the last administered dose.

Embodiment 49: The method of any one of Embodiments 1-46, wherein the treatment is efficacious for at least 8 weeks beyond the last administered dose.

Embodiment 50: The method of any one of Embodiments 1-36, wherein the treatment is efficacious for at least 20 weeks beyond the last administered dose.

The embodiments above are also provided for treatment of patients who do not initially respond to a first course of treatment, or respond but later relapse.

Embodiment 51. A method of treating or reducing the severity of thyroid eye disease (TED), or a symptom thereof, comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR.

Embodiment 52. A method of reducing proptosis in an eye in a subject with thyroid eye disease (TED) who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to said subject an effective amount of the antibody, or an antigen binding fragment thereof, wherein said antibody specifically binds to and inhibits insulin like growth factor-I receptor (IGF-IR).

Embodiment 53. A method of reducing Clinical Activity Score (CAS) of thyroid eye disease (TED) in a subject who has undergone prior treatment with an antibody, or an antigen binding fragment thereof, that specifically binds to and inhibits IGF-IR, and either did not respond to said prior treatment or relapsed after said prior treatment, comprising administering to a subject in need thereof an effective amount of an antibody, or an antigen binding fragment thereof, wherein said antibody specifically binds to and inhibits IGF-IR.

Embodiment 54. A method of a) reducing proptosis by at least 2 mm and b) reducing the clinical activity score (CAS) in a subject with thyroid eye disease (TED) who has previously undergone prior treatment with an antibody, or an antigen binding fragment thereof, that specifically binds to and/or inhibits insulin like growth factor-I receptor (IGF-IR) and either did not respond to said prior treatment or responded to said prior treatment and later relapsed, comprising administering to the subject an effective amount of an antibody, or an antigen binding fragment thereof, wherein the antibody specifically binds to and inhibits insulin like growth factor-I receptor (IGF-IR).

Embodiment 55. The method of any of Embodiments 51, 52, and 54, wherein proptosis is reduced by at least 2 mm.

Embodiment 56. The method of Embodiment 55, wherein proptosis is reduced by at least 3 mm.

Embodiment 57. The method of Embodiment 55, wherein proptosis is reduced by at least 4 mm.

Embodiment 58. The method of any of Embodiments 51, 53, and 54, wherein the clinical activity score (CAS) of the subject is reduced by at least 2 points.

Embodiment 59. The method of Embodiment 58, wherein the clinical activity score (CAS) of the subject is reduced to one (1).

Embodiment 60. The method of Embodiment 59, wherein the clinical activity score (CAS) of the subject is reduced to zero (0).

Embodiment 61. A method of treating or reducing the severity of thyroid eye disease (TED) in a subject who has undergone prior treatment with an antibody, or an antigen binding fragment thereof, that specifically binds to and/or inhibits insulin like growth factor-I receptor (IGF-IR) and either did not respond to said prior treatment or relapsed after said prior treatment comprising administering to a subject in need thereof an effective amount of an antibody, or an antigen binding fragment thereof, wherein said antibody specifically binds to and inhibits IGF-IR, and wherein treatment with said antibody (i) reduces proptosis by at least 2 mm in an eye; (ii) is not accompanied by a deterioration of 2 mm or more in the other (or fellow eye); and (iii) reduces the CAS in said subject to either one (1) or zero (0).

Embodiment 62. A method of improving the quality of life in a subject with thyroid eye disease (TED) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

Embodiment 63. The method of Embodiment 62, wherein the quality of life is measured by the Graves' Ophthalmopathy Quality of Life (GO-QoL) assessment, or either the Visual Functioning or Appearance subscale thereof.

Embodiment 64. The method of Embodiment 63, wherein the treatment results in an improvement of ≥8 points on the GO-QoL.

Embodiment 65. The method of Embodiment 64, wherein the treatment results in an improvement on the Functioning subscale of the GO-QoL.

Embodiment 66. The method of Embodiment 64, wherein the treatment results in an improvement on the Appearance subscale of the GO-QoL.

Embodiment 67. A method of treating or reducing the severity of diplopia in a subject with thyroid eye disease (TED) who has undergone prior treatment with an antibody, or an antigen binding fragment thereof, that specifically binds to and inhibits IGF-IR, and either did not respond to said prior treatment or responded to said prior treatment and later relapsed, comprising administering to the subject an effective amount of an antibody, or an antigen binding fragment thereof, wherein the antibody specifically binds to and inhibits IGF-IR.

Embodiment 68. The method of Embodiment 67, wherein the diplopia is constant diplopia.

Embodiment 69. The method of Embodiment 67, wherein the diplopia is inconstant diplopia.

Embodiment 70. The method of Embodiment 67, wherein the diplopia is intermittent diplopia.

Embodiment 71. The method of Embodiment 67, wherein the improvement in or reduction in severity of diplopia is sustained at least 20 weeks after discontinuation of antibody administration.

Embodiment 72. The method of Embodiment 67, wherein the improvement in or reduction in severity of diplopia is sustained at least 50 weeks after discontinuation of antibody administration.

Embodiment 73. The method of any one of Embodiments 51-52, wherein said antibody is administered at a dosage of about 1 mg/kg to about 5 mg/kg antibody as a first dose.

Embodiment 74. The method of any one of Embodiments 51-52, wherein said antibody is administered at a dosage of about 5 mg/kg to about 10 mg/kg antibody as a first dose.

Embodiment 75. The method of any one of Embodiments 51-52, wherein said antibody is administered at a dosage of about 5 mg/kg to about 20 mg/kg antibody in subsequent doses.

Embodiment 76. The method of any one of Embodiments 51-52, wherein said antibody is administered in the following amounts: about 10 mg/kg antibody as a first dose; and about 20 mg/kg antibody in subsequent doses.

Embodiment 77. The method of Embodiment 76, wherein said subsequent doses are administered every three weeks for at least 21 weeks.

Embodiment 78. The method of any one of Embodiments 51-57, wherein the antibody, or an antigen binding fragment thereof, comprises a heavy chain comprising CDR1, CDR2 and CDR3 and a light chain comprising CDR1, CDR2 and CDR3, wherein the heavy chain CDR1, CDR2, and CDR3 amino acid sequences and light chain CDR1, CDR2, and CDR3 amino acid sequences are at least 90% identical to (i) the amino acid sequences of SEQ ID NOs: 1-6, respectively; or (ii) the amino acid sequences of SEQ ID NOs: 1, 9, 3, 4, 10, 6, respectively.

Embodiment 79. The method of any one of Embodiments 51-57, wherein the antibody, or an antigen binding fragment thereof, comprises: (i) heavy chain CDR1, CDR2, and CDR3 amino acid sequences and light chain CDR1, CDR2, and CDR3 amino acid sequences as set forth in SEQ ID NOs: 1-6, respectively; or (ii) heavy chain CDR1, CDR2, and CDR3 amino acid sequences and light chain CDR1, CDR2, and CDR3 amino acid sequences as set forth in SEQ ID NOs: 1, 9, 3, 4, 10, 6, respectively.

Embodiment 80. The method of Embodiment 78 or 79, wherein the antibody, or an antigen binding fragment thereof, comprises: (i) a heavy chain variable region having at least 80% sequence identity to the amino acid sequence of SEQ ID NO: 7 and a light chain variable region having at least 80% sequence identity to the amino acid sequence of SEQ ID NO: 8; or (ii) a heavy chain variable region having at least 80% sequence identity to the amino acid sequence of SEQ ID NO: 11 and a light chain variable region having at least 80% sequence identity to the amino acid sequence of SEQ ID NO: 12.

Embodiment 81. The method of Embodiment 80, wherein the antibody, or an antigen binding fragment thereof, comprises: (i) a heavy chain variable region comprising the amino acid sequence of SEQ ID NO: 7 and a light chain variable region comprising the amino acid sequence of SEQ ID NO: 8; or (ii) a heavy chain variable region comprising the amino acid sequence of SEQ ID NO: 11 and a light chain variable region comprising the amino acid sequence of SEQ ID NO: 12.

Embodiment 82. The method of any one of Embodiments 51-78, wherein the antibody is antibody 1 or antibody 2, or an antigen binding fragment thereof.

Embodiment 83. The method of any one of Embodiments 51-78, wherein the antibody, or an antigen binding fragment thereof, is a human antibody, a monoclonal antibody, a human monoclonal antibody, a purified antibody, a diabody, a single-chain antibody, a multi-specific antibody, Fab, Fab', F(ab')2, Fv or scFv.

Embodiment 84. The method of any one of Embodiments 51-78, wherein the antibody, or an antigen binding fragment thereof, is administered in a pharmaceutical composition that additionally comprises a pharmaceutically acceptable diluent or excipient or carrier.

Embodiment 85. The method of Embodiment 84, wherein the pharmaceutical composition further comprises one or more pharmaceutically active compounds for the treatment of TED.

Embodiment 86. The method of Embodiment 84 or 85, wherein the pharmaceutical composition further comprises corticosteroids; rituximab or other anti-CD20 antibodies; tocilizumab or other anti-IL-6 antibodies; or selenium, infliximab or other anti-TNFα antibodies or a thyroid-stimulating hormone receptor (TSHR) inhibitor.

Embodiment 87. A method of treating or reducing the severity of thyroid eye disease (TED) comprising administering to a subject who has undergone prior treatment with an antibody, or an antigen binding fragment thereof, that specifically binds to and inhibits IGF-IR, and either did not respond to said prior treatment or responded to said prior treatment and later relapsed, the antibody, or an antigen binding fragment thereof, wherein said antibody specifically binds to and inhibits IGF-IR, wherein the antibody is administered in the following amounts:

about 10 mg/kg antibody as a first dose; and about 20 mg/kg antibody in subsequent doses.

Embodiment 88. The method of Embodiment 87, wherein said subsequent doses are administered every three weeks for at least 21 weeks.

Embodiment 89. The method of Embodiment 88, wherein the antibody is teprotumumab, or an antigen binding fragment thereof.

Embodiment 90. The method of Embodiment 89, wherein the antibody or antigen binding fragment thereof is administered by injection.

Also provided are embodiments wherein any embodiment herein may be combined with any one or more of other embodiments disclosed herein, provided the combination is not mutually exclusive. As used herein, two embodiments are "mutually exclusive" when one is defined to be something which is different than the other. The choice not to claim any particular embodiment at application filing or during pendency does not constitute a disclaimer of the embodiment for purposes of amending claims or pursuing continuing applications.

Abbreviations and Definitions

The following terms shall be understood to have the meanings ascribed herein.

As used herein, "Thyroid-associated Ophthalmopathy" (TAO), "Thyroid Eye Disease" (TED), "Thyroid Inflammatory Eye Disease (TIED)," "Graves' Ophthalmopathy" (GO) or "Graves' Orbitopathy" (GO) refer to the same disorder or condition and are used interchangeably. They all refer to the inflammatory orbital pathology associated with some autoimmune thyroid disorders, most commonly with "Graves' Disease" (GD), but sometimes with other diseases, e.g. Hashimoto's thyroiditis.

The terms "proptosis" and "exophthalmos" (also known as exophthalmus, exophthalmia, or exorbitism) refer to the forward projection, displacement, bulging, or protrusion of an organ. As used herein, the terms refer to the forward projection, displacement, bulging, or protrusion of the eye anteriorly out of the orbit. Proptosis and exophthalmos are considered by some of skill in the art to have the same meaning and are often used interchangeably, while others attribute subtle differences to their meanings. Exophthalmos is used by some to refer to severe proptosis; or to refer to endocrine-related proptosis. Yet others use the term exophthalmos when describing proptosis associated with the eye, in, for example, subjects with thyroid eye disease (TED; GO or TAO).

As used herein, the terms "proptosis" and "exophthalmos" are used interchangeably and refer to the forward projection, displacement, bulging, or protrusion of the eye anteriorly out of the orbit. Owing to the rigid bony structure of the orbit with only anterior opening for expansion, any increase in orbital soft tissue contents taking place from the side or from behind will displace the eyeball forward. Proptosis or exophthalmos can be the result of a several disease processes including infections, inflammations, tumors, trauma, metastases, endocrine lesions, vascular diseases & extra orbital lesions. Thyroid eye disease (TED; GO or TAO) is currently recognized as the most common cause of proptosis in adults. Exophthalmos can be either bilateral, as is often seen in thyroid eye disease (TED; GO or TAO), or unilateral (as is often seen in an orbital tumor).

Measurement of the degree of exophthalmos can be performed using an exophthalmometer, an instrument used for measuring the degree of forward displacement of the eye. The device allows measurement of the forward distance of the lateral orbital rim to the front of the cornea.

Computed tomography (CT) scanning and Magnetic resonance imaging (MRI) may also be used in evaluating the degree of exophthalmos or proptosis. CT scanning is an excellent imaging modality for the diagnosis of TAO. In addition to allowing visualization of the enlarged extraocular muscles, CT scans provide the surgeon or clinician with depictions of the bony anatomy of the orbit when an orbital decompression is required. MRI, with its multi-planar and inherent contrast capabilities, provides excellent imaging of the orbital contents without the radiation exposure associated with CT scan studies. MRI provides better imaging of the optic nerve, orbital fat, and extraocular muscle, but CT scans provide better views of the bony architecture of the orbit.

Orbital ultrasonography can also be a used for the diagnosis and evaluation of TED, because it can be performed quickly and with a high degree of confidence. High reflectivity and enlargement of the extraocular muscles are assessed easily, and serial ultrasonographic examinations can also be used to assess progression or stability of the ophthalmopathy.

Based on the technologies currently available, or that will become available in the future, one of skill in the art would be capable of determining the best modality for diagnosing and evaluating the extent of proptosis or exophthalmos.

Although it is generally accepted that the normal range of proptosis is 12-21 mm, it must be noted that the value for a normal person varies by age, gender and race. For example, in normal adult white males, the average distance of globe protrusion is 16.5 mm, with the upper limit of normal at 21.7 mm. In adult African Americans it averages 18.2 mm, with an upper normal limit of 24.1 mm in males and 22.7 mm in females. In Mexican adults, males averaged 15.2 mm and females averaged 14.8 mm and in Iran, for the age group of 20-70 years, the average was 14.7 mm. In Taiwanese adults, comparing normal subjects to those with Graves' Ophthalmopathy, the normal group had an average reading of 13.9 mm versus 18.3 mm for the TED group.

Even within a group of people, there can be variability. Four ethnic groups in Southern Thailand had exophthalmometry measurement averages ranging from 15.4 mm to 16.6 mm. In 2477 Turkish patients, the median measurement was 13 mm, with an upper limit of 17 mm; and in a Dutch study, the upper limit was 20 mm in males and 16 mm in females.

Although the average and upper limits for exophthalmos or proptosis vary widely, it is accepted in the field that a difference greater than 2 mm between the eyes is significant and not normal.

One of skill in the art, for example an ophthalmologist, surgeon or other clinician skilled in the knowledge and treatment of eye disorders would know what a normal value of proptosis is based on the age, gender and race of the subject and have the ability to diagnose or evaluate the presence or absence of proptosis as well as track its progression.

Activity Measures and Assessments

Several classification systems have been conceived to assess the clinical manifestations of TED. In 1969, Werner reported the NOSPECS Classification (No physical signs or symptoms, Only signs, Soft tissue involvement, Proptosis, Extraocular muscle signs, Corneal involvement, and Sight loss) (Werner, S. C. *American Journal of Ophthalmology,* 1969, 68, no. 4, 646-648.)

The modified NOSPECS was also published by Werner in 1977 and has been broadly used since then (Werner, S. C. *American Journal of Ophthalmology,* 1977, 83, no. 5, 725-727). This classification grades for clinical severity and does not provide a means of distinguishing active TED (inflammatory progressive) from inactive TED (noninflammatory stationary). Therefore, the indication for treatments used to be based exclusively in the severity of symptoms without consideration whether the disease was active or inactive. In 1989, Mourits et al. described the Clinical Activity Score (CAS) (Mourits et al., *British Journal of Ophthalmology,* 1989, 73, no. 8, 639-644) as a way of assessing the degree of active disease. This score, based on the classical signs of acute inflammation (pain, redness, swelling, and impaired function) was proposed as a clinical classification to discriminate easily between active and inactive disease and was modified in 1997 (Mourits et al., *Clinical Endocrinology,* 1997. 47, no. 1, 9-14). This protocol is further described below.

As used herein, the term Clinical Activity Score (CAS) refers to the protocol described and scored as disclosed below. According to this protocol, one point is given for the presence of each of the parameters assessed in the Table below. The sum of all points defines clinical activity and provides the CAS. For patients assessed for the first time only items 1-7 are scored. A CAS≥3/7 indicates active TED. For patients that are assessed for the second or subsequent time (typically, 1-3 months later), items 8-10 are also scored; and a CAS≥4/10 indicates active disease. A ten-item CAS scale exists as well, but in clinical trials, the 7-item scale is generally used, being more amenable to longitudinal studies involving multiple assessments.

The CAS consists of seven components:

1. spontaneous retrobulbar pain,
2. pain on attempted eye movements (upward, side-to-side, and downward gazes),
3. conjunctival redness,
4. redness of the eyelids,
5. chemosis (conjunctival swelling/edema),
6. swelling of the caruncle/plica, and
7. swelling of the eyelids.

Each component is scored as present (1 point) or absent (0 points). The score at each efficacy assessment is the sum of all items present; giving a range of 0-7, where 0 or 1 constitutes inactive disease and 7 severe active ophthalmopathy. A change of >2 points is considered clinically meaningful.

Item 1, spontaneous orbital pain could be a painful, or oppressive feeling on, or behind, the globe. This pain may be caused by the rise in intraorbital pressure, when the orbital tissues volume increases through excess synthesis of extracellular matrix, fluid accumulation, and cellular infiltration and expansion. Item 2, gaze evoked orbital pain, could be pain in the eyes when looking, or attempting to look, up, down or sideways, i.e., pain with upward, downward, or lateral eye movement, or when attempting upward, downward, or lateral gaze. This kind of pain could arise from the stretching of the inflamed muscle(s), especially on attempted up-gaze. The 'stretching pain' cannot be provoked by digital pressing on the eyeball, as would be expected if it were a manifestation of the raised intraorbital pressure. Both kinds of pain can be reduced after anti-inflammatory treatment. These kinds of pain are therefore considered to be directly related to autoimmune inflammation in the orbit and thus useful in assessing TED activity.

Swelling in TED is seen as chemosis (edema of the conjunctiva), and swelling of the caruncule and/or plica semilunaris. Both are signs of TED activity. Swollen eyelids can be caused by edema, fat prolapse through the orbital septum, or fibrotic degeneration. In addition to swelling, other symptoms indicative of active TED include redness and/or pain of the conjunctiva, eyelid, caruncule and/or plica semilunaris.

Other grading systems have also been developed for the assessment of TED. The VISA Classification (vision, inflammation, strabismus, and appearance) (Dolman, P. J., and Rootman, J., *Ophthalmic Plastic and Reconstructive Surgery,* 2006, 22, no. 5, 319-324 and Dolman, P. J., *Best Practice & Research Clinical Endocrinology & Metabolism,* 2012, 26, no. 3, 229-248) and the European Group of Graves' Orbitopathy (EUGOGO) Classification (Bartalena, L., et al., *European Journal of Endocrinology,* 2008, 158, no. 3, 273-285) are two such examples. Both systems are grounded in the NO SPECS and CAS classifications and use indicators to assess the signs of activity and the degree of severity. More importantly, they allow the clinician to guide the treatment of the patient with GO. VISA is more commonly used in North America and Canada while EUGOGO is in Europe. Since the VISA and EUGOGO protocols are not interchangeable, only one of them should be employed as a reference in a specific patient.

In addition to proptosis (or exophthalmos) and CAS, quality of life (QoL) was also evaluated with the use of the Graves' ophthalmopathy quality of life (GO-QoL) questionnaire. This questionnaire is designed to determine the improved quality of life after treatment. In some embodiments, questionnaire may determine the decreased or lack of side effects after being treated with an antibody, or an antigen binding fragment thereof, according to the methods disclosed herein, as compared to treatment with glucocorticoids.

As described below, the questionnaire has two self-assessment subscales. The first relates to the impact of visual function on daily activities, while the second relates to the impact of self-perceived appearance. Each subscale has 8 questions which are answered with: (i) yes—very much so; (ii) yes—a little; or (iii) no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale is considered to be clinically meaningful. The combined score takes raw scores from both subscales and again transforms them to a single 0-100 scale.

Severity Measures

For lid aperture, the distance between the lid margins were measured (in mm) with the patient looking in the primary position, sitting relaxed, and with distant fixation. For swelling of the eyelids, the measure/evaluation was either "absent/equivocal," "moderate," or "severe." Redness of the eyelids was either absent or present. Redness of the conjunctivae was either absent or present. Conjunctival edema was either absent or present. Inflammation of the caruncle or plica was either absent or present. Exophthalmos was measured in millimeter using the same Hertel exophthalmometer and same intercanthal distance for an individual patient.

As described below, subjective diplopia was scored from 0 to 3 (0=no diplopia;

1=intermittent, i.e., diplopia in primary position of gaze, when tired or when first awakening;

2=inconstant, i.e., diplopia at extremes of gaze;

3=constant, i.e., continuous diplopia in primary or reading position).

For eye muscle involvement, the ductions were measured in degrees. Corneal involvement was either absent/punctate or keratopathy/ulcer. For optic nerve involvement, i.e., best-corrected visual acuity, color vision, optic disc, relative afferent pupillary defect, the condition was either absent or present. In addition, visual fields were checked if optic nerve compression was suspected.

Severity Classification

Sight-threatening thyroid eye disease: Patients with dysthyroid optic neuropathy (DON) and/or corneal breakdown. This category warranted immediate intervention.

Moderate-to-severe thyroid eye disease: Patients without sight-threatening disease whose eye disease had sufficient impact on daily life to justify the risks of immunosuppression (if active) or surgical intervention (if inactive). Patients with moderate-to-severe thyroid eye disease usually had any one or more of the following: lid retraction≥2 mm, moderate or severe soft tissue involvement, exophthalmos≥3 mm above normal for race and gender, inconstant or constant diplopia.

Mild thyroid eye disease: Patients whose features of thyroid eye disease have only a minor impact on daily life insufficient to justify immunosuppressive or surgical treatment. They usually have only one or more of the following: minor lid retraction (<2 mm), mild soft tissue involvement, exophthalmos<3 mm above normal for race and gender, transient or no diplopia, and corneal exposure responsive to lubricants.

To facilitate understanding of the disclosure, a number of terms and abbreviations as used herein are defined below as follows:

As used herein, the term "antibody" encompasses the various forms of antibodies including but not being limited to whole antibodies, monoclonal antibodies, antibody fragments, human antibodies, humanized antibodies, chimeric antibodies and genetically engineered antibodies as long as the characteristic properties such as specificity and IGF-1R inhibitory are retained.

As used herein, the terms "antigen binding fragment," "fragment," and "antibody fragment" are used interchangeably to refer to any fragment that comprises a portion of a full length antibody, generally at least the antigen binding portion or the variable region thereof. Examples of antibody fragments include, but are not limited to, diabodies, single-chain antibody molecules, multispecific antibodies, Fab, Fab', F(ab')2, Fv or scFv. Further, the term "antibody" as used herein includes both antibodies and antigen binding fragments thereof. In addition, antibody fragments comprise single chain polypeptides having the characteristics of a VH chain, namely being able to assemble together with a VL chain or of a VL chain binding to IGF-1R, namely being able to assemble together with a VH chain to a functional antigen binding pocket and thereby providing the property of inhibiting the binding of IGF-I and IGF-II to IGF-1R.

The terms "monoclonal antibody" or "monoclonal antibody composition," as used herein refer to a preparation of antibody molecules of a single amino acid composition. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light human chain transgene fused to an immortalized cell.

The term "human antibody" as used herein, is intended to include antibodies having variable and constant regions derived from human germline immunoglobulin sequences. The term "humanized antibody" as used herein refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody."

The term "recombinant human antibody," as used herein, is intended to include all human antibodies that are prepared, expressed, created or isolated by recombinant means, such as antibodies isolated from a host cell such as an SP2-0, NS0 or CHO cell or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a ß-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play an important role in the binding specificity/affinity of antibodies.

The terms "complementarity determining region," "CDR," "hypervariable region," or "antigen-binding portion of an antibody" are used interchangeably herein and refer to the amino acid residues of an antibody which are responsible for antigen-binding. The hypervariable region comprises amino acid residues from the complementarity determining regions or CDRs. "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, MD. (1991)) and/or those residues from a "hypervariable loop."

The terms "binding to IGF-IR" or "specific binding to IGF-IR" are used interchangeably herein and mean the binding of the antibody to IGF-IR in an in vitro assay, preferably in a binding assay in which the antibody is bound to a surface and binding of IGF-IR is measured by Surface Plasmon Resonance (SPR). Binding means a binding affinity ($K_D$) of $10^{-8}$ M or less, preferably $10^{-13}$ to $10^{-9}$ M. Binding to IGF-IR can be investigated by a BIAcore assay (Pharmacia Biosensor AB, Uppsala, Sweden). The affinity of the binding is defined by the terms ka (rate constant for the association of the antibody from the antibody/antigen complex), kd (dissociation constant), and $K_D$ (kd/ka). The antibodies used in the methods disclosed herein typically show a $K_D$ of about $10^{-9}$ M or less.

The antibodies, or antigen binding fragments thereof, used in the methods disclosed herein inhibit the binding of IGF-I and IGF-II to IGF-IR. The inhibition is measured as $IC_{50}$ in an assay for binding of IGF-I/IGF-II to IGF-1R on cells. Such an assay is known to one of skill in the art and is described, for example, U.S. Pat. No. 7,579,157, which is incorporated herein in its entirety. The $IC_{50}$ values of the antibodies used in the methods disclosed herein for the binding of IGF-I and IGF-II to IGF-1R typically are no more than 2 nM. $IC_{50}$ values are measured as average or median values of at least three independent measurements. Single $IC_{50}$ values may be excluded from the scope.

The term "inhibiting the binding of IGF-I and IGF-II to IGF-1R" as used herein refers to inhibiting the binding of $I^{125}$-labeled IGF-I or IGF-II to IGF-1R presented on the surface of cells in an in vitro assay. Inhibiting means an $IC_{50}$ value of 2 nM or lower.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

The terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient, in certain embodiments, is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression, for example from inactive TED to active TED. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the subject or patient is a human.

As used herein, the "study eye" refers to the more severely affected eye on Day1, i.e., the day of the Baseline Visit of a study or trial. The other eye is referred to herein as the non-study eye or the fellow eye. The progress of both eyes may, but need not be, followed as treatment progresses.

The terms "affected with a disease or disorder," "afflicted with a disease or disorder," or "having a disease or disorder" are used interchangeably herein and refer to a subject or patient with any disease, disorder, syndrome or condition. No increased or decreased level of severity of the disorder is implied by the use of one the terms as compared to the other.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

When introducing elements of the present disclosure or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e., A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein in relation to a numerical value x means x±10%.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may optionally be omitted where used herein.

An "intention-to-treat" population includes all clinical trial subjects who are randomized according to randomized treatment assignment. Randomized controlled trials often suffer from two major complications, i.e., noncompliance and missing outcomes. One potential solution to this problem is a statistical concept called intention-to-treat (ITT) analysis. ITT analysis ignores noncompliance, protocol deviations, withdrawal, and anything that happens after randomization. ITT analysis maintains prognostic balance generated from the original random treatment allocation. In ITT analysis, estimate of treatment effect is generally conservative. A better application of the ITT approach is possible if complete outcome data are available for all randomized subjects. Per-protocol population is defined as a subset of the ITT population who completed the study without any major protocol violations. See, e.g., Gupta S K, Intention-to-treat concept: A review, Perspect Clin Res. 2011 July-September; 2(3): 109-112.

The term "teprotumumab," also known as RV-001 and R-1507, is a human monoclonal antibody that binds to insulin-like growth factor-1 receptor (IGF-1R). It has CAS number 1036734-93-6 and comprises a SEQ ID NO.S 1-8 disclosed herein (see, e.g., table 17). It may be referred to in the alternative throughout this disclosure as "Antibody 1."

Antibodies

The sequences of the heavy chains and light chains of examples of antibodies that may be used in the methods of the invention, each comprising three CDRs on the heavy chain and three CDRs on the light chain are provided below. The sequences of the CDRs, heavy chains, light chains as well as the sequences of the nucleic acid molecules encoding the CDRs, heavy chains and light chains of the antibodies are disclosed in the sequence listing. The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR2) and CDRL3 (or LCDR3), respectively. Table 1 provides the SEQ ID numbers for the amino acid sequences of the six CDRs of the heavy and light chains, respectively, of the antibodies that may be used in the methods disclosed herein.

TABLE 1

SEQ ID Numbers for CDR Polypeptides of Antibodies that may be used in the methods disclosed herein.

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| Antibody 1 | 1 | 2 | 3 | 4 | 5 | 6 |
| Antibody 2 | 1 | 9 | 3 | 4 | 10 | 6 |

In one embodiment, an antibody or antibody fragment useful in the methods disclosed herein comprises at least one CDR with a sequence that has at least 95% sequence identity to any one of SEQ ID NOs: 1-6, 9, or 10 and specifically inhibits (or blocks) Insulin Like Growth Factor-I Receptor (IGF-1R).

In another embodiment, the antibody or antigen binding fragment that can be used in the methods comprising a heavy chain comprises one or more (i.e. one, two or all three) heavy chain CDRs from antibody 1 or antibody 2 and specifically inhibits or blocks IGF-1R.

In yet another embodiment, the antibody or antigen binding fragment useful in the methods disclosed herein comprises a heavy chain CDR1 with the amino acid sequence of SEQ ID NO: 1; a heavy chain CDR2 with the amino acid sequence of SEQ ID NO: 2, or SEQ ID NO: 9; and a heavy chain CDR3 with the amino acid sequence of SEQ ID NO: 3. In some embodiments, the antibody or antibody fragment comprises a heavy chain comprising the amino acid sequence of (i) SEQ ID NO: 1 for CDRH1, SEQ ID NO: 2 for CDRH2 and SEQ ID NO: 3 for CDRH3; or (ii) SEQ ID NO: 1 for CDRH1, SEQ ID NO: 9 for CDRH2, and SEQ ID NO: 3 for CDRH3 and specifically inhibits IGF-1R.

In another embodiment, the antibody or antigen binding fragment that can be used in the methods disclosed herein comprising a light chain comprising one or more (i.e. one, two or all three) light chain CDRs from antibody 1 or antibody 2 and specifically inhibits IGF-1R.

In yet another embodiment, an antibody or antibody fragment useful in the methods disclosed herein comprises a light chain CDR1 with the amino acid sequence of SEQ ID NO: 4; a light chain CDR2 with the amino acid sequence of SEQ ID NO: 5, or SEQ ID NO: 10; and a light chain CDR3 with the amino acid sequence of SEQ ID NO: 6. In some embodiments, the antibody or antibody fragment comprises a light chain comprising the amino acid sequence of (i) SEQ ID NO: 4 for CDRL1, SEQ ID NO: 5 for CDRL2, and SEQ ID NO: 6 for CDRL3; or (ii) SEQ ID NO: 4 for CDRL1, SEQ ID NO: 10 for CDRL2, and SEQ ID NO: 6 for CDRL3.

In one embodiment, the antibody, or antigen binding fragment thereof, comprises all of the CDRs of antibody 1 as listed in Table 1, and specifically inhibits (or blocks) Insulin Like Growth Factor-I Receptor (IGF-1R). In another embodiment, the antibody, or antigen binding fragment thereof, comprises all of the CDRs of antibody 2 as listed in Table 1, and specifically inhibits (or blocks) IGF-1R.

The SEQ ID numbers for the amino acid sequence for the heavy chain variable region (VH) and the light chain variable region (VL) of antibodies useful in the methods disclosed herein are listed in Table 2.

TABLE 2

SEQ ID Numbers for $V_H$ and $V_L$ amino acid for Antibodies that may be used in the methods disclosed herein.

| | $V_H$ amino acid | $V_L$ amino acid |
|---|---|---|
| Antibody 1 | 7 | 8 |
| Antibody 2 | 11 | 12 |

In one embodiment, the antibody or antigen binding fragment that can be used in the methods disclosed herein comprises a heavy chain variable region having an amino acid sequence that is about 70%, 75%, 80%, 85%, 90%, 95%, 97%, 98%, 99% or 100% identical to the sequence recited in SEQ ID NOs: 7 or 11 wherein the antibody specifically inhibits IGF-1R.

In another embodiment, the antibody or antigen binding fragment that can be used in the methods disclosed herein specifically inhibits IGF-1R and comprises a heavy chain variable region comprising the amino acid sequence of SEQ ID NO: 7 and a light chain variable region comprising the amino acid sequence of SEQ ID NO: 8; or a heavy chain variable region comprising the amino acid sequence of SEQ ID NO: 11 and a light chain variable region comprising the amino acid sequence of SEQ ID NO: 12.

Examples of antibodies useful in the methods disclosed herein disclosed herein include, but are not limited to, antibody 1, and antibody 2. In some embodiments, antibody 1 is teprotumumab.

Variant antibodies are also included within the scope of the antibodies to be used in the methods disclosed herein. Thus, variants of the sequences recited herein are also included. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are antibodies to be used in the methods disclosed herein. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences disclosed herein are antibodies to be used in the methods disclosed herein.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Antibodies used with the methods disclosed herein can be coupled to a drug for delivery to a treatment site or coupled to a detectable label to facilitate imaging of a site comprising cells of interest. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody and an epitope of interest can be facilitated by attaching a detectable substance to the antibody and detecting the antibody-antigen complex by suitable detection means known to one of skill in the art.

Antibodies, or antigen binding fragments thereof, used with the methods disclosed herein can be of any isotype (e.g., IgA, IgG, IgM i.e. an $\alpha$, $\gamma$ or $\mu$ heavy chain). In one embodiment the antibody is IgG. Within the IgG isotype, antibodies may be IgG1, IgG2, IgG3 or IgG4 subclass. The antibodies may have a $\kappa$ or a $\lambda$ light chain.

The antibodies, or an antigen binding fragments thereof, used with the methods disclosed herein can be administered by any route known to one of skill in the art. Non-exhaustive examples of routes that can be used are provided below.

Pharmaceutical Compositions

The pharmaceutical compositions used in the methods disclosed herein comprise one or more of: the antibodies or antibody fragments described above and a pharmaceutically acceptable carrier or excipient. Although the carrier or excipient may facilitate administration, it should not itself induce the production of antibodies harmful to the subject or individual receiving the composition; nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles, and are known to one of skill in the art.

The antibodies, or an antigen binding fragments thereof, or pharmaceutical compositions used with the methods disclosed herein may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions. Typically, the therapeutic compositions may be prepared as injectables, either as liquid solutions or suspensions. Solid forms suitable for solution in, or suspension in, liquid vehicles prior to injection may also be prepared.

In one embodiment, the antibody, or an antigen binding fragment thereof, or pharmaceutical composition is administered intravenously. In another embodiment, the antibody, or an antigen binding fragment thereof, or pharmaceutical composition is administered by intravenous infusion.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

The methods of the present invention can use an antibody, or an antigen binding fragment thereof, as described above, alone or in combination with other pharmaceutically active compounds, to treat conditions such as those disclosed hereinabove. The additional pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of an antibody, or an antigen binding fragment thereof, of the present invention and one or more additional pharmaceutically active compounds.

In some embodiments, the antibody, or an antigen binding fragment thereof, of the present invention is used in combination with existing therapies, including, but not limited to, corticosteroids; rituximab and other anti-CD20 antibodies; tocilizumab and other anti-IL-6 antibodies; or selenium, infliximab and other anti-TNFα antibodies. In some embodiments, the antibody, or an antigen binding fragment thereof, of the present invention is used in combination with TSHR inhibitors.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1. Description of Randomized, Placebo-Controlled Clinical Trial to Determine the Efficacy and Safety of Teprotumumab (Antibody 1)

A multicenter, double-masked, randomized, placebo-controlled clinical trial was conducted to determine the efficacy and safety of teprotumumab, a human monoclonal antibody and inhibitor of IGF-1R, in patients with active, moderate-to-severe TED. A total of 88 patients were randomly assigned to receive placebo or active drug administered intravenously once every 3 weeks for a total of eight infusions. The primary end point was the response in the study eye (selected by investigators at baseline as the most affected eye). This response was defined as a reduction of 2 points or more in the Clinical Activity Score (CAS) and a reduction of 2 mm or more in proptosis at week 24. CAS scores could range from 0 to 7, with a score of ≥4 indicating moderate to severe active TED. Secondary end points, measured as continuous variables, included proptosis, the CAS, and results on the Graves' ophthalmopathy-specific quality-of-life questionnaire. Adverse events were also assessed.

The trial was conducted at 15 sites. Patients were recruited between Jul. 2, 2013, and Sep. 23, 2015. Major inclusion criteria were the following: patients were 18 to 75 years of age, with TED that were enrolled into the study no more than 9 months after the onset of orbital symptoms, had a Clinical Activity Score of 4 or more on a 7-point scale in the more severely affected (study) eye, and had not received surgical or medical treatment, with the exception of oral glucocorticoids (a cumulative dose of ≤1 g of methylprednisolone or equivalent, with a 6-week washout period). Serum glucose levels in patients with diabetes were well controlled. Female patients had negative pregnancy tests and used approved contraception. Patients with optic neuropathy, severe ocular surface damage, or an improved CAS of 2 points or more between screening and baseline visits were excluded.

The trial comprised three phases: screening (2 to 6 weeks), intervention (24 weeks), and follow-up (48 weeks). Screening involved one to three visits. During the intervention phase, patients were assessed at baseline and every 3 weeks for 24 weeks; efficacy was assessed at weeks 6, 12, 18, and 24. Data from week 24 were used to assess the primary and secondary end points. With the exception of rare instances, at every assessment, patients were evaluated by the same ophthalmologist, who was unaware of the trial-group assignments. A change of 2 points in the 7-component CAS was considered to be clinically relevant. Proptosis was assessed with the use of a Hertel exophthalmometer. Quality of life was evaluated with the use of the Graves' ophthalmopathy-specific quality-of-life questionnaire (GO-QoL), comprising two subscales assessed separately or in combination; scores on each subscale as well as the score on the overall GO-QOL scale had a range of 0 to 100 points. A change of 8 points was considered to be clinically relevant. Subjective diplopia was assessed by categorizing patients according to four grades. A change of one grade was considered to be clinically relevant.

The trial was designed by academic investigators in collaboration with the manufacturer of teprotumumab, which provided primary financial support for the trial and teprotumumab free of charge and was responsible for trial oversight.

Institutional review and ethics committees of the participating centers and the investigators approved the research protocol. An independent data and safety monitoring board oversaw the safety aspects of the trial. Witnessed, written informed consent was obtained from all patients. Data were obtained by the investigators and their staff.

The investigators vouch for the accuracy and completeness of the data generated at their respective institutions. The investigators and the manufacturer vouch for the fidelity of the trial to the protocol.

Moieties/Interventions Used in Randomized, Placebo-Controlled Trials

Teprotumumab was provided as freeze-dried powder in glass vials. The placebo was 0.9% sodium chloride solution supplied by the research pharmacy. Patients received eight intravenous infusions, one every 3 weeks starting with an initial dose of 10 mg per kilogram of body weight, followed by 20 mg per kilogram for the remaining seven infusions.

Randomization and Masking the Trial

The randomized trial was designed to assess efficacy and safety. Patients were randomly assigned in the double-masked intervention phase to either of two intervention groups in a 1:1 ratio in blocks of two, stratified within each clinical center according to smoking status with the use of an interactive Web-response system. Study pharmacists who were aware of the trial-group assignments prepared the masked infusion. The on-site principal investigators could identify a patient's intervention (teprotumumab or placebo) only in the case of an emergency.

Calculation of Clinical Activity Score (CAS)

The clinical activity score consists of seven components: spontaneous retrobulbar pain, pain on attempted eye movements (upward, side-to-side, and downward gazes), conjunctival redness, redness of the eyelids, chemosis, swelling of the caruncle/plica, and swelling of the eyelids. Each component was scored as present or absent, 1 or 0. The score at each efficacy assessment is the sum of all items present. This gave a range of 0-7, where 0 or 1 constitutes inactive disease and 7 severe active ophthalmopathy. A change of ≥2 points was considered clinically meaningful.

Evaluation of Graves' Ophthalmopathy Quality of Life (GO-QOL)

Quality of life was evaluated with the use of the GO quality of life questionnaire. The questionnaire has two self-assessment subscales; one covering impact of visual function on daily activities, the other assesses the impact of self-perceived appearance. The visual function subscale covers activities such as driving, walking outdoors, reading, watching television, etc. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of ≥8 points on the 0-100 scale has been shown to be clinically meaningful. The combined score takes raw scores from both subscales and again transforms them to a single 0-100 scale.

Assessment of Gorman Grading of Diplopia

The Gorman assessment of subjective diplopia includes four categories: no diplopia (absent), diplopia when the patient is tired or awakening (intermittent), diplopia at extremes of gaze (inconstant), and continuous diplopia in the primary or reading position (constant). Patients are scored according to which grade of diplopia they are experiencing. An improvement of ≥1 grade is considered clinically meaningful.

Outcomes of Trials

Patients who had a response were defined as those who met the composite primary end point at week 24. This end point comprised a reduction of 2 points or more in the CAS and a reduction of 2 mm or more in proptosis in the study eye in the absence of a corresponding amount of worsening in the non-study eye. Secondary end points were proptosis and the CAS (both measured as continuous variables over time) and assessment of the patient's quality of life with the use of the GO-QOL instrument (which includes two subscales that measure limitations in visual functioning and psychosocial functioning as a consequence of changed physical appearance). Patients were also categorized according to their level of response. Safety was assessed according to the incidence of adverse events, serious adverse events, and withdrawals due to adverse events.

Statistical Analysis of Outcomes of Trials

It was estimated that a sample of 84 patients would provide the trial with a power of 80% or more to detect a between-group difference if 42 patients per trial group had data that could be evaluated. On the basis of published trial results, it was expected that 30% of the patients in the placebo group and 60% of the patients in the teprotumumab group would have a response. All statistical tests were two-sided and performed at the 5% significance level. No interim data analysis was performed. Analyses were performed with the use of SAS software, version 9.1 (SAS Institute), after database lock.

The intention-to-treat population, which included all randomly assigned patients who received at least one infusion, was used to analyze the primary and secondary efficacy outcomes. The safety population, which included all patients who received teprotumumab or placebo, was used for all safety analyses.

In the primary analysis, we used a logistic-regression model with the intervention group as the model effect and smoking as a covariate. Patients who did not have week 24 data for any reason were considered to have treatment failure. Results of a stratified Cochran-Mantel-Haenszel chi-square test, with smoking status as the stratification factor, enabled confirmation of the logistic analysis results.

For assessment of the secondary end points (proptosis, CAS, and GO-QOL scores), a mixed model of repeated measurements was fit to the individual change from baseline with the use of the PROC MIXED procedure in SAS software. Each baseline score (including smoking status, intervention group, time, time according to intervention, and time according to baseline interaction) was incorporated into the analysis. Responses in the nonstudy eye were assessed with the use of identical analyses.

Initial Results of Trials

A total of 88 eligible patients underwent randomization. Of these patients, the intention-to-treat population of 87 patients (45 in the placebo group and 42 in the teprotumumab group) had more than one infusion. A total of 39 patients in the placebo group (87%) and 37 patients in the teprotumumab group (88%) completed the intervention as shown in FIG. 1.

As shown in FIG. 1, patients who met the primary inclusion criteria for being enrolled into the study within 9 months or less after the onset of orbital symptoms and who had a Clinical Activity Score of 4 points or more (on a scale from 0 to 7, with a score of ≥3, indicating active TED, were entered into the screening phase of the trial. One patient who did not meet the screening criteria for an "administrative reason" was screened after the screening period was closed. At the baseline visit (week 0), patients who met all inclusion and exclusion criteria were randomly assigned to receive teprotumumab or placebo in a 24-week intervention phase of the trial. Patients then entered a 1-year follow-up phase, which is ongoing. The intention-to-treat population was defined as all patients who received one infusion of teprotumumab or placebo and excluded one patient who was randomly assigned to teprotumumab but withdrew consent before the drug was administered. One patient discontinued the intervention during the intervention phase but returned for the week 24 assessment.

All patients met criteria for euthyroid status (within ±50% of the reference range) at trial entry; 25 of 87 patients (29%) had minor adjustments in the dose of levothyroxine or an anti-thyroid drug. Although patients were stratified according to smoking status, there was an imbalance between the two groups with respect to this variable (Table 3). The P values associated with the adjusted odds ratios presented in the next section, as well as the P values for the reduced proptosis and the reduction in the CAS (both measured as continuous variables) and for the GO-QOL score, were calculated with the use of analytic methods that adjusted for a potential imbalance in smoking status by including smoking as a covariate.

TABLE 3

Baseline Characteristics of the Patients.*

| Characteristic | Teprotumumab (N = 43) | Placebo (N = 44) |
|---|---|---|
| Demographic and clinical characteristics | | |
| Age - yr | 51.6 ± 10.6 | 54.2 ± 13.0 |
| Female sex - no. of patients (%) | 28 (65) | 36 (82) |
| Time since initiation of treatment for thyroid disease - mo† | | |
| Median | 8 | 15 |
| Range | 1-134 | 3-189 |
| Current treatment for thyroid disease - no. of patients (%) | | |
| Antithyroid drug‡ | 15 (35) | 20 (45) |
| Levothyroxine | 26 (60) | 23 (52) |
| Thyroid extract | 1 (2) | 3 (7) |
| Adjustment of medication at trial entry - no. of patients (%) | | |
| Levothyroxine | 8 (19) | 5 (11) |
| Antithyroid drug | 5 (12) | 7 (16) |
| Duration of eye symptoms or signs - mo | 4.7 ± 2.1 | 5.2 ± 2.3 |
| Duration of Graves' disease - mo | | |
| Median | 10.7 | 10.8 |
| Range | 1.2-228.0 | 1.2-299.0 |
| Smoking status - no. of patients (%)§ | | |
| Nonsmoker | 32 (74) | 26 (59) |
| Smoker | 11 (26) | 18 (41) |
| Biochemical characteristics | | |
| Thyrotropin-binding inhibitory immunoglobulins - % | 51.6 ± 26.9 | 48.7 ± 25.4 |
| Thyroid-stimulating immunoglobulins - % | 422.9 ± 118.1 | 435.1 ± 105.2 |
| Mean thyroid hormone levels - pmol/liter¶ | | |
| Free triiodothyronine | 4.8 ± 1.4 | 4.9 ± 1.7 |
| Free thyroxine | 16.3 ± 4.8 | 16.3 ± 3.6 |

TABLE 3-continued

| Baseline Characteristics of the Patients.* | | |
|---|---|---|
| Characteristic | Teprotumumab (N = 43) | Placebo (N = 44) |
| Levels of free triiodothyronine and free thyroxine - no. of patients (%) | | |
| Euthyroid at baseline and through intervention phase | 20 (46) | 13 (30) |
| Values occasionally outside normal range during intervention phase | 18 (42) | 25 (57) |
| Sustained out-of-range values during intervention phase | 5 (12) | 6 (14) |

*Plus-minus values are means ± SD. Additional patient characteristics are provided in Table S2. Patients were recruited in the following countries: Germany (19 patients), Italy (6), the United Kingdom (10), and the United States (53). A breakdown of randomization according to clinical center is provided in Table S3. Unless otherwise stated, baseline characteristics shown are from the safety population (44 patients in the placebo group and 43 patients in the teprotumumab group), which differs from the intention-to-treat population (45 patients in the placebo group and 42 patients in the teprotumumab group), since 1 patient in the placebo group received teprotumumab in error.

†Data shown are for 10 patients in the placebo group and 10 patients in the teprotumumab group.

‡The antithyroid drugs were carbimazole, methimazole, and propylthiouracil.

§Data for smoking status were based on patients who were current smokers at the time of the screening visit. Patients were stratified at randomization according to smoking status to balance the trial groups with respect to this known risk factor for thyroid-associated ophthalmopathy. However, there were imbalances in randomization blocks and discrepancies between patients who were randomly assigned to an intervention as nonsmokers at week 0 and those recorded as being smokers in their case-report forms. Data from the case-report forms were considered to be more accurate and were used to define smoking status at baseline.

¶The normal ranges of free triiodothyronine are 2.3 to 4.2 pg per milliliter (3.5 to 6.5 pmol per liter), and of free thyroxine, 0.9 to 1.8 ng per deciliter (11.6 to 23.2 pmol per liter).

Primary and Secondary End Points from Trials

Proptosis, the Clinical Activity Score, and the GO-QOL score were nearly identical at baseline in the two groups (Table 4). At baseline, there was an imbalance between the groups with respect to diplopia, with a higher occurrence in the teprotumumab-group.

Figure 2:
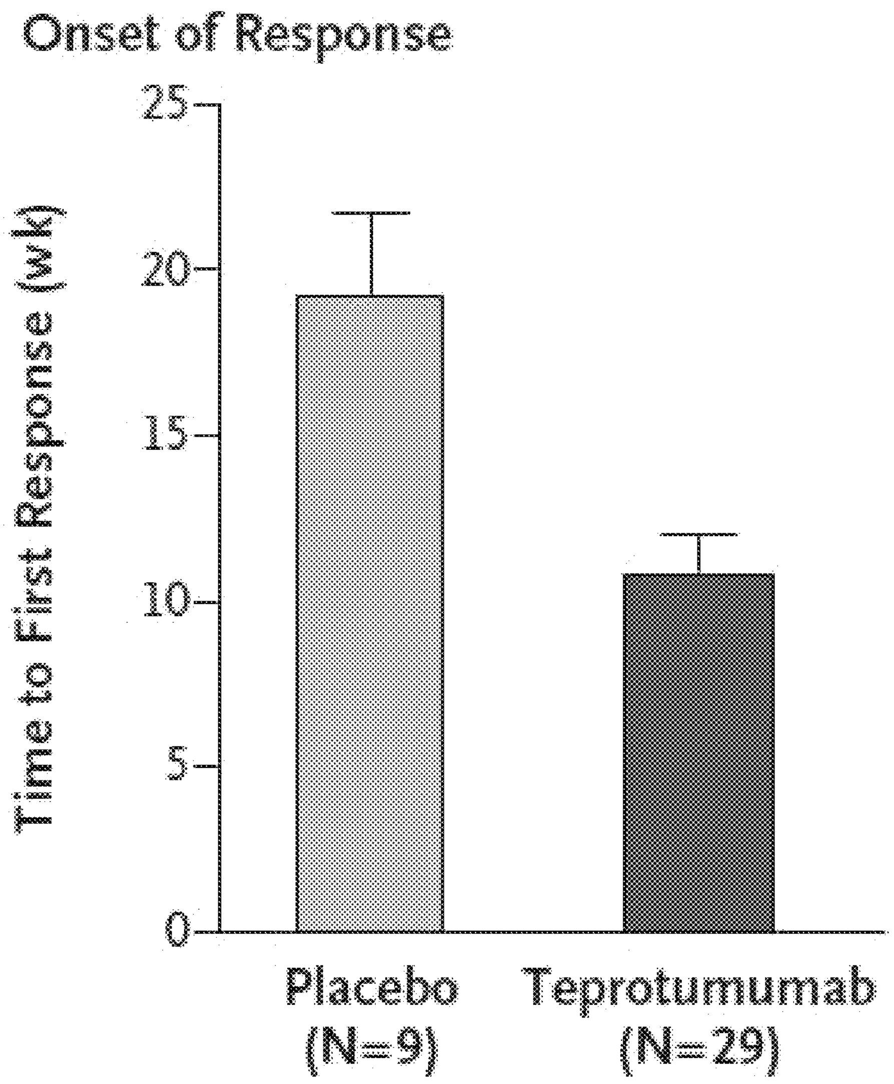
Figure 3:
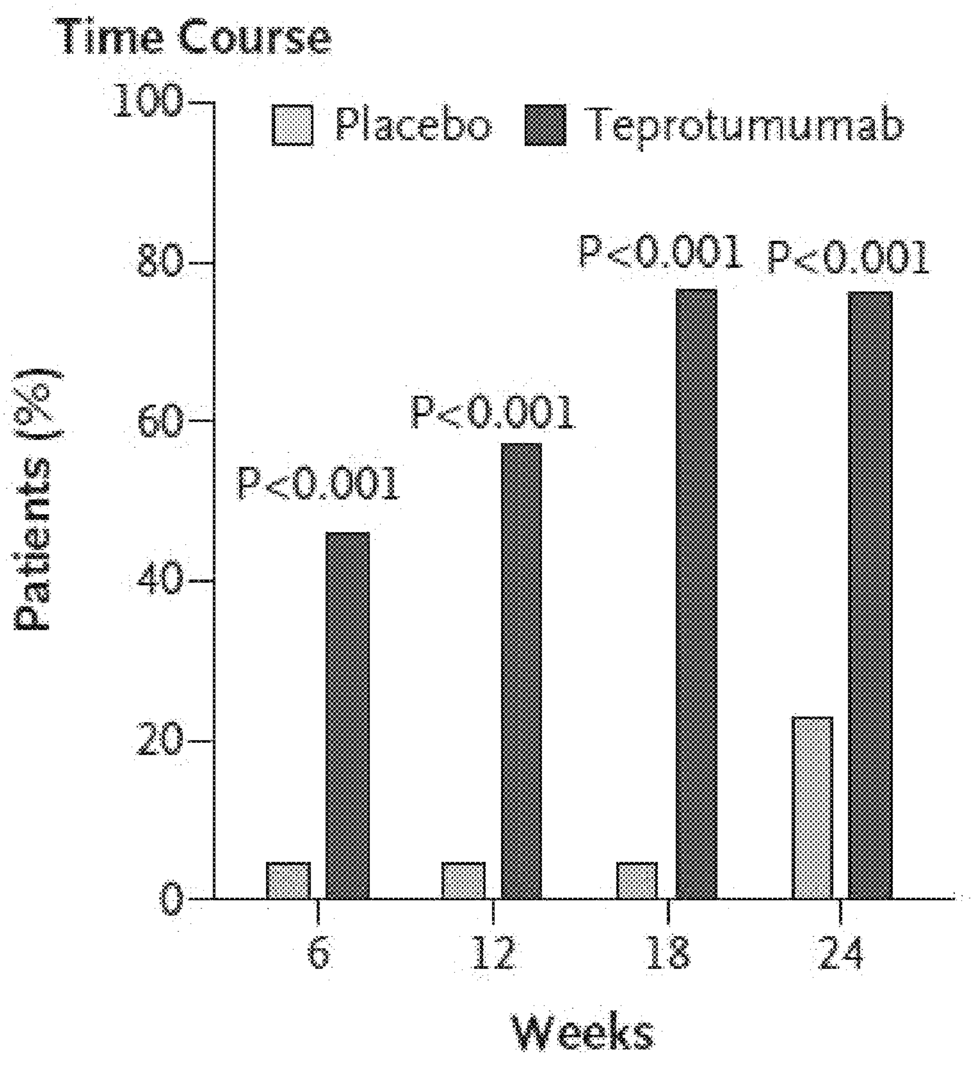

In the primary outcome measure in the intention-to-treat population, 9 of 45 patients who received placebo (20%) and 29 of 42 patients who received teprotumumab (69%) had a response at week 24 (adjusted odds ratio, 8.86; P<0.001). Similarly, in the per-protocol population, 8 of 36 patients who received placebo (22%) and 26 of 33 patients who received teprotumumab (79%) had a response at week 24 (adjusted odds ratio, 12.73; P<0.001). The time to the first response was markedly shorter in the teprotumumab group than in the placebo group (FIG. 2). The onset of the response was rapid. The proportion of patients who had a response was greater in the teprotumumab group than in the placebo group at weeks 6, 12, and 18 (P<0.001 for all comparisons) (FIG. 3). In a separate analysis that graded the level of response, more patients in the teprotumumab group than in the placebo group had reductions of 3 points or more in the CAS and reductions of 3 mm or more in proptosis (P<0.001 for the comparisons at every level of response) (FIG. 4).

Figure 4:
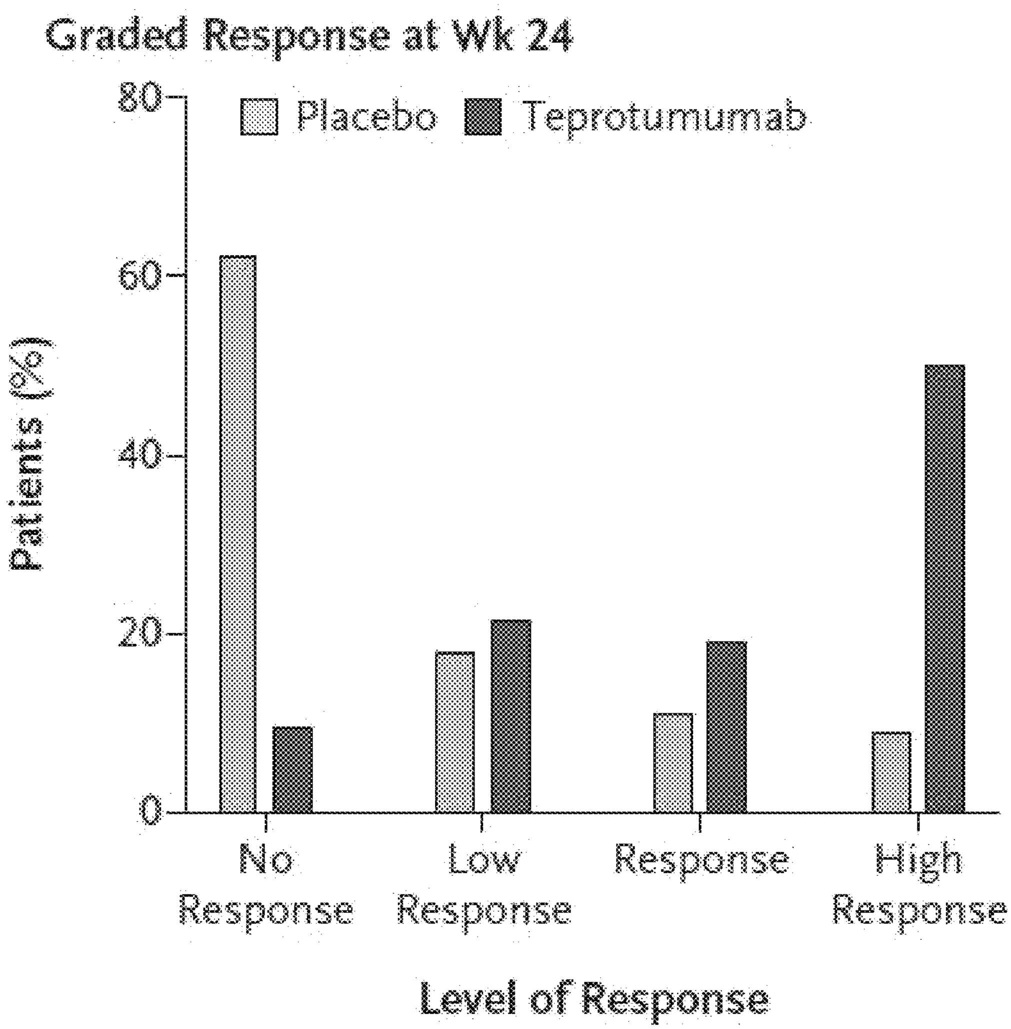

As shown in FIG. 2-4, the primary end point was a logistic regression of response status according to trial-drug group at week 24. A response was defined as a reduction of 2 mm or more in proptosis and a reduction of 2 points or more in the CAS in the study eye, without an equivalent increase in proptosis or in the CAS in the non-study eye. The CAS, which comprises seven components, ranges from 0 to 7, and a change of 2 points is considered to be clinically relevant. As shown in Panel B, in the analysis of the time to first response, data are expressed as means #SE. As shown in Panel C, in the analysis of the time course in patients who met the response criteria, P values were calculated with the use of a logistic-regression model. As shown in Panel D, in the grading of a response at week 24, P<0.001 was calculated with the use of a logistic-regression model. A high response indicates that proptosis was reduced by 3 mm or more and the CAS was reduced by 3 points or more. A response indicates a reduction of 2 mm or more, but less than 3 mm, in proptosis and 2 points or more, but less than 3 points, in the CAS. A low response indicates reductions of 1 mm or more, but less than 2 mm, in proptosis and 1 point or more, but less than 2 points, in the Clinical Activity Score. No response indicates that the patient did not meet any response criteria or had missing evaluations at week 24.

Figure 5:
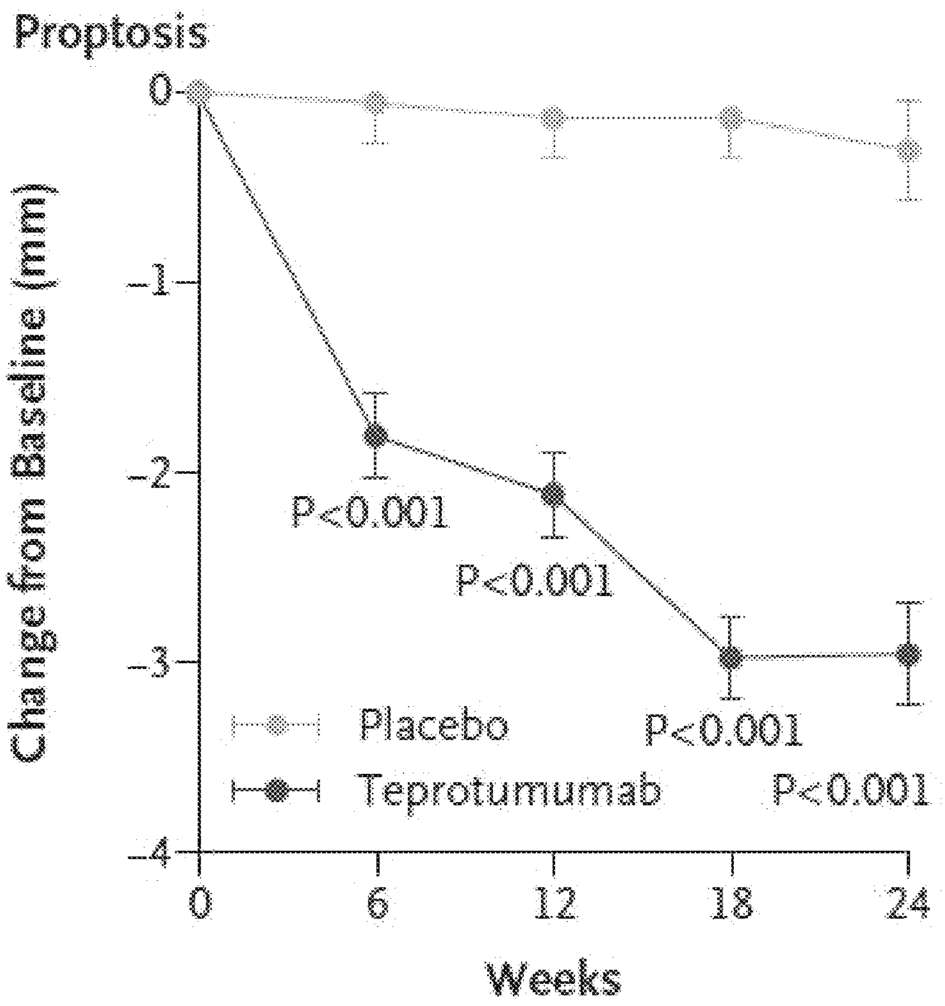

At weeks 6, 12, 18, and 24, the reduction in proptosis from baseline, measured as a continuous variable, was significantly greater in patients who received teprotumumab than in those who received placebo (P<0.001 for all comparisons) (FIG. 5). At week 24, a total of 17 of 42 patients (40%) who received teprotumumab had a reduction of 4 mm or more in proptosis, as compared with 0% of patients who received placebo.

Figure 6:
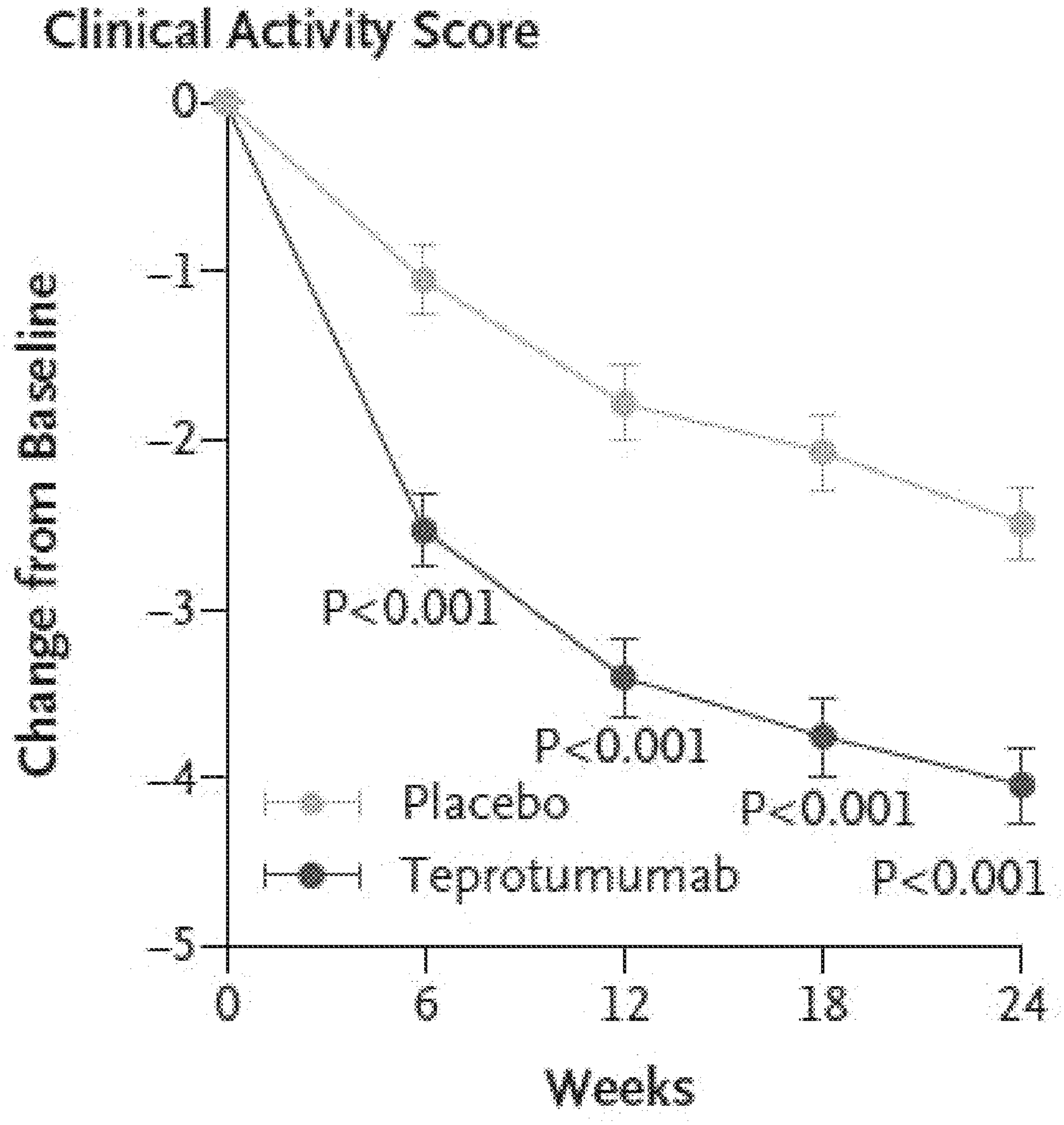
Figure 7:
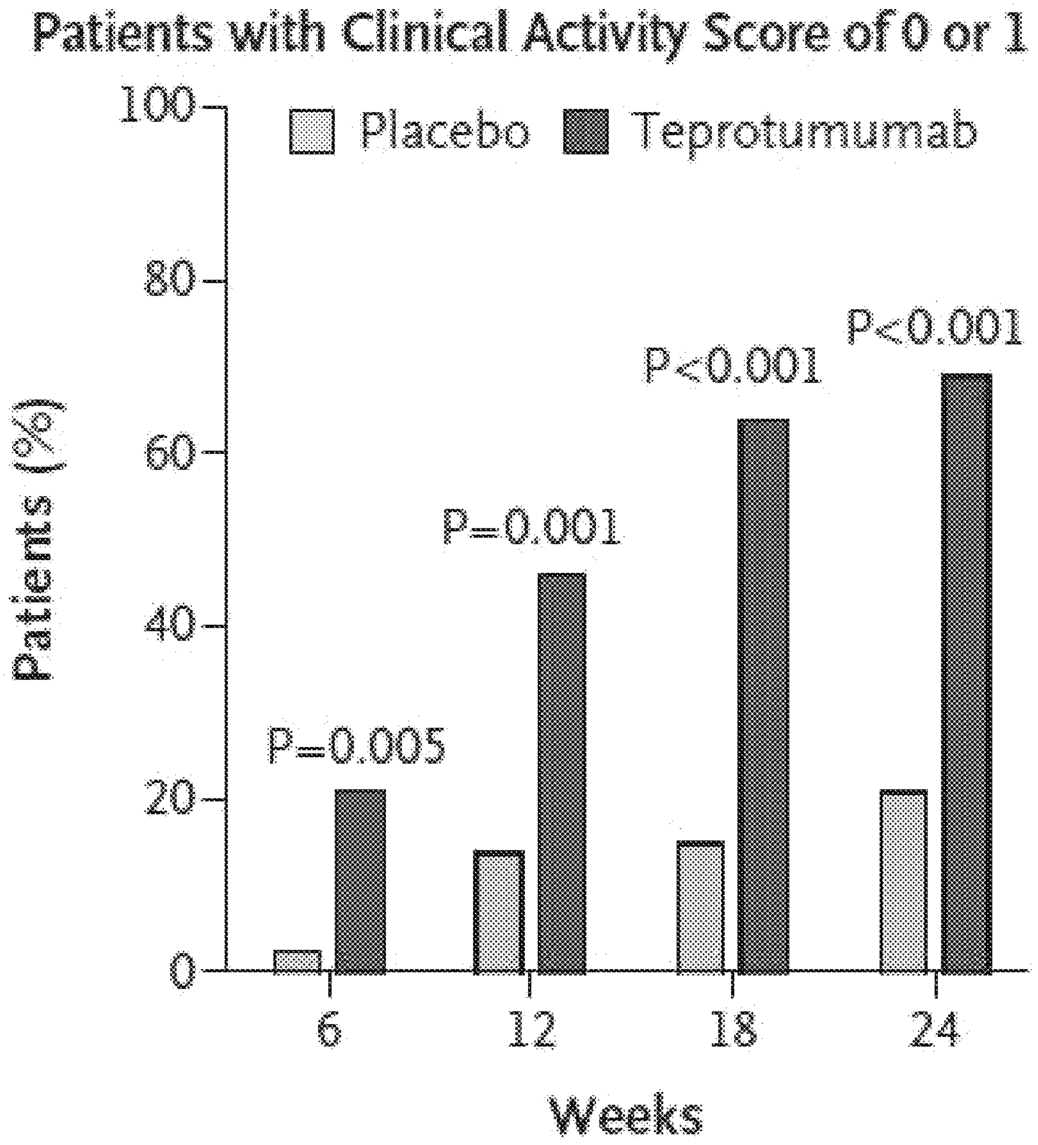

At weeks 6, 12, 18, and 24, the reduction in the Clinical Activity Score in the teprotumumab group was also significantly greater than that in the placebo group (P<0.001 for all comparisons) (FIG. 6), although this score also decreased markedly and progressively in the placebo group. The baseline Clinical Activity Score in the teprotumumab group was 5.1 points, and the mean reduction at week 24 was 4 points. This indicates that some patients had a near-maximal therapeutic effect. This finding was confirmed by a post hoc categorical analysis involving patients who had a CAS of 0 points or 1 point; this analysis showed that 69% of the patients who received teprotumumab had a Clinical Activity Score of 0 or 1 at week 24, as compared with 21% of the patients who received placebo (adjusted odds ratio, 8.97; P<0.001) (FIG. 7). A post hoc analysis showed that the reductions in the CAS in the teprotumumab group were broad-based (i.e., they were not driven by large decreases in subsets of the CAS components). Reductions in the CAS seen in the placebo group were similarly broad-based.

Figure 8:
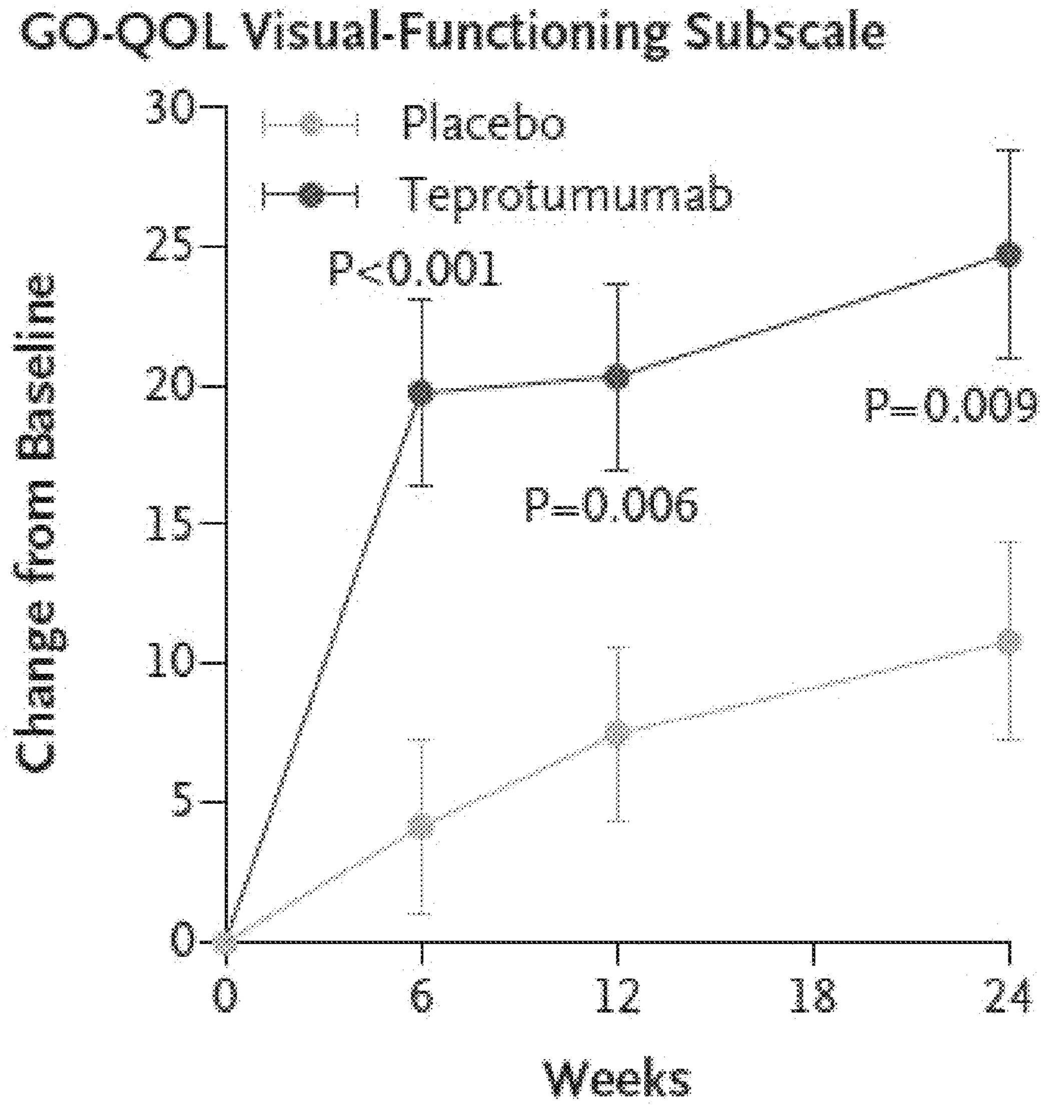
Figure 9:
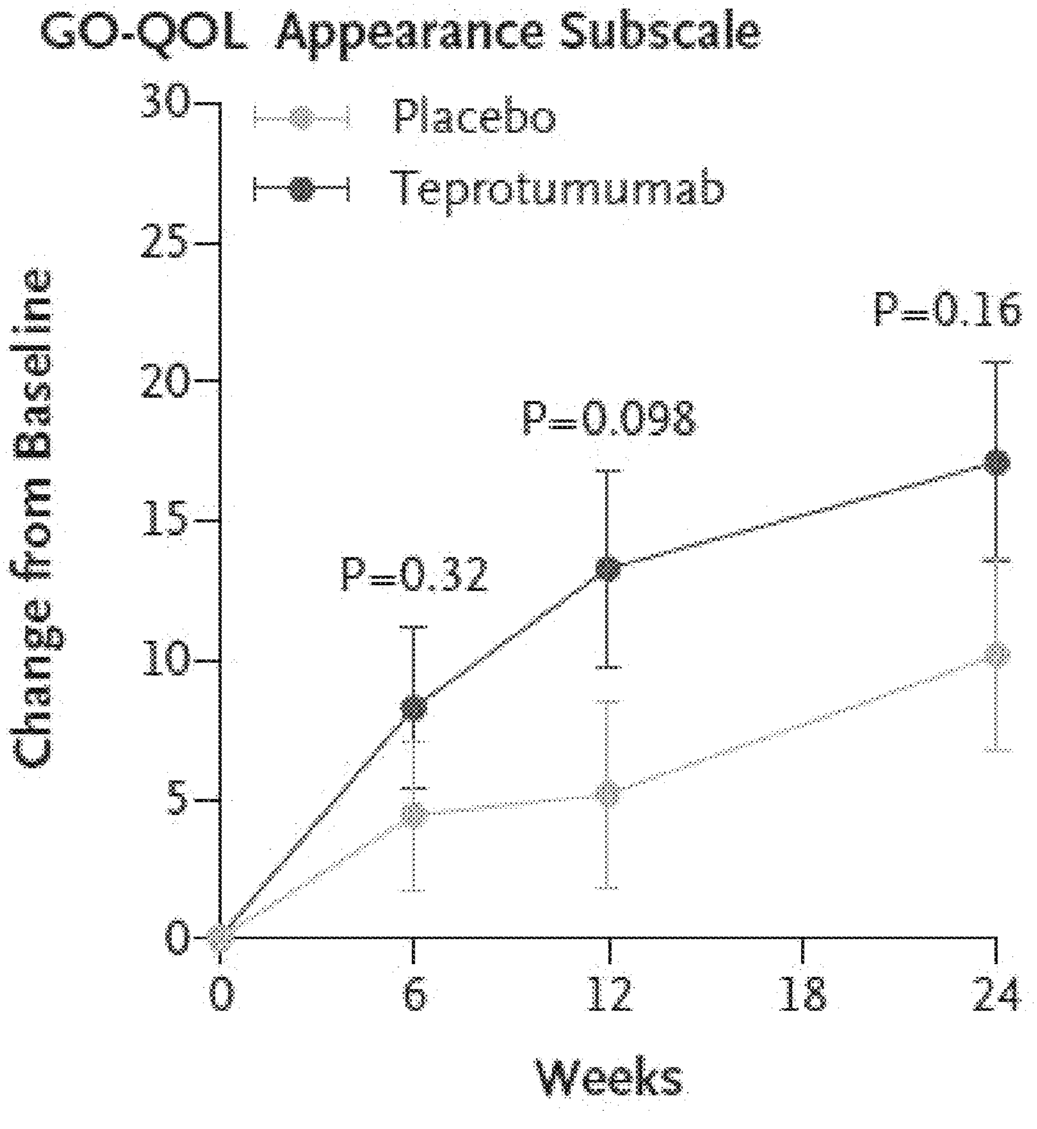
Figure 10:
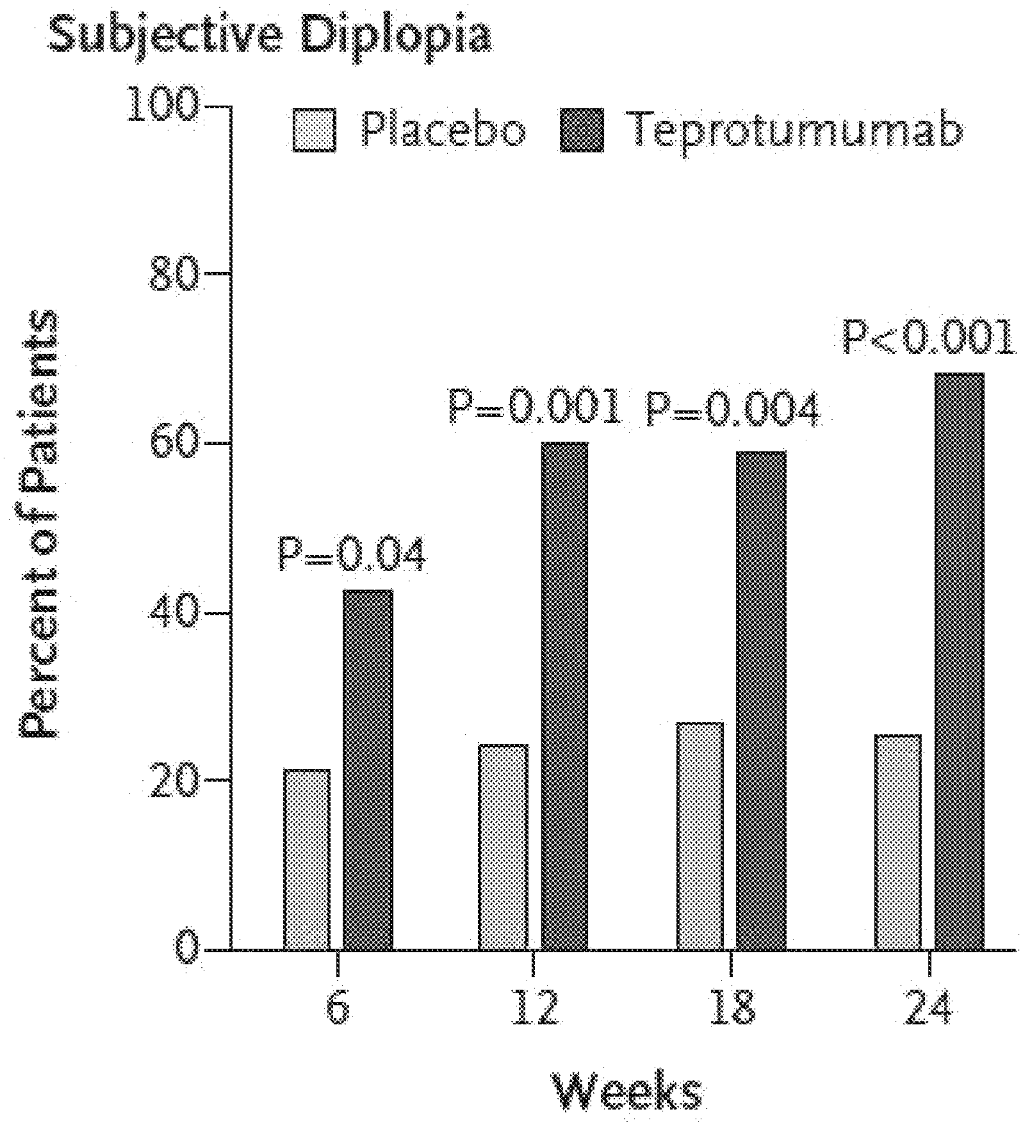

The GO-QOL visual-functioning score increased significantly in the teprotumumab group at all time points (FIG. 8). This increase ranged from 12.8 to 15.6 points greater than the increase in the placebo group. On the GO-QOL appearance subscale, a consistent trend toward improvement emerged but did not achieve significance (FIG. 9). When the two scales were combined, significance was seen at weeks 6, 12, and 24 (P=0.003, P=0.007, and P=0.012, respectively) (Table 4). Response rates with respect to subjective diplopia were also significantly higher in the teprotumumab group than in the placebo group (FIG. 10).

Efficacy was also assessed at week 28 (7 weeks after the final dose was administered), and this assessment showed no evidence of diminution (i.e., no "rebound" phenomenon). Indeed, the numbers of patients with a response increased and proptosis and the CAS were further reduced at week 28 as compared with week 24. The efficacy of teprotumumab in the non-study eye was also similar to the efficacy in the study eye with respect to response rates, proptosis, and the CAS. Serum assays showed no drug-induced changes in interleukin-6, interleukin-16, and RANTES (regulated on activation, normal T-cell expressed and secreted) levels. During the intervention phase, levels of thyroid-stimulating immunoglobulins and thyrotropin-binding inhibitory immunoglobulins decreased progressively (by 15 to 30%) in the two groups.

TABLE 4

Results of Efficacy Assessment before and after Administration of Trial Drug.*

| Variable | Teprotumumab (N = 42) | Placebo (N = 45) | Odds Ratio (95% CI) | P Value |
|---|---|---|---|---|
| Response analysis | | | | |
| Primary outcome measure: response in study eye at wk 24 - no. of patients/total no. (%)† | | | | |
| Intention-to-treat population | 29/42 (69) | 9/45 (20) | 8.86 (3.29-23.8) | <0.001 |
| Per-protocol population | 26/33 (79) | 8/36 (22) | 12.73 (4.01-40.4) | <0.001 |
| Time to first response - wk | 11.2 ± 6.6 | 18.7 ± 7.6 | | NC |
| Graded response - no. of patients (%)‡ | | | 11.80 (4.72-29.5) | <0.001 |
| High response | 21 (50) | 4 (9) | | |
| Response | 8 (19) | 5 (11) | | |
| Low response | 9 (21) | 8 (18) | | |
| No response or missing data | 4 (10) | 28 (62) | | |
| Proptosis - mm | | | | |
| Baseline | 23.4 ± 3.2 | 23.1 ± 2.9 | | |
| Change from baseline | −2.46 ± 0.20 | −0.15 ± 0.19 | | <0.001 |
| Clinical Activity Score§ | | | | |
| Baseline | 5.1 ± 0.975 | .2 ± 0.74 | | |
| Change from baseline | −3.43 ± 0.18 | −1.85 ± 0.17 | | <0.001 |
| GO-QOL score¶ | | | | |
| Combined visual-functioning and appearance subscales | | | | |
| Baseline | 34.5 ± 7.3 | 34.5 ± 6.8 | | |
| Change from baseline | 17.7 ± 2.4 | 6.8 ± 2.3 | | <0.01 |
| Visual-functioning subscale | | | | |
| Baseline | 16.9 ± 4.4 | 17.8 ± 4.3 | | |
| Change from baseline | 21.7 ± 2.9 | 7.5 ± 2.7 | | <0.001 |
| Appearance subscale | | | | |
| Baseline | 17.6 ± 4.51 | 6.7 ± 3.8 | | |
| Change from baseline | 12.9 ± 2.8 | 6.6 ± 2.7 | | 0.1 |
| Subjective diplopia‖ | | | | |
| Baseline according to grade - no. of patients (%) | | | 3.78 (1.68-8.54)** | 0.001 |
| No diplopia | 4 (10) | 14 (31) | | |
| Intermittent | 16 (38) | 19 (42) | | |
| Inconstant | 7 (17) | 8 (18) | | |
| Constant | 15 (35) | 4 (9) | | |
| Wk 24 according to grade - no. of patients (%) | | | | |
| No diplopia | 21 (50) | 18 (40) | | |
| Intermittent | 4 (10) | 8 (18) | | |
| Inconstant | 9 (21) | 7 (16) | | |
| Constant | 4 (10) | 6 (13) | | |
| Wk 24 response - no. of patients/total no. (%) | 26/38 (68) | 10/39 (26) | | <0.001 |

*Plus-minus values are means ± SD, except for the change from baseline in proptosis, which is expressed as means ± SE. CI denotes confidence interval, and NC not calculated;

†The primary outcome measure was analyzed with the use of a logistic-regression model that included smoking as a covariate, with a supporting sensitivity analysis conducted in the per-protocol population. The intention-to-treat population, defined as all patients who received an infusion of placebo or teprotumumab, excluded one randomly assigned patient who withdrew consent before drug administration. Secondary end points, analyzed hierarchically, were the Graves' ophthalmopathy-specific quality-of-life (GO-QoL) combined score, proptosis, the Clinical Activity Score, the GO-QoL visual-functioning score, and the GO-QoL appearance score. These continuous variables were analyzed with the use of a mixed model of repeated measurements with smoking as a covariate. Any apparent discrepancies between the tabulated mixed model of repeated-measurements calculations for change from baseline and data plotted in the figures are because tabulated data are an average difference between the trial groups over all post-baseline time points up to week 24. Values plotted in the figures are calculations of the mean change from baseline for specific time points. Prespecified exploratory end points included the time to first response, graded response, and subjective diplopia.

TABLE 4-continued

| Results of Efficacy Assessment before and after Administration of Trial Drug.* | | | | |
|---|---|---|---|---|
| Variable | Teprotumumab (N = 42) | Placebo (N = 45) | Odds Ratio (95% CI) | P Value |

‡A high response indicates that proptosis was reduced by 3 mm or more and the Clinical Activity Score was reduced by 3 points or more. A response indicates a reduction of 2 mm or more but less than 3 mm in proptosis and 2 points or more but less than 3 points in the Clinical Activity Score. A low response indicates reductions of 1 mm or more but less than 2 mm in proptosis and 1 point or more but less than 2 points in the Clinical Activity Score. No response indicates that the patient did not meet any response criteria or had missing evaluations at week 24. The P value for the comparison of placebo with teprotumumab was calculated for the overall distribution of graded responses, with the use of a logistic-regression model for cumulative logits.

§The Clinical Activity Score comprised seven components. Scores range from 0 to 7, and a change of 2 points is considered to be clinically relevant.

¶Quality of life was evaluated with the use of the GO-QoL questionnaire.24 The GO-QoL comprises two subscales, and scores on each subscale as well as the score on the overall GO-QOL scale have a range of 0 to 100 points. A change of 8 points is considered to be clinically relevant.

||Subjective diplopia was assessed on the basis of four grades, and a change of one grade or more is considered to be clinically relevant. A response in patients with diplopia was defined as a decrease of one grade or more. The chi-square test was used to compare data from patients who had a response with data from those who did not at week 24.

**The estimated odds ratio shown was calculated with the use of logistic regression for cumulative logits. This imbalance should be viewed in light of the large number of characteristics assessed at baseline. A sensitivity post hoc logistic-regression analysis of the week 24 response, which included adjustment for baseline smoking status, sex, study eye, and diplopia, did not show a substantial difference from the primary analysis (adjusted odds ratio, 8.16; P < 0.001).

Safety During the Trials

Adverse events that emerged during the intervention phase, that occurred in more than 5% of patients in the teprotumumab group, and that were greater in number in the teprotumumab group than in the placebo group are listed in Table 5. The majority of adverse events were mild, involved no treatment, and resolved while the patients continued to receive the intervention. Hyperglycemia, the only adverse event clearly identified by the investigators as being related to teprotumumab, was monitored by assessing blood glucose and glycated hemoglobin levels. Hyperglycemia in patients who did not have diabetes was uniformly grade 1, was intermittent, and occurred at similar rates in the two groups. Grade 2 or 3 hyperglycemia occurred in some patients with diabetes who received teprotumumab, and it was well controlled after adjustment of the medication for diabetes. Glycemic control, assessed according to the glycated hemoglobin level, was similar to that at baseline levels after the intervention phase in all patients who received antibody.

No deaths occurred during the trial. A total of 6 patients in each group discontinued the intervention. Serious adverse events occurred in 5 of 43 patients in the teprotumumab group (12%) and in 1 of 45 patients in the placebo group (2%) (Table 5). Two serious adverse events (diarrhea and mental confusion) in patients who received teprotumumab were categorized by the investigators as "possibly related" to the drug. Other serious adverse events were categorized as "unrelated." Although designated as having a nonresponse treatment failure in the analyses, these 5 patients all met response criteria at their early withdrawal visit. Antidrug antibodies were detected in 1 patient in the teprotumumab group at baseline and in 1 patient during the intervention phase (week 3). Both patients tested negative on subsequent visits (at weeks 9 and 24), and neither patient had neutralizing antibodies; using the term in the context that neither had marked reductions in plasma levels of teprotumumab. Four patients in the placebo group tested positive for antidrug antibodies at baseline; all were graded as having low-level antibody responses.

TABLE 5

| Adverse Events and Serious Adverse Events During Intervention. | | | |
|---|---|---|---|
| Variable | Teprotumumab (N = 43)* | Placebo (N = 44)* | Summary Details of Adverse Events in Teprotumumab Group |
| | number of patients (percent) | | |
| Adverse event† | | | |
| Nausea | 8 (19) | 4 (9) | Generally mild and reported after first and second infusions |
| Muscle spasms | 8 (19) | 2 (5) | Intermittent, 2 of 8 patients had muscle spasms for >1 wk and received muscle relaxants |
| Diarrhea | 6 (14) | 2 (5) | Treatment occurred in 2 of 6 patients, 1 case designated as a serious adverse event (see below) |
| Hyperglycemia | 5 (12) | 2 (5) | Mechanism-based adverse event |
| Alopecia | 3 (7) | 2 (5) | All mild and no treatment necessary |
| Dry skin | 3 (7) | 0 | All mild, 1 patient used topical dry-skin cream |
| Dysgeusia on days 1-2 | 3 (7) | 0 | In 2 of 3 patients, a transient "metallic" taste reported |
| Headache | 3 (7) | 2 (5) | Generally mild, 1 patient took paracetamol |
| Paresthesia | 3 (7) | 0 | "Tingling" reported in nose, feet, or chest; variable onset and in 2 of 3 patients occurred on 1 day |
| Hearing impairment | 3 (7) | 0 | Disparate symptoms, onset, and duration (i.e., one case of unilateral hearing impairment with onset 16 wk after end of therapy, ‡ one case of mild bilateral hearing impairment that resolved, and one case of tinnitus in a patient with a history of tinnitus) |

TABLE 5-continued

Adverse Events and Serious Adverse Events During Intervention.

| Variable | Teprotumumab (N = 43)* number of patients (percent) | Placebo (N = 44)* | Summary Details of Adverse Events in Teprotumumab Group |
|---|---|---|---|
| Weight loss | 3 (7) | 0 | Variable timing; decreases ranged from 5-9 lb (11-20 kg) |
| Any adverse event | 32 (74) | 32 (73) | |
| Serious adverse event§ | | | |
| Optic neuropathy¶ | 0 | 1 (2) | |
| Diarrhea | 1 (2) | 0 | Severe diarrhea in 1 patient with a 6-mo history of ulcerative colitis |
| Inflammatory bowel disease | 1 (2) | 0 | In 1 patient with recent diagnosis of ileitis and colitis, inflammatory bowel disease diagnosed and treated while patient received trial drug |
| *Escherichia* sepsis‖ | 1 | (2) 0 | *Escherichia coli* infection of unknown origin treated with intravenous antibiotics |
| Hashimoto's encephalopathy | 1 (2) | 0 | Provisional diagnosis after episodic mental confusion with no other neurologic symptoms |
| Urinary retention | 1 (2) | 0 | Diagnosed after patient had an inguinal herniorrhaphy |
| Any serious adverse event | 5 (12) | 1 (2) | |

*One patient in the placebo group received a single dose of teprotumumab in error at week 15. That patient is included here in the teprotumumab group.

†Adverse events of any cause were defined as those that occurred between the administration of the first dose and 30 days after the administration of the final dose. Listed adverse events that emerged during the intervention phase are those that occurred in more than 5% of patients in the teprotumumab group and that occurred in greater numbers in the teprotumumab group than in the placebo group. Patients may have had more than one adverse event.

‡ This case is included because the patient had unrelated, transient eustachian-tube dysfunction while receiving teprotumumab.

§Listed are all serious adverse events reported in the trial, including any adverse event involving hospitalization. In the teprotumumab group, four patients discontinued the intervention because of the following serious adverse events: diarrhea that occurred after six infusions, inflammatory bowel disease after seven, *Escherichia coli* sepsis after three, and Hashimoto's encephalopathy after six.

¶A total of three patients in the placebo group withdrew from the trial because of worsening eye symptoms or a lack of response. One case of dysthyroid optic neuropathy designated by an investigator as a serious adverse event occurred 3 days after the week 24 evaluation.

‖This patient was the only one whose intervention was unmasked during the course of the trial.

Summary and Conclusions from Trial-Based Data

Patients who received antibody had reductions in proptosis, the Clinical Activity Score, the GO-QOL (both the visual-functioning subscale and combined scales), and subjective diplopia that were clinically meaningful and significant (P<0.001) for all comparisons with placebo. Without being bound to any particular theory, the reductions observed across all components of the CAS suggest a therapeutic mechanism upstream from the inflammation in orbital tissues. The marked reduction in proptosis is similar to that reported after decompression surgery, without any risks or dangers associated with orbital surgery. Orbital surgery can provoke reactivation of ophthalmopathy and can cause or exacerbate strabismus; no such dangers arise in the methods disclosed herein. Taken together, the above studies suggest that the methods disclosed herein that recite inhibition of IGF-1R in patients with ophthalmopathy, may result in a disease-modifying reduction in the volume of orbital fat, muscles, or both.

Teprotumumab (Antibody 1) Reduces the Primary Outcome of Both CAS and Proptosis

Further to the multicenter, double-masked, randomized, placebo-controlled, phase-two trial of 88 patients with clinically active and moderate-to-severe GO described in Example 1 and the data obtained therefrom, extended primary and secondary outcome analyses was conducted.

To follow-up patients seven weeks after completion of treatment, mean, percent and individual outcomes in teprotumumab (Tepro) intent-to-treat patients as compared with placebo were analyzed. Included were the primary composite endpoint of percentage patients with ≥2 points reduction in clinical activity score (CAS, seven-point scale) and a reduction of ≥2 mm in proptosis, secondary individual endpoints of proptosis and CAS reduction, GO quality of life questionnaire (GO-QoL) and clinical severity improvement to assess possible relapse.

Thirty-one of 42 (74%) teprotumumab and six of 45 (13%) placebo treated patients with GO reached the primary outcome at treatment week 28 (p<0.001). As much as 93% of teprotumumab treated patients maintained response from end of treatment period (week 24). Proptosis response was similar to the primary outcome, with 55% of teprotumumab patients maintaining a high response (≥3 mm decrease). At week 28, 37/42 (88%) of teprotumumab and 27/45 (60%) of placebo patients reached the CAS outcome (p=0.003). All individual CAS components were also significantly different from placebo (p≤0.04) except eyelid erythema (p=0.06). Severity measures (percentage of patients with chemosis and swelling of eyelid decreased one grade, p=0.11 and p=0.01, respectively. Lid aperture decrease≥2 mm (p=0.09) favored teprotumumab, though not powered for these severity measures. Overall GO-QOL was significantly higher than placebo in the teprotumumab patients (p<0.001). Thyroid function was stable through the treatment phase and subsequent follow-up in both study groups. Teprotumumab did not affect thyroid-related hormone levels.

These data show that Tepro reduced the composite primary outcome of both CAS and proptosis, as well as the individual measures, i.e., GO-QOL, significantly at seven weeks after treatment discontinuation. This analysis also indicates that proptosis can serve as a primary and sensitive outcome for future clinical trials examining responses to therapy in GO.

Teprotumumab (Antibody 1) Treatment Improved Diplopia During Active Treatment and Maintained Significance after Drug Discontinuation in TED Patients The clinical trial of an IGF-1R inhibitor teprotumumab described in Example 1 and the data obtained therefrom (described in the above examples) demonstrates that teprotumumab reduced proptosis and clinical activity score in thyroid eye disease (TED) patients.

Further to those experiments, forty two (42) teprotumumab-treated patients with TED were examined for diplopia severity compared with 45 placebo-treated patients up to 48 weeks after trial completion. Diplopia grades were none, intermittent, inconstant, and constant.

At the end of the controlled trial (week 24) there were significantly more Tepro patients who had improved by ≥1 grade than placebo (62% v 22%, p<0.001), improvement in GO-QOL Visual for those with constant diplopia at baseline versus placebo (p=0.03), reduction in constant diplopia (36% to 9.5%) and increase in those with no diplopia (9.5% to 50%). Grade improvement remained significant out to week 72 of follow-up off drug (50% v 24%, p=0.01).

These data show that Tepro treatment improved diplopia during active treatment and maintained significance after drug discontinuation in TED patients.

Results of Follow-Up Treatment with Teprotumumab (Antibody 1)

The following are the data obtained from the follow-up of patients seven weeks after completion of treatment.

TABLE 6

Proportion of Responders by Treatment Group and Visit
Imputation for Subjects Receiving TED During Follow-up
ITT Population - Including Week 24 Responders on Primary Endpoint

| Week<br>Statistics | Placebo<br>(N = 9) | RV 001<br>(N = 29) |
|---|---|---|
| Week 28 | | |
| Responder [1] | 5 (55.6%) | 27 (93.1%) |
| Non-Responder | 4 (44.4%) | 2 (6.9%) |
| Total | 9 (100%) | 29 (100%) |
| Chi-square Test [2]: | | |
| Difference | | 37.5% |
| 95% CI | | (3.8%, 71.3%) |
| P-value | | 0.007 |
| Week 72 | | |
| Responder [1] | 5 (55.6%) | 15 (51.7%) |
| Non-Responder | 4 (44.4%) | 14 (48.3%) |
| Total | 9 (100%) | 29 (100%) |
| Chi-square Test [2]: | | |
| Difference | | −3.8% |
| 95% CI | | (−41.0%, 33.4%) |
| P-value | | 0.841 |

Note:

Subjects who received TED treatment in the follow-up were treated as non-responders from the time of TED treatment forward.

[1] Responders are defined as subjects who had a reduction in CAS of >=2 points AND reduction in proptosis of >=2 mm in the study eye and no deterioration (increase in CAS of >=2 points or increase in proptosis of >=2 mm) in the non-study eye.

[2] Chi square test comparing Responder vs. Non-Responder. Difference = responder proportion in RV 001 group − responder proportion in Placebo group.

TABLE 7

Proportion of Responders by Treatment Group and Visit (Study Eye)
Imputation for Subjects Receiving TED During Follow-up
(ITT Population)

| Week<br>Statistics | Placebo<br>(N = 45) | RV 001<br>(N = 42) |
|---|---|---|
| Week 6 | | |
| Responder [1] | 2 (4.4%) | 18 (42.9%) |
| Non-Responder/Missing | 43 (95.6%) | 24 (57.1%) |
| Total | 45 (100%) | 42 (100%) |
| Chi-square Test [2]: | | |
| Difference | | 38.4% |
| 95% CI | | (22.3%, 54.5%) |
| P-value | | <0.001 |
| Week 12 | | |
| Responder [1] | 2 (4.4%) | 23 (54.8%) |
| Non-Responder/Missing | 43 (95.6%) | 19 (45.2%) |
| Total | 45 (100%) | 42 (100%) |
| Chi-square Test [2]: | | |
| Difference | | 50.3% |
| 95% CI | | (34.1%, 66.5%) |
| P-value | | <0.001 |
| Week 18 | | |
| Responder [1] | 2 (4.4%) | 30 (71.4%) |
| Non-Responder/Missing | 43 (95.6%) | 12 (28.6%) |
| Total | 45 (100%) | 42 (100%) |
| Chi-square Test [2]: | | |
| Difference | | 67.0% |
| 95% CI | | (52.1%, 81.9%) |
| P-value | | <0.001 |
| Week 24 | | |
| Responder [1] | 9 (20.0%) | 29 (69.0%) |
| Non-Responder/Missing | 36 (80.0%) | 13 (31.0%) |
| Total | 45 (100%) | 42 (100%) |
| Chi-square Test [2]: | | |
| Difference | | 49.0% |
| 95% CI | | (30.8%, 67.3%) |
| P-value | | <0.001 |
| Week 28 | | |
| Responder [1] | 6 (13.3%) | 31 (73.8%) |
| Non-Responder/Missing | 39 (86.7%) | 11 (26.2%) |
| Total | 45 (100%) | 42 (100%) |
| Chi-square Test [2]: | | |
| Difference | | 60.5% |
| 95% CI | | (43.9%, 77.1%) |
| P-value | | <0.001 |
| Week 72 | | |
| Responder [1] | 10 (22.2%) | 19 (45.2%) |
| Non-Responder/Missing | 35 (77.8%) | 23 (54.8%) |
| Total | 45 (100%) | 42 (100%) |

TABLE 7-continued

Proportion of Responders by Treatment Group and Visit (Study Eye) Imputation for Subjects Receiving TED During Follow-up (ITT Population)

| Week<br>Statistics | Placebo<br>(N = 45) | RV 001<br>(N = 42) |
|---|---|---|
| Chi-square Test [2]: | | |
| Difference | | 23.0% |
| 95% CI | | (3.7%, 42.4%) |
| P-value | | 0.023 |

Note:

Subjects who received TED treatment in the follow-up were treated as non-responders from the time of TED treatment forward.

[1] Responders are defined as subjects who had a reduction in CAS of >=2 points AND reduction in proptosis of >=2 mm in the study eye and no deterioration (increase in CAS of >=2 points or increase in proptosis of >=2 mm) in the non-study eye.

[2] Chi square test comparing Responder vs. Non-Responder. Difference = responder proportion in RV 001 group − responder proportion in Placebo group.

TABLE 8

Proportion of Proptosis Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Study Eye | | |
| Week 6 | | |
| Responder [1] | 4 (8.9%) | 22 (52.4%) |
| Other | 41 (91.1%) | 20 (47.6%) |
| Chi-square Test [2]: | | |
| Difference | | 43.5% |
| 95% CI | | (26.3%, 60.7%) |
| P-value | | <0.001 |
| Week 12 | | |
| Responder [1] | 2 (4.4%) | 24 (57.1%) |
| Other | 43 (95.6%) | 18 (42.9%) |
| Chi-square Test [2]: | | |
| Difference | | 52.7% |
| 95% CI | | (36.6%, 68.8%) |
| P-value | | <0.001 |
| Week 18 | | |
| Responder [1] | 4 (8.9%) | 32 (76.2%) |
| Other | 41 (91.1%) | 10 (23.8%) |
| Chi-square Test [2]: | | |
| Difference | | 67.3% |
| 95% CI | | (52.0%, 82.6%) |
| P-value | | <0.001 |
| Week 24 | | |
| Responder [1] | 9 (20.0%) | 30 (71.4%) |
| Other | 36 (80.0%) | 12 (28.6%) |
| Chi-square Test [2]: | | |
| Difference | | 51.4% |
| 95% CI | | (33.4%, 69.4%) |
| P-value | | <0.001 |
| Week 28 | | |
| Responder [1] | 6 (13.3%) | 31 (73.8%) |
| Other | 39 (86.7%) | 11 (26.2%) |
| Chi-square Test [2]: | | |
| Difference | | 60.5% |
| 95% CI | | (43.9%, 77.1%) |
| P-value | | <0.001 |

TABLE 8-continued

Proportion of Proptosis Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Week 72 | | |
| Responder [1] | 10 (22.2%) | 19 (45.2%) |
| Other | 35 (77.8%) | 23 (54.8%) |
| Chi-square Test [2]: | | |
| Difference | | 23.0% |
| 95% CI | | (3.7%, 42.4%) |
| P-value | | 0.023 |
| Non-Study Eye | | |
| Week 6 | | |
| Responder [1] | 3 (6.7%) | 9 (21.4%) |
| Other | 42 (93.3%) | 33 (78.6%) |
| Chi-square Test [2]: | | |
| Difference | | 14.8% |
| 95% CI | | (0.4%, 29.2%) |
| P-value | | 0.046 |
| Week 12 | | |
| Responder [1] | 3 (6.7%) | 15 (35.7%) |
| Other | 42 (93.3%) | 27 (64.3%) |
| Chi-square Test [2]: | | |
| Difference | | 29.0% |
| 95% CI | | (12.8%, 45.3%) |
| P-value | | 0.001 |
| Week 18 | | |
| Responder [1] | 4 (8.9%) | 21 (50.0%) |
| Other | 41 (91.1%) | 21 (50.0%) |
| Chi-square Test [2]: | | |
| Difference | | 41.1% |
| 95% CI | | (23.9%, 58.4%) |
| P-value | | <0.001 |
| Week 24 | | |
| Responder [1] | 6 (13.3%) | 26 (61.9%) |
| Other | 39 (86.7%) | 16 (38.1%) |
| Chi-square Test [2]: | | |
| Difference | | 48.6% |
| 95% CI | | (30.8%, 66.3%) |
| P-value | | <0.001 |
| Week 28 | | |
| Responder [1] | 5 (11.1%) | 23 (54.8%) |
| Other | 40 (88.9%) | 19 (45.2%) |
| Chi-square Test [2]: | | |
| Difference | | 43.7% |
| 95% CI | | (26.0%, 61.3%) |
| P-value | | <0.001 |
| Week 72 | | |
| Responder [1] | 7 (15.6%) | 13 (31.0%) |
| Other | 38 (84.4%) | 29 (69.0%) |

TABLE 8-continued

Proportion of Proptosis Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Chi-square Test [2]: | | |
| Difference | | 15.4% |
| 95% CI | | (−2.1%, 32.9%) |
| P-value | | 0.088 |

Note:

Subjects who received TED treatment in the follow-up were treated as non-responders from the time of TED treatment forward.

[1] Responder is defined as a reduction in proptosis of >=2 mm from baseline.

[2] Chi square test comparing Responder vs. Other (Stable, Worsening, or Missing/Drop Out). Difference = responder proportion in RV 001 group − responder proportion in Placebo group.

TABLE 9

Proportion of CAS Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Study Eye | | |
| Week 6 | | |
| Responder [1] | 13 (28.9%) | 33 (78.6%) |
| Other | 32 (71.1%) | 9 (21.4%) |
| Chi-square Test [2]: | | |
| Difference | | 49.7% |
| 95% CI | | (31.5%, 67.8%) |
| P-value | | <0.001 |
| Week 12 | | |
| Responder [1] | 26 (57.8%) | 38 (90.5%) |
| Other | 19 (42.2%) | 4 (9.5%) |
| Chi-square Test [2]: | | |
| Difference | | 32.7% |
| 95% CI | | (15.8%, 49.6%) |
| P-value | | 0.001 |
| Week 18 | | |
| Responder [1] | 26 (57.8%) | 36 (85.7%) |
| Other | 19 (42.2%) | 6 (14.3%) |
| Chi-square Test [2]: | | |
| Difference | | 27.9% |
| 95% CI | | (10.0%, 45.8%) |
| P-value | | 0.004 |
| Week 24 | | |
| Responder [1] | 28 (62.2%) | 37 (88.1%) |
| Other | 17 (37.8%) | 5 (11.9%) |
| Chi-square Test [2]: | | |
| Difference | | 25.9% |
| 95% CI | | (8.7%, 43.1%) |
| P-value | | 0.006 |
| Week 28 | | |
| Responder [1] | 27 (60.0%) | 37 (88.1%) |
| Other | 18 (40.0%) | 5 (11.9%) |

TABLE 9-continued

Proportion of CAS Response by Treatment Group and Visit - Responder versus Other Imputation for Subjects Receiving TED During Follow-up (ITT Population)

| Eye<br>Week<br>Statistics | Placebo<br>(N = 45) | RV 001<br>(N = 42) |
|---|---|---|
| Chi-square Test [2]: | | |
| Difference | | 28.1% |
| 95% CI | | (10.8%, 45.4%) |
| P-value | | 0.003 |
| Week 72 | | |
| Responder [1] | 31 (68.9%) | 29 (69.0%) |
| Other | 14 (31.1%) | 13 (31.0%) |
| Chi-square Test [2]: | | |
| Difference | | 0.2% |
| 95% CI | | (−19.3%, 19.6%) |
| P-value | | 0.987 |
| Non-Study Eye | | |
| Week 6 | | |
| Responder [1] | 14 (31.1%) | 29 (69.0%) |
| Other | 31 (68.9%) | 13 (31.0%) |
| Chi-square Test [2]: | | |
| Difference | | 37.9% |
| 95% CI | | (18.5%, 57.4%) |
| P-value | | <0.001 |
| Week 12 | | |
| Responder [1] | 18 (40.0%) | 32 (76.2%) |
| Other | 27 (60.0%) | 10 (23.8%) |
| Chi-square Test [2]: | | |
| Difference | | 36.2% |
| 95% CI | | (16.9%, 55.4%) |
| P-value | | 0.001 |
| Week 18 | | |
| Responder [1] | 23 (51.1%) | 31 (73.8%) |
| Other | 22 (48.9%) | 11 (26.2%) |
| Chi-square Test [2]: | | |
| Difference | | 22.7% |
| 95% CI | | (2.9%, 42.4%) |
| P-value | | 0.029 |
| Week 24 | | |
| Responder [1] | 22 (48.9%) | 32 (76.2%) |
| Other | 23 (51.1%) | 10 (23.8%) |
| Chi-square Test [2]: | | |
| Difference | | 27.3% |
| 95% CI | | (7.8%, 46.8%) |
| P-value | | 0.009 |
| Week 28 | | |
| Responder [1] | 20 (44.4%) | 32 (76.2%) |
| Other | 25 (55.6%) | 10 (23.8%) |
| Chi-square Test [2]: | | |
| Difference | | 31.7% |
| 95% CI | | (12.3%, 51.2%) |
| P-value | | 0.003 |
| Week 72 | | |
| Responder [1] | 26 (57.8%) | 26 (61.9%) |
| Other | 19 (42.2%) | 16 (38.1%) |

TABLE 9-continued

| Proportion of CAS Response by Treatment Group and Visit - Responder versus Other Imputation for Subjects Receiving TED During Follow-up (ITT Population) | | |
|---|---|---|
| Eye<br>Week<br>Statistics | Placebo<br>(N = 45) | RV 001<br>(N = 42) |
| Chi-square Test [2]: | | |
| Difference | | 4.1% |
| 95% CI | | (−16.5%, 24.7%) |
| P-value | | 0.695 |

Abbreviation:
CAS = Clinical Activity Score (7 point scale).
Note:
Subjects who received TED treatment in the follow-up were treated as non-responders from the time of TED treatment forward.
[1] Responder is defined as decrease of 2 points or more from baseline.
[2] Chi square test comparing Responder vs. Other (Stable, Worsening, or Missing/Drop Out). Difference = responder proportion in RV 001 group − responder proportion in Placebo group.

TABLE 10

| Summary of Individual CAS Component by Treatment (ITT Population) | | |
|---|---|---|
| Percent of Subjects with Symptom | Placebo<br>N = 45 | RV 001<br>N = 42 |
| SPONTANEOUS ORBITAL PAIN | | |
| BASELINE | 31/45 (68.89%) | 31/42 (73.81%) |
| P-value (Chi-squared with correction) | | 0.78735 |
| P-value (Chi-squared w/o correction) | | 0.61229 |
| P-value (Fisher Exact) | | 0.64307 |
| Week 6 | 19/42 (45.24%) | 15/41 (36.59%) |
| P-value (Chi-squared with correction) | | 0.56312 |
| P-value (Chi-squared w/o correction) | | 0.42288 |
| P-value (Fisher Exact) | | 0.50517 |
| Week 12 | 15/41 (36.59%) | 5/40 (12.5%) |
| P-value (Chi-squared with correction) | | 0.02410 |
| P-value (Chi-squared w/o correction) | | 0.01196 |
| P-value (Fisher Exact) | | 0.01925 |
| Week 18 | 17/41 (41.46%) | 3/39 (7.69%) |
| P-value (Chi-squared with correction) | | 0.00124 |
| P-value (Chi-squared w/o correction) | | 0.00049 |
| P-value (Fisher Exact) | | 0.00061 |
| Week 24 | 8/39 (20.51%) | 2/38 (5.26%) |
| P-value (Chi-squared with correction) | | 0.09871 |
| P-value (Chi-squared w/o correction) | | 0.04657 |
| P-value (Fisher Exact) | | 0.08661 |
| Week 28 | 11/37 (29.73%) | 2/37 (5.41%) |
| P-value (Chi-squared with correction) | | 0.01453 |
| P-value (Chi-squared w/o correction) | | 0.00597 |
| P-value (Fisher Exact) | | 0.01226 |
| Week 72 | 5/32 (15.62%) | 7/33 (21.21%) |
| P-value (Chi-squared with correction) | | 0.79432 |
| P-value (Chi-squared w/o correction) | | 0.56163 |
| P-value (Fisher Exact) | | 0.75082 |
| GAZE EVOKED ORBITAL PAIN | | |
| BASELINE | 35/45 (77.78%) | 32/42 (76.19%) |
| P-value (Chi-squared with correction) | | 1.00000 |
| P-value (Chi-squared w/o correction) | | 0.86043 |
| P-value (Fisher Exact) | | 1.00000 |
| Week 6 | 22/42 (52.38%) | 15/41 (36.59%) |
| P-value (Chi-squared with correction) | | 0.21996 |
| P-value (Chi-squared w/o correction) | | 0.14776 |
| P-value (Fisher Exact) | | 0.18697 |
| Week 12 | 14/41 (34.15%) | 8/40 (20%) |
| P-value (Chi-squared with correction) | | 0.23749 |
| P-value (Chi-squared w/o correction) | | 0.15240 |
| P-value (Fisher Exact) | | 0.21224 |
| Week 18 | 14/41 (34.15%) | 6/39 (15.38%) |
| P-value (Chi-squared with correction) | | 0.09319 |
| P-value (Chi-squared w/o correction) | | 0.05273 |
| P-value (Fisher Exact) | | 0.07145 |

TABLE 10-continued

| Summary of Individual CAS Component by Treatment (ITT Population) | | |
|---|---|---|
| Percent of Subjects with Symptom | Placebo N = 45 | RV 001 N = 42 |
| Week 24 | 14/39 (35.9%) | 4/38 (10.53%) |
| P-value (Chi-squared with correction) | | 0.01824 |
| P-value (Chi-squared w/o correction) | | 0.00854 |
| P-value (Fisher Exact) | | 0.01412 |
| Week 28 | 14/37 (37.84%) | 4/37 (10.81%) |
| P-value (Chi-squared with correction) | | 0.01475 |
| P-value (Chi-squared w/o correction) | | 0.00674 |
| P-value (Fisher Exact) | | 0.01336 |
| Week 72 | 6/32 (18.75%) | 3/33 (9.09%) |
| P-value (Chi-squared with correction) | | 0.44245 |
| P-value (Chi-squared w/o correction) | | 0.25965 |
| P-value (Fisher Exact) | | 0.30339 |
| EYELID SWELLING | | |
| BASELINE | 45/45 (100%) | 40/42 (95.24%) |
| P-value (Chi-squared with correction) | | 0.44417 |
| P-value (Chi-squared w/o correction) | | 0.13861 |
| P-value (Fisher Exact) | | 0.23015 |
| Week 6 | 37/42 (88.1%) | 26/41 (63.41%) |
| P-value (Chi-squared with correction) | | 0.01770 |
| P-value (Chi-squared w/o correction) | | 0.00857 |
| P-value (Fisher Exact) | | 0.01067 |
| Week 12 | 33/41 (80.49%) | 21/40 (52.5%) |
| P-value (Chi-squared with correction) | | 0.01486 |
| P-value (Chi-squared w/o correction) | | 0.00755 |
| P-value (Fisher Exact) | | 0.00978 |
| Week 18 | 33/41 (80.49%) | 17/39 (43.59%) |
| P-value (Chi-squared with correction) | | 0.00149 |
| P-value (Chi-squared w/o correction) | | 0.00066 |
| P-value (Fisher Exact) | | 0.00107 |
| Week 24 | 27/39 (69.23%) | 11/38 (28.95%) |
| P-value (Chi-squared with correction) | | 0.00094 |
| P-value (Chi-squared w/o correction) | | 0.00041 |
| P-value (Fisher Exact) | | 0.00059 |
| Week 28 | 27/37 (72.97%) | 9/37 (24.32%) |
| P-value (Chi-squared with correction) | | 0.00008 |
| P-value (Chi-squared w/o correction) | | 0.00003 |
| P-value (Fisher Exact) | | 0.00006 |
| Week 72 | 16/32 (50%) | 9/33 (27.27%) |
| P-value (Chi-squared with correction) | | 0.10353 |
| P-value (Chi-squared w/o correction) | | 0.05971 |
| P-value (Fisher Exact) | | 0.07692 |
| EYELID ERYTHEMA | | |
| BASELINE | 27/45 (60%) | 17/42 (40.48%) |
| P-value (Chi-squared with correction) | | 0.10838 |
| P-value (Chi-squared w/o correction) | | 0.06874 |
| P-value (Fisher Exact) | | 0.08744 |
| Week 6 | 20/42 (47.62%) | 8/41 (19.51%) |
| P-value (Chi-squared with correction) | | 0.01330 |
| P-value (Chi-squared w/o correction) | | 0.00677 |
| P-value (Fisher Exact) | | 0.01024 |
| Week 12 | 12/41 (29.27%) | 4/40 (10%) |
| P-value (Chi-squared with correction) | | 0.05762 |
| P-value (Chi-squared w/o correction) | | 0.02943 |
| P-value (Fisher Exact) | | 0.04884 |
| Week 18 | 12/41 (29.27%) | 3/39 (7.69%) |
| P-value (Chi-squared with correction) | | 0.02890 |
| P-value (Chi-squared w/o correction) | | 0.01346 |
| P-value (Fisher Exact) | | 0.02045 |
| Week 24 | 10/39 (25.64%) | 2/38 (5.26%) |
| P-value (Chi-squared with correction) | | 0.03151 |
| P-value (Chi-squared w/o correction) | | 0.01371 |
| P-value (Fisher Exact) | | 0.02488 |
| Week 28 | 7/37 (18.92%) | 1/37 (2.7%) |
| P-value (Chi-squared with correction) | | 0.06123 |
| P-value (Chi-squared w/o correction) | | 0.02469 |
| P-value (Fisher Exact) | | 0.05567 |
| Week 72 | 2/32 (6.25%) | 2/33 (6.06%) |
| P-value (Chi-squared with correction) | | 1.00000 |
| P-value (Chi-squared w/o correction) | | 0.97466 |
| P-value (Fisher Exact) | | 1.00000 |

TABLE 10-continued

Summary of Individual CAS Component by Treatment (ITT Population)

| Percent of Subjects with Symptom | Placebo N = 45 | RV 001 N = 42 |
|---|---|---|
| CONJUNCTIVAL REDNESS | | |
| BASELINE | 42/45 (93.33%) | 40/42 (95.24%) |
| P-value (Chi-squared with correction) | | 1.00000 |
| P-value (Chi-squared w/o correction) | | 0.70287 |
| P-value (Fisher Exact) | | 1.00000 |
| Week 6 | 33/42 (78.57%) | 21/41 (51.22%) |
| P-value (Chi-squared with correction) | | 0.01718 |
| P-value (Chi-squared w/o correction) | | 0.00897 |
| P-value (Fisher Exact) | | 0.01163 |
| Week 12 | 30/41 (73.17%) | 17/40 (42.5%) |
| P-value (Chi-squared with correction) | | 0.01013 |
| P-value (Chi-squared w/o correction) | | 0.00517 |
| P-value (Fisher Exact) | | 0.00698 |
| Week 18 | 21/41 (51.22%) | 13/39 (33.33%) |
| P-value (Chi-squared with correction) | | 0.16412 |
| P-value (Chi-squared w/o correction) | | 0.10575 |
| P-value (Fisher Exact) | | 0.11939 |
| Week 24 | 19/39 (48.72%) | 12/38 (31.58%) |
| P-value (Chi-squared with correction) | | 0.19333 |
| P-value (Chi-squared w/o correction) | | 0.12523 |
| P-value (Fisher Exact) | | 0.16461 |
| Week 28 | 17/37 (45.95%) | 7/37 (18.92%) |
| P-value (Chi-squared with correction) | | 0.02542 |
| P-value (Chi-squared w/o correction) | | 0.01302 |
| P-value (Fisher Exact) | | 0.02438 |
| Week 72 | 9/32 (28.12%) | 13/33 (39.39%) |
| P-value (Chi-squared with correction) | | 0.48534 |
| P-value (Chi-squared w/o correction) | | 0.33711 |
| P-value (Fisher Exact) | | 0.43386 |
| CHEMOSIS | | |
| BASELINE | 30/45 (66.67%) | 25/42 (59.52%) |
| P-value (Chi-squared with correction) | | 0.63982 |
| P-value (Chi-squared w/o correction) | | 0.48994 |
| P-value (Fisher Exact) | | 0.51306 |
| Week 6 | 25/42 (59.52%) | 9/41 (21.95%) |
| P-value (Chi-squared with correction) | | 0.00113 |
| P-value (Chi-squared w/o correction) | | 0.00050 |
| P-value (Fisher Exact) | | 0.00074 |
| Week 12 | 18/41 (43.9%) | 6/40 (15%) |
| P-value (Chi-squared with correction) | | 0.00919 |
| P-value (Chi-squared w/o correction) | | 0.00440 |
| P-value (Fisher Exact) | | 0.00689 |
| Week 18 | 17/41 (41.46%) | 4/39 (10.26%) |
| P-value (Chi-squared with correction) | | 0.00354 |
| P-value (Chi-squared w/o correction) | | 0.00152 |
| P-value (Fisher Exact) | | 0.00202 |
| Week 24 | 13/39 (33.33%) | 3/38 (7.89%) |
| P-value (Chi-squared with correction) | | 0.01352 |
| P-value (Chi-squared w/o correction) | | 0.00595 |
| P-value (Fisher Exact) | | 0.01005 |
| Week 28 | 13/37 (35.14%) | 3/37 (8.11%) |
| P-value (Chi-squared with correction) | | 0.01104 |
| P-value (Chi-squared w/o correction) | | 0.00475 |
| P-value (Fisher Exact) | | 0.00955 |
| Week 72 | 4/32 (12.5%) | 4/33 (12.12%) |
| P-value (Chi-squared with correction) | | 1.00000 |
| P-value (Chi-squared w/o correction) | | 0.96293 |
| P-value (Fisher Exact) | | 1.00000 |
| INFLAMMATION OF CARUNCLE OR PLICA | | |
| BASELINE | 26/45 (57.78%) | 28/42 (66.67%) |
| P-value (Chi-squared with correction) | | 0.52689 |
| P-value (Chi-squared w/o correction) | | 0.39319 |
| P-value (Fisher Exact) | | 0.50771 |
| Week 6 | 20/42 (47.62%) | 11/41 (26.83%) |
| P-value (Chi-squared with correction) | | 0.08351 |
| P-value (Chi-squared w/o correction) | | 0.05028 |
| P-value (Fisher Exact) | | 0.06967 |
| Week 12 | 18/41 (43.9%) | 8/40 (20%) |
| P-value (Chi-squared with correction) | | 0.03885 |
| P-value (Chi-squared w/o correction) | | 0.02124 |
| P-value (Fisher Exact) | | 0.03167 |

TABLE 10-continued

| Summary of Individual CAS Component by Treatment (ITT Population) | | |
|---|---|---|
| Percent of Subjects with Symptom | Placebo N = 45 | RV 001 N = 42 |
| Week 18 | 14/41 (34.15%) | 8/39 (20.51%) |
| P-value (Chi-squared with correction) | | 0.26503 |
| P-value (Chi-squared w/o correction) | | 0.17223 |
| P-value (Fisher Exact) | | 0.21440 |
| Week 24 | 12/39 (30.77%) | 5/38 (13.16%) |
| P-value (Chi-squared with correction) | | 0.11229 |
| P-value (Chi-squared w/o correction) | | 0.06249 |
| P-value (Fisher Exact) | | 0.09814 |
| Week 28 | 11/37 (29.73%) | 3/37 (8.11%) |
| P-value (Chi-squared with correction) | | 0.03774 |
| P-value (Chi-squared w/o correction) | | 0.01757 |
| P-value (Fisher Exact) | | 0.03515 |
| Week 72 | 5/32 (15.62%) | 2/33 (6.06%) |
| P-value (Chi-squared with correction) | | 0.39898 |
| P-value (Chi-squared w/o correction) | | 0.21364 |
| P-value (Fisher Exact) | | 0.25756 |

Note:
Subjects who received TED treatment in the follow-up were removed from summary statistics from the time of TED treatment forward.

TABLE 11

| Individual CSS by Treatment Group and Visit - Lid Aperture (mm) Imputation for Subjects Receiving TED During Follow-up (ITT Population) | | |
|---|---|---|
| | Placebo | RV 001 |
| Study Eye | 45 | 42 |
| BASELINE | | |
| n | 45 | 42 |
| Mean (SD) | 11.13 (1.832) | 11.79 (2.618) |
| Median | 11 | 11 |
| Q 1, Q3 | 10.00, 12.00 | 10.00, 13.00 |
| Min, Max | 6.00, 15.00 | 8.00, 19.00 |
| WEEK 6 | | |
| n | 42 | 39 |
| Mean (SD) | 10.99 (1.930) | 11.59 (1.929) |
| Median | 11 | 11 |
| Q 1, Q 3 | 10.00, 12.00 | 10.00, 13.00 |
| Min, Max | 7.00, 16.00 | 8.00, 16.00 |
| CSS responder | 7 (15.6%) | 9 (21.4%) |
| CSS non-responder | 35 (77.8%) | 30 (71.4%) |
| Missing | 3 (6.7%) | 3 (7.1%) |
| Missing as non-responder | 38 (84.4%) | 33 (78.6%) |
| P-value Responder vs. non-responder | | 0.469 |
| P-value Responder vs. non-responder/Missing | | 0.4798 |
| WEEK 12 | | |
| n | 41 | 39 |
| Mean (SD) | 10.89 (1.679) | 11.32 (1.921) |
| Median | 11 | 11 |
| Q 1, Q 3 | 10.00, 12.00 | 10.00, 12.00 |
| Min, Max | 7.00, 15.00 | 8.00, 16.00 |
| CSS responder | 2 (4.4%) | 11 (26.2%) |
| CSS non-responder | 39 (86.7%) | 28 (66.7%) |
| Missing | 4 (8.9%) | 3 (7.1%) |
| Missing as non-responder | 43 (95.6%) | 31 (73.8%) |
| P-value Responder vs. non-responder | | 0.0047 |
| P-value Responder vs. non-responder/Missing | | 0.0045 |
| WEEK 18 | | |
| n | 41 | 39 |
| Mean (SD) | 10.80 (2.185) | 11.33 (1.733) |
| Median | 11 | 11 |
| Q 1, Q 3 | 9.50, 12.00 | 10.00, 12.00 |
| Min, Max | 4.50, 17.00 | 8.00, 16.00 |

TABLE 11-continued

| Individual CSS by Treatment Group and Visit - Lid Aperture (mm) Imputation for Subjects Receiving TED During Follow-up (ITT Population) | | |
|---|---|---|
| | Placebo | RV 001 |
| CSS responder | 6 (13.3%) | 10 (23.8%) |
| CSS non-responder | 35 (77.8%) | 29 (69.0%) |
| Missing | 4 (8.9%) | 3 (7.1%) |
| Missing as non-responder | 39 (86.7%) | 32 (76.2%) |
| P-value Responder vs. non-responder | | 0.2186 |
| P-value Responder vs. non-responder/Missing | | 0.2075 |
| WEEK 24 | | |
| n | 39 | 38 |
| Mean (SD) | 10.82 (2.293) | 11.32 (1.940) |
| Median | 11 | 11 |
| Q 1, Q 3 | 9.50, 12.00 | 10.00, 12.00 |
| Min, Max | 5.00, 17.00 | 8.00, 16.00 |
| CSS responder | 5 (11.1%) | 11 (26.2%) |
| CSS non-responder | 34 (75.6%) | 27 (64.3%) |
| Missing | 6 (13.3%) | 4 (9.5%) |
| Missing as non-responder | 40 (88.9%) | 31 (73.8%) |
| P-value Responder vs. non-responder | | 0.0812 |
| P-value Responder vs. non-responder/Missing | | 0.0696 |
| WEEK 28 | | |
| n | 36 | 36 |
| Mean (SD) | 11.06 (1.941) | 11.29 (1.987) |
| Median | 11 | 11 |
| Q 1, Q 3 | 10.00, 12.00 | 10.00, 12.00 |
| Min, Max | 6.50, 17.00 | 8.00, 15.00 |
| CSS responder | 7 (15.6%) | 13 (31.0%) |
| CSS non-responder | 31 (68.9%) | 23 (54.8%) |
| Missing | 7 (15.6%) | 6 (14.3%) |
| Missing as non-responder | 38 (84.4%) | 29 (69.0%) |
| P-value Responder vs. non-responder | | 0.0868 |
| P-value Responder vs. non-responder/Missing | | 0.0881 |
| WEEK 72 | | |
| n | 32 | 33 |
| Mean (SD) | 10.31 (1.759) | 11.39 (1.758) |
| Median | 10 | 11.5 |
| Q 1, Q 3 | 9.00, 12.00 | 10.00, 12.00 |
| Min, Max | 6.50, 14.00 | 9.00, 16.00 |

TABLE 11-continued

Individual CSS by Treatment Group and Visit - Lid Aperture (mm) Imputation for Subjects Receiving TED During Follow-up (ITT Population)

| | Placebo | RV 001 |
|---|---|---|
| CSS responder | 5 (11.1%) | 12 (28.6%) |
| CSS non-responder | 33 (73.3%) | 25 (59.5%) |
| Missing | 7 (15.6%) | 5 (11.9%) |
| Missing as non-responder | 40 (88.9%) | 30 (71.4%) |
| P-value Responder vs. non-responder | | 0.0462 |
| P-value Responder vs. non-responder/Missing | | 0.0401 |
| Non-study Eye | 45 | 42 |
| BASELINE | | |
| n | 45 | 42 |
| Mean (SD) | 10.42 (1.481) | 10.87 (2.387) |
| Median | 10 | 10 |
| Q 1, Q 3 | 10.00, 11.00 | 9.00, 12.00 |
| Min, Max | 7.00, 15.00 | 8.00, 19.00 |
| WEEK 6 | | |
| n | 42 | 39 |
| Mean (SD) | 10.45 (1.521) | 10.74 (1.870) |
| Median | 10 | 11 |
| Q 1, Q 3 | 9.00, 11.00 | 9.00, 12.00 |
| Min, Max | 8.00, 15.00 | 8.00, 15.00 |
| CSS responder | 4 (8.9%) | 4 (9.5%) |
| CSS non-responder | 38 (84.4%) | 35 (83.3%) |
| Missing | 3 (6.7%) | 3 (7.1%) |
| Missing as non-responder | 41 (91.1%) | 38 (90.5%) |
| P-value Responder vs. non-responder | | 0.9121 |
| P-value Responder vs. non-responder/Missing | | 0.9184 |
| WEEK 12 | | |
| n | 41 | 39 |
| Mean (SD) | 10.16 (1.489) | 10.90 (2.159) |
| Median | 10 | 11 |
| Q 1, Q 3 | 9.00, 11.00 | 9.00, 12.00 |
| Min, Max | 7.00, 15.00 | 8.00, 17.50 |
| CSS responder | 6 (13.3%) | 5 (11.9%) |
| CSS non-responder | 35 (77.8%) | 34 (81.0%) |
| Missing | 4 (8.9%) | 3 (7.1%) |
| Missing as non-responder | 39 (86.7%) | 37 (88.1%) |
| P-value Responder vs. non-responder | | 0.8139 |
| P-value Responder vs. non-responder/Missing | | 0.8412 |
| WEEK 18 | | |
| n | 41 | 39 |
| Mean (SD) | 10.12 (1.836) | 10.92 (2.047) |
| Median | 10 | 11 |
| Q 1, Q 3 | 9.00, 11.00 | 9.00, 12.00 |
| Min, Max | 4.50, 15.00 | 8.00, 16.00 |
| CSS responder | 7 (15.6%) | 6 (14.3%) |
| CSS non-responder | 34 (75.6%) | 33 (78.6%) |
| Missing | 4 (8.9%) | 3 (7.1%) |
| Missing as non-responder | 38 (84.4%) | 36 (85.7%) |
| P-value Responder vs. non-responder | | 0.8379 |
| P-value Responder vs. non-responder/Missing | | 0.8681 |
| WEEK 24 | | |
| n | 39 | 38 |
| Mean (SD) | 10.18 (2.024) | 10.84 (2.096) |
| Median | 10 | 11 |
| Q 1, Q 3 | 9.00, 11.00 | 9.00, 12.00 |
| Min, Max | 3.00, 15.00 | 7.00, 15.00 |
| CSS responder | 4 (8.9%) | 7 (16.7%) |
| CSS non-responder | 35 (77.8%) | 31 (73.8%) |
| Missing | 6 (13.3%) | 4 (9.5%) |
| Missing as non-responder | 41 (91.1%) | 35 (83.3%) |
| P-value Responder vs. non-responder | | 0.306 |

TABLE 11-continued

Individual CSS by Treatment Group and Visit - Lid Aperture (mm) Imputation for Subjects Receiving TED During Follow-up (ITT Population)

| | Placebo | RV 001 |
|---|---|---|
| P-value Responder vs. non-responder/Missing | | 0.2754 |
| WEEK 28 | | |
| n | 36 | 36 |
| Mean (SD) | 10.26 (1.701) | 11.07 (2.122) |
| Median | 10 | 11 |
| Q 1, Q 3 | 9.00, 11.00 | 9.25, 12.00 |
| Min, Max | 8.00, 15.00 | 8.00, 16.00 |
| CSS responder | 6 (13.3%) | 6 (14.3%) |
| CSS non-responder | 32 (71.1%) | 30 (71.4%) |
| Missing | 7 (15.6%) | 6 (14.3%) |
| Missing as non-responder | 39 (86.7%) | 36 (85.7%) |
| P-value Responder vs. non-responder | | 0.9185 |
| P-value Responder vs. non-responder/Missing | | 0.8976 |
| WEEK 72 | | |
| n | 32 | 33 |
| Mean (SD) | 10.03 (1.502) | 10.95 (1.800) |
| Median | 10 | 11 |
| Q 1, Q 3 | 9.00, 11.00 | 10.00, 11.50 |
| Min, Max | 8.00, 14.00 | 8.50, 15.00 |
| CSS responder | 6 (13.3%) | 5 (11.9%) |
| CSS non-responder | 32 (71.1%) | 32 (76.2%) |
| Missing | 7 (15.6%) | 5 (11.9%) |
| Missing as non-responder | 39 (86.7%) | 37 (88.1%) |
| P-value Responder vs. non-responder | | 0.7806 |
| P-value Responder vs. non-responder/Missing | | 0.8412 |

Note:
Subjects who received TED treatment in the follow-up were removed from summary statistics from the time of TED treatment forward and were analyzed as non-responders.
CSS responders are defined as subjects who experienced a decrease of >=2 mm from baseline.
The p-values are from Chi square tests without continuity correction.

TABLE 12

Individual CSS by Treatment Group and Visit - Swelling of the Eyelids Imputation for Subjects Receiving TED During Follow-up (ITT Population)

| | Placebo | RV 001 |
|---|---|---|
| Study Eye | 45 | 42 |
| BASELINE | | |
| ABSENT | 0 (0.0%) | 2 (4.8%) |
| MILD | 14 (31.1%) | 16 (38.1%) |
| MODERATE | 26 (57.8%) | 24 (57.1%) |
| SEVERE | 5 (11.1%) | 0 (0.0%) |
| Missing | 0 (0.0%) | 0 (0.0%) |
| WEEK 6 | | |
| ABSENT | 4 (8.9%) | 10 (23.8%) |
| MILD | 16 (35.6%) | 24 (57.1%) |
| MODERATE | 17 (37.8%) | 6 (14.3%) |
| SEVERE | 5 (11.1%) | 0 (0.0%) |
| Missing | 3 (6.7%) | 2 (4.8%) |
| CSS responder | 11 (24.4%) | 22 (52.4%) |
| CSS non-responder | 31 (68.9%) | 18 (42.9%) |
| Missing | 3 (6.7%) | 2 (4.8%) |
| Missing as non-responder | 34 (75.6%) | 20 (47.6%) |
| P-value Responder vs. non-responder | | 0.0078 |
| P-value Responder vs. non-responder/Missing | | 0.0073 |

TABLE 12-continued

Individual CSS by Treatment Group and Visit - Swelling of the Eyelids Imputation for Subjects Receiving TED During Follow-up (ITT Population)

| | Placebo | RV 001 |
|---|---|---|
| WEEK 12 | | |
| ABSENT | 6 (13.3%) | 17 (40.5%) |
| MILD | 14 (31.1%) | 19 (45.2%) |
| MODERATE | 17 (37.8%) | 4 (9.5%) |
| SEVERE | 4 (8.9%) | 0 (0.0%) |
| Missing | 4 (8.9%) | 2 (4.8%) |
| CSS responder | 15 (33.3%) | 26 (61.9%) |
| CSS non-responder | 26 (57.8%) | 14 (33.3%) |
| Missing | 4 (8.9%) | 2 (4.8%) |
| Missing as non-responder | 30 (66.7%) | 16 (38.1%) |
| P-value Responder vs. non-responder | | 0.0105 |
| P-value Responder vs. non-responder/Missing | | 0.0076 |
| WEEK 18 | | |
| ABSENT | 6 (13.3%) | 19 (45.2%) |
| MILD | 17 (37.8%) | 19 (45.2%) |
| MODERATE | 15 (33.3%) | 0 (0.0%) |
| SEVERE | 3 (6.7%) | 1 (2.4%) |
| Missing | 4 (8.9%) | 3 (7.1%) |
| CSS responder | 18 (40.0%) | 29 (69.0%) |
| CSS non-responder | 23 (51.1%) | 10 (23.8%) |
| Missing | 4 (8.9%) | 3 (7.1%) |
| Missing as non-responder | 27 (60.0%) | 13 (31.0%) |
| P-value Responder vs. non-responder | | 0.0057 |
| P-value Responder vs. non-responder/Missing | | 0.0066 |
| WEEK 24 | | |
| ABSENT | 9 (20.0%) | 24 (57.1%) |
| MILD | 19 (42.2%) | 12 (28.6%) |
| MODERATE | 8 (17.8%) | 1 (2.4%) |
| SEVERE | 3 (6.7%) | 1 (2.4%) |
| Missing | 6 (13.3%) | 4 (9.5%) |
| CSS responder | 22 (48.9%) | 29 (69.0%) |
| CSS non-responder | 17 (37.8%) | 9 (21.4%) |
| Missing | 6 (13.3%) | 4 (9.5%) |
| Missing as non-responder | 23 (51.1%) | 13 (31.0%) |
| P-value Responder vs. non-responder | | 0.0648 |
| P-value Responder vs. non-responder/Missing | | 0.0564 |
| WEEK 28 | | |
| ABSENT | 8 (17.8%) | 21 (50.0%) |
| MILD | 17 (37.8%) | 14 (33.3%) |
| MODERATE | 12 (26.7%) | 0 (0.0%) |
| SEVERE | 2 (4.4%) | 1 (2.4%) |
| Missing | 6 (13.3%) | 6 (14.3%) |
| CSS responder | 19 (42.2%) | 29 (69.0%) |
| CSS non-responder | 20 (44.4%) | 7 (16.7%) |
| Missing | 6 (13.3%) | 6 (14.3%) |
| Missing as non-responder | 26 (57.8%) | 13 (31.0%) |
| P-value Responder vs. non-responder | | 0.0041 |
| P-value Responder vs. non-responder/Missing | | 0.0119 |
| WEEK 72 | | |
| ABSENT | 14 (31.1%) | 20 (47.6%) |
| MILD | 15 (33.3%) | 12 (28.6%) |
| MODERATE | 8 (17.8%) | 2 (4.8%) |
| SEVERE | 1 (2.2%) | 2 (4.8%) |
| Missing | 7 (15.6%) | 6 (14.3%) |
| CSS responder | 21 (46.7%) | 24 (57.1%) |
| CSS non-responder | 17 (37.8%) | 12 (28.6%) |
| Missing | 7 (15.6%) | 6 (14.3%) |
| Missing as non-responder | 24 (53.3%) | 18 (42.9%) |
| P-value Responder vs. non-responder | | 0.3152 |
| P-value Responder vs. non-responder/Missing | | 0.3285 |
| Non-study Eye | 45 | 42 |

TABLE 12-continued

Individual CSS by Treatment Group and Visit - Swelling of the Eyelids Imputation for Subjects Receiving TED During Follow-up (ITT Population)

| | Placebo | RV 001 |
|---|---|---|
| BASELINE | | |
| ABSENT | 1 (2.2%) | 8 (19.0%) |
| MILD | 21 (46.7%) | 15 (35.7%) |
| MODERATE | 20 (44.4%) | 19 (45.2%) |
| SEVERE | 3 (6.7%) | 0 (0.0%) |
| Missing | 0 (0.0%) | 0 (0.0%) |
| WEEK 6 | | |
| ABSENT | 3 (6.7%) | 17 (40.5%) |
| MILD | 21 (46.7%) | 17 (40.5%) |
| MODERATE | 15 (33.3%) | 6 (14.3%) |
| SEVERE | 3 (6.7%) | 0 (0.0%) |
| Missing | 3 (6.7%) | 2 (4.8%) |
| CSS responder | 9 (20.0%) | 18 (42.9%) |
| CSS non-responder | 33 (73.3%) | 22 (52.4%) |
| Missing | 3 (6.7%) | 2 (4.8%) |
| Missing as non-responder | 36 (80.0%) | 24 (57.1%) |
| P-value Responder vs. non-responder | | 0.0232 |
| P-value Responder vs. non-responder/Missing | | 0.0213 |
| WEEK 12 | | |
| ABSENT | 5 (11.1%) | 22 (52.4%) |
| MILD | 20 (44.4%) | 14 (33.3%) |
| MODERATE | 14 (31.1%) | 4 (9.5%) |
| SEVERE | 2 (4.4%) | 0 (0.0%) |
| Missing | 4 (8.9%) | 2 (4.8%) |
| CSS responder | 13 (28.9%) | 22 (52.4%) |
| CSS non-responder | 28 (62.2%) | 18 (42.9%) |
| Missing | 4 (8.9%) | 2 (4.8%) |
| Missing as non-responder | 32 (71.1%) | 20 (47.6%) |
| P-value Responder vs. non-responder | | 0.0344 |
| P-value Responder vs. non-responder/Missing | | 0.0256 |
| WEEK 18 | | |
| ABSENT | 6 (13.3%) | 21 (50.0%) |
| MILD | 22 (48.9%) | 17 (40.5%) |
| MODERATE | 11 (24.4%) | 1 (2.4%) |
| SEVERE | 2 (4.4%) | 0 (0.0%) |
| Missing | 4 (8.9%) | 3 (7.1%) |
| CSS responder | 13 (28.9%) | 24 (57.1%) |
| CSS non-responder | 28 (62.2%) | 15 (35.7%) |
| Missing | 4 (8.9%) | 3 (7.1%) |
| Missing as non-responder | 32 (71.1%) | 18 (42.9%) |
| P-value Responder vs. non-responder | | 0.0075 |
| P-value Responder vs. non-responder/Missing | | 0.0077 |
| WEEK 24 | | |
| ABSENT | 8 (17.8%) | 25 (59.5%) |
| MILD | 22 (48.9%) | 10 (23.8%) |
| MODERATE | 7 (15.6%) | 3 (7.1%) |
| SEVERE | 2 (4.4%) | 0 (0.0%) |
| Missing | 6 (13.3%) | 4 (9.5%) |
| CSS responder | 18 (40.0%) | 24 (57.1%) |
| CSS non-responder | 21 (46.7%) | 14 (33.3%) |
| Missing | 6 (13.3%) | 4 (9.5%) |
| Missing as non-responder | 27 (60.0%) | 18 (42.9%) |
| P-value Responder vs. non-responder | | 0.1341 |
| P-value Responder vs. non-responder/Missing | | 0.1098 |
| WEEK 28 | | |
| ABSENT | 8 (17.8%) | 23 (54.8%) |
| MILD | 19 (42.2%) | 12 (28.6%) |
| MODERATE | 11 (24.4%) | 1 (2.4%) |
| SEVERE | 1 (2.2%) | 0 (0.0%) |
| Missing | 6 (13.3%) | 6 (14.3%) |
| CSS responder | 15 (33.3%) | 23 (54.8%) |
| CSS non-responder | 24 (53.3%) | 13 (31.0%) |
| Missing | 6 (13.3%) | 6 (14.3%) |
| Missing as non-responder | 30 (66.7%) | 19 (45.2%) |

TABLE 12-continued

Individual CSS by Treatment Group and Visit - Swelling of the Eyelids
Imputation for Subjects Receiving TED During Follow-up
(ITT Population)

| | Placebo | RV 001 |
|---|---|---|
| P-value Responder vs. non-responder | | 0.0278 |
| P-value Responder vs. non-responder/Missing | | 0.044 |
| WEEK 72 | | |
| ABSENT | 16 (35.6%) | 21 (50.0%) |
| MILD | 13 (28.9%) | 12 (28.6%) |
| MODERATE | 8 (17.8%) | 2 (4.8%) |
| SEVERE | 1 (2.2%) | 1 (2.4%) |
| Missing | 7 (15.6%) | 6 (14.3%) |
| CSS responder | 18 (40.0%) | 20 (47.6%) |
| CSS non-responder | 20 (44.4%) | 16 (38.1%) |
| Missing | 7 (15.6%) | 6 (14.3%) |
| Missing as non-responder | 27 (60.0%) | 22 (52.4%) |
| P-value Responder vs. non-responder | | 0.4813 |
| P-value Responder vs. non-responder/Missing | | 0.474 |

Note:

Subjects who received TED treatment in the follow-up were treated as non-responders from the time of TED treatment forward.

CSS responders are defined as subjects who experienced a decrease of >=1 grade.

The p-values are from Chi square tests without continuity correction.

TABLE 13

Individual CSS by Treatment Group and Visit - Conjunctival Edema
Imputation for Subjects Receiving TED During Follow-up
(ITT Population)

| | Placebo | RV 001 |
|---|---|---|
| Study Eye | 45 | 42 |
| BASELINE | | |
| ABSENT | 14 (31.1%) | 17 (40.5%) |
| PRESENT | 31 (68.9%) | 25 (59.5%) |
| Missing | 0 (0.0%) | 0 (0.0%) |
| WEEK 6 | | |
| ABSENT | 15 (33.3%) | 32 (76.2%) |
| PRESENT | 27 (60.0%) | 8 (19.0%) |
| Missing | 3 (6.7%) | 2 (4.8%) |
| CSS responder | 6 (13.3%) | 15 (35.7%) |
| CSS non-responder | 36 (80.0%) | 25 (59.5%) |
| Missing | 3 (6.7%) | 2 (4.8%) |
| Missing as non-responder | 39 (86.7%) | 27 (64.3%) |
| P-value Responder vs. non-responder | | 0.0161 |
| P-value Responder vs. non-responder/Missing | | 0.0148 |
| WEEK 12 | | |
| ABSENT | 21 (46.7%) | 34 (81.0%) |
| PRESENT | 20 (44.4%) | 6 (14.3%) |
| Missing | 4 (8.9%) | 2 (4.8%) |
| CSS responder | 10 (22.2%) | 17 (40.5%) |
| CSS non-responder | 31 (68.9%) | 23 (54.8%) |
| Missing | 4 (8.9%) | 2 (4.8%) |
| Missing as non-responder | 35 (77.8%) | 25 (59.5%) |
| P-value Responder vs. non-responder | | 0.0839 |
| P-value Responder vs. non-responder/Missing | | 0.0659 |
| WEEK 18 | | |
| ABSENT | 21 (46.7%) | 36 (85.7%) |
| PRESENT | 20 (44.4%) | 3 (7.1%) |
| Missing | 4 (8.9%) | 3 (7.1%) |
| CSS responder | 10 (22.2%) | 20 (47.6%) |
| CSS non-responder | 31 (68.9%) | 19 (45.2%) |
| Missing | 4 (8.9%) | 3 (7.1%) |
| Missing as non-responder | 35 (77.8%) | 22 (52.4%) |

TABLE 13-continued

Individual CSS by Treatment Group and Visit - Conjunctival Edema
Imputation for Subjects Receiving TED During Follow-up
(ITT Population)

| | Placebo | RV 001 |
|---|---|---|
| P-value Responder vs. non-responder | | 0.013 |
| P-value Responder vs. non-responder/Missing | | 0.0128 |
| WEEK 24 | | |
| ABSENT | 23 (51.1%) | 35 (83.3%) |
| PRESENT | 16 (35.6%) | 3 (7.1%) |
| Missing | 6 (13.3%) | 4 (9.5%) |
| CSS responder | 12 (26.7%) | 19 (45.2%) |
| CSS non-responder | 27 (60.0%) | 19 (45.2%) |
| Missing | 6 (13.3%) | 4 (9.5%) |
| Missing as non-responder | 33 (73.3%) | 23 (54.8%) |
| P-value Responder vs. non-responder | | 0.0854 |
| P-value Responder vs. non-responder/Missing | | 0.0707 |
| WEEK 28 | | |
| ABSENT | 24 (53.3%) | 33 (78.6%) |
| PRESENT | 15 (33.3%) | 3 (7.1%) |
| Missing | 6 (13.3%) | 6 (14.3%) |
| CSS responder | 12 (26.7%) | 18 (42.9%) |
| CSS non-responder | 27 (60.0%) | 18 (42.9%) |
| Missing | 6 (13.3%) | 6 (14.3%) |
| Missing as non-responder | 33 (73.3%) | 24 (57.1%) |
| P-value Responder vs. non-responder | | 0.0894 |
| P-value Responder vs. non-responder/Missing | | 0.1124 |
| WEEK 72 | | |
| ABSENT | 31 (68.9%) | 34 (81.0%) |
| PRESENT | 7 (15.6%) | 2 (4.8%) |
| Missing | 7 (15.6%) | 6 (14.3%) |
| CSS responder | 16 (35.6%) | 16 (38.1%) |
| CSS non-responder | 22 (48.9%) | 20 (47.6%) |
| Missing | 7 (15.6%) | 6 (14.3%) |
| Missing as non-responder | 29 (64.4%) | 26 (61.9%) |
| P-value Responder vs. non-responder | | 0.8391 |
| P-value Responder vs. non-responder/Missing | | 0.8061 |
| Non-study Eye | 45 | 42 |
| BASELINE | | |
| ABSENT | 17 (37.8%) | 20 (47.6%) |
| PRESENT | 28 (62.2%) | 22 (52.4%) |
| Missing | 0 (0.0%) | 0 (0.0%) |
| WEEK 6 | | |
| ABSENT | 19 (42.2%) | 35 (83.3%) |
| PRESENT | 23 (51.1%) | 5 (11.9%) |
| Missing | 3 (6.7%) | 2 (4.8%) |
| CSS responder | 7 (15.6%) | 15 (35.7%) |
| CSS non-responder | 35 (77.8%) | 25 (59.5%) |
| Missing | 3 (6.7%) | 2 (4.8%) |
| Missing as non-responder | 38 (84.4%) | 27 (64.3%) |
| P-value Responder vs. non-responder | | 0.0333 |
| P-value Responder vs. non-responder/Missing | | 0.0306 |
| WEEK 12 | | |
| ABSENT | 24 (53.3%) | 35 (83.3%) |
| PRESENT | 17 (37.8%) | 5 (11.9%) |
| Missing | 4 (8.9%) | 2 (4.8%) |
| CSS responder | 8 (17.8%) | 15 (35.7%) |
| CSS non-responder | 33 (73.3%) | 25 (59.5%) |
| Missing | 4 (8.9%) | 2 (4.8%) |
| Missing as non-responder | 37 (82.2%) | 27 (64.3%) |
| P-value Responder vs. non-responder | | 0.0727 |
| P-value Responder vs. non-responder/Missing | | 0.058 |
| WEEK 18 | | |
| ABSENT | 24 (53.3%) | 34 (81.0%) |
| PRESENT | 17 (37.8%) | 5 (11.9%) |
| Missing | 4 (8.9%) | 3 (7.1%) |

TABLE 13-continued

Individual CSS by Treatment Group and Visit - Conjunctival Edema Imputation for Subjects Receiving TED During Follow-up (ITT Population)

| | Placebo | RV 001 |
|---|---|---|
| CSS responder | 8 (17.8%) | 15 (35.7%) |
| CSS non-responder | 33 (73.3%) | 24 (57.1%) |
| Missing | 4 (8.9%) | 3 (7.1%) |
| Missing as non-responder | 37 (82.2%) | 27 (64.3%) |
| P-value Responder vs. non-responder | | 0.0612 |
| P-value Responder vs. non-responder/Missing | | 0.058 |
| WEEK 24 | | |
| ABSENT | 26 (57.8%) | 34 (81.0%) |
| PRESENT | 13 (28.9%) | 4 (9.5%) |
| Missing | 6 (13.3%) | 4 (9.5%) |
| CSS responder | 12 (26.7%) | 15 (35.7%) |
| CSS non-responder | 27 (60.0%) | 23 (54.8%) |
| Missing | 6 (13.3%) | 4 (9.5%) |
| Missing as non-responder | 33 (73.3%) | 27 (64.3%) |
| P-value Responder vs. non-responder | | 0.4235 |
| P-value Responder vs. non-responder/Missing | | 0.362 |
| WEEK 28 | | |
| ABSENT | 24 (53.3%) | 32 (76.2%) |
| PRESENT | 15 (33.3%) | 4 (9.5%) |
| Missing | 6 (13.3%) | 6 (14.3%) |
| CSS responder | 10 (22.2%) | 14 (33.3%) |
| CSS non-responder | 29 (64.4%) | 22 (52.4%) |
| Missing | 6 (13.3%) | 6 (14.3%) |
| Missing as non-responder | 35 (77.8%) | 28 (66.7%) |
| P-value Responder vs. non-responder | | 0.2192 |
| P-value Responder vs. non-responder/Missing | | 0.2466 |
| WEEK 72 | | |
| ABSENT | 31 (68.9%) | 31 (73.8%) |
| PRESENT | 7 (15.6%) | 5 (11.9%) |
| Missing | 7 (15.6%) | 6 (14.3%) |
| CSS responder | 14 (31.1%) | 12 (28.6%) |
| CSS non-responder | 24 (53.3%) | 24 (57.1%) |
| Missing | 7 (15.6%) | 6 (14.3%) |
| Missing as non-responder | 31 (68.9%) | 30 (71.4%) |
| P-value Responder vs. non-responder | | 0.752 |
| P-value Responder vs. non-responder/Missing | | 0.7959 |

Note:
Subjects who received TED treatment in the follow-up were treated as non-responders from the time of TED treatment forward.
CSS responders are defined as subjects who experienced a decrease of >=1 grade (changed from Present to Absent).
The p-values are from Chi square tests without continuity correction.

TABLE 14

Individual CSS by Treatment Group and Visit - Subjective Diplopia Score Imputation for Subjects Receiving TED During Follow-up (ITT Population)

| | Placebo | RV 001 |
|---|---|---|
| Study Eye | 45 | 42 |
| BASELINE | | |
| 0, NO DIPLOPIA | 14 (31.1%) | 4 (9.5%) |
| 1, INTERMITTENT | 19 (42.2%) | 16 (38.1%) |
| 2, INCONSTANT | 8 (17.8%) | 7 (16.7%) |
| 3, CONSTANT | 4 (8.9%) | 15 (35.7%) |
| Missing | 0 (0.0%) | 0 (0.0%) |
| WEEK 6 | | |
| 0, NO DIPLOPIA | 18 (40.0%) | 13 (31.0%) |
| 1, INTERMITTENT | 12 (26.7%) | 11 (26.2%) |
| 2, INCONSTANT | 8 (17.8%) | 6 (14.3%) |

TABLE 14-continued

Individual CSS by Treatment Group and Visit - Subjective Diplopia Score Imputation for Subjects Receiving TED During Follow-up (ITT Population)

| | Placebo | RV 001 |
|---|---|---|
| 3, CONSTANT | 4 (8.9%) | 10 (23.8%) |
| Missing | 3 (6.7%) | 2 (4.8%) |
| CSS responder | 9 (20.0%) | 17 (40.5%) |
| CSS non-responder | 33 (73.3%) | 23 (54.8%) |
| Missing | 3 (6.7%) | 2 (4.8%) |
| Missing as non-responder | 36 (80.0%) | 25 (59.5%) |
| P-value Responder vs. non-responder | | 0.0404 |
| P-value Responder vs. non-responder/Missing | | 0.0371 |
| WEEK 12 | | |
| 0, NO DIPLOPIA | 20 (44.4%) | 16 (38.1%) |
| 1, INTERMITTENT | 9 (20.0%) | 8 (19.0%) |
| 2, INCONSTANT | 7 (15.6%) | 9 (21.4%) |
| 3, CONSTANT | 5 (11.1%) | 7 (16.7%) |
| Missing | 4 (8.9%) | 2 (4.8%) |
| CSS responder | 10 (22.2%) | 24 (57.1%) |
| CSS non-responder | 31 (68.9%) | 16 (38.1%) |
| Missing | 4 (8.9%) | 2 (4.8%) |
| Missing as non-responder | 35 (77.8%) | 18 (42.9%) |
| P-value Responder vs. non-responder | | 0.0012 |
| P-value Responder vs. non-responder/Missing | | 0.0009 |
| WEEK 18 | | |
| 0, NO DIPLOPIA | 19 (42.2%) | 16 (38.1%) |
| 1, INTERMITTENT | 9 (20.0%) | 8 (19.0%) |
| 2, INCONSTANT | 8 (17.8%) | 8 (19.0%) |
| 3, CONSTANT | 5 (11.1%) | 7 (16.7%) |
| Missing | 4 (8.9%) | 3 (7.1%) |
| CSS responder | 11 (24.4%) | 23 (54.8%) |
| CSS non-responder | 30 (66.7%) | 16 (38.1%) |
| Missing | 4 (8.9%) | 3 (7.1%) |
| Missing as non-responder | 34 (75.6%) | 19 (45.2%) |
| P-value Responder vs. non-responder | | 0.0036 |
| P-value Responder vs. non-responder/Missing | | 0.0038 |
| WEEK 24 | | |
| 0, NO DIPLOPIA | 18 (40.0%) | 21 (50.0%) |
| 1, INTERMITTENT | 8 (17.8%) | 4 (9.5%) |
| 2, INCONSTANT | 7 (15.6%) | 9 (21.4%) |
| 3, CONSTANT | 6 (13.3%) | 4 (9.5%) |
| Missing | 6 (13.3%) | 4 (9.5%) |
| CSS responder | 10 (22.2%) | 26 (61.9%) |
| CSS non-responder | 29 (64.4%) | 12 (28.6%) |
| Missing | 6 (13.3%) | 4 (9.5%) |
| Missing as non-responder | 35 (77.8%) | 16 (38.1%) |
| P-value Responder vs. non-responder | | 0.0002 |
| P-value Responder vs. non-responder/Missing | | 0.0002 |
| WEEK 28 | | |
| 0, NO DIPLOPIA | 19 (42.2%) | 16 (38.1%) |
| 1, INTERMITTENT | 7 (15.6%) | 6 (14.3%) |
| 2, INCONSTANT | 6 (13.3%) | 10 (23.8%) |
| 3, CONSTANT | 7 (15.6%) | 4 (9.5%) |
| Missing | 6 (13.3%) | 6 (14.3%) |
| CSS responder | 9 (20.0%) | 23 (54.8%) |
| CSS non-responder | 30 (66.7%) | 13 (31.0%) |
| Missing | 6 (13.3%) | 6 (14.3%) |
| Missing as non-responder | 36 (80.0%) | 19 (45.2%) |
| P-value Responder vs. non-responder | | 0.0004 |
| P-value Responder vs. non-responder/Missing | | 0.0008 |
| WEEK 72 | | |
| 0, NO DIPLOPIA | 21 (46.7%) | 20 (47.6%) |
| 1, INTERMITTENT | 7 (15.6%) | 4 (9.5%) |
| 2, INCONSTANT | 5 (11.1%) | 6 (14.3%) |
| 3, CONSTANT | 5 (11.1%) | 6 (14.3%) |
| Missing | 7 (15.6%) | 6 (14.3%) |
| CSS responder | 11 (24.4%) | 21 (50.0%) |

TABLE 14-continued

Individual CSS by Treatment Group and Visit - Subjective Diplopia Score Imputation for Subjects Receiving TED During Follow-up (ITT Population)

| | Placebo | RV 001 |
|---|---|---|
| CSS non-responder | 27 (60.0%) | 15 (35.7%) |
| Missing | 7 (15.6%) | 6 (14.3%) |
| Missing as non-responder | 34 (75.6%) | 21 (50.0%) |
| P-value Responder vs. non-responder | | 0.0108 |
| P-value Responder vs. non-responder/Missing | | 0.0135 |
| Non-study Eye | 45 | 42 |
| BASELINE | | |
| 0, NO DIPLOPIA | 15 (33.3%) | 4 (9.5%) |
| 1, INTERMITTENT | 20 (44.4%) | 16 (38.1%) |
| 2, INCONSTANT | 6 (13.3%) | 7 (16.7%) |
| 3, CONSTANT | 4 (8.9%) | 15 (35.7%) |
| Missing | 0 (0.0%) | 0 (0.0%) |
| WEEK 6 | | |
| 0, NO DIPLOPIA | 19 (42.2%) | 14 (33.3%) |
| 1, INTERMITTENT | 12 (26.7%) | 10 (23.8%) |
| 2, INCONSTANT | 7 (15.6%) | 7 (16.7%) |
| 3, CONSTANT | 4 (8.9%) | 9 (21.4%) |
| Missing | 3 (6.7%) | 2 (4.8%) |
| CSS responder | 9 (20.0%) | 19 (45.2%) |
| CSS non-responder | 33 (73.3%) | 21 (50.0%) |
| Missing | 3 (6.7%) | 2 (4.8%) |
| Missing as non-responder | 36 (80.0%) | 23 (54.8%) |
| P-value Responder vs. non-responder | | 0.0128 |
| P-value Responder vs. non-responder/Missing | | 0.0118 |
| WEEK 12 | | |
| 0, NO DIPLOPIA | 21 (46.7%) | 17 (40.5%) |
| 1, INTERMITTENT | 9 (20.0%) | 8 (19.0%) |
| 2, INCONSTANT | 6 (13.3%) | 10 (23.8%) |
| 3, CONSTANT | 5 (11.1%) | 5 (11.9%) |
| Missing | 4 (8.9%) | 2 (4.8%) |
| CSS responder | 10 (22.2%) | 27 (64.3%) |
| CSS non-responder | 31 (68.9%) | 13 (31.0%) |
| Missing | 4 (8.9%) | 2 (4.8%) |
| Missing as non-responder | 35 (77.8%) | 15 (35.7%) |
| P-value Responder vs. non-responder | | 0.0001 |
| P-value Responder vs. non-responder/Missing | | 0.0001 |
| WEEK 18 | | |
| 0, NO DIPLOPIA | 19 (42.2%) | 16 (38.1%) |
| 1, INTERMITTENT | 9 (20.0%) | 8 (19.0%) |
| 2, INCONSTANT | 8 (17.8%) | 8 (19.0%) |
| 3, CONSTANT | 5 (11.1%) | 7 (16.7%) |
| Missing | 4 (8.9%) | 3 (7.1%) |
| CSS responder | 11 (24.4%) | 23 (54.8%) |
| CSS non-responder | 30 (66.7%) | 16 (38.1%) |
| Missing | 4 (8.9%) | 3 (7.1%) |
| Missing as non-responder | 34 (75.6%) | 19 (45.2%) |
| P-value Responder vs. non-responder | | 0.0036 |
| P-value Responder vs. non-responder/Missing | | 0.0038 |
| WEEK 24 | | |
| 0, NO DIPLOPIA | 18 (40.0%) | 21 (50.0%) |
| 1, INTERMITTENT | 8 (17.8%) | 4 (9.5%) |
| 2, INCONSTANT | 7 (15.6%) | 9 (21.4%) |
| 3, CONSTANT | 6 (13.3%) | 4 (9.5%) |
| Missing | 6 (13.3%) | 4 (9.5%) |
| CSS responder | 10 (22.2%) | 26 (61.9%) |
| CSS non-responder | 29 (64.4%) | 12 (28.6%) |
| Missing | 6 (13.3%) | 4 (9.5%) |
| Missing as non-responder | 35 (77.8%) | 16 (38.1%) |
| P-value Responder vs. non-responder | | 0.0002 |
| P-value Responder vs. non-responder/Missing | | 0.0002 |

TABLE 14-continued

Individual CSS by Treatment Group and Visit - Subjective Diplopia Score Imputation for Subjects Receiving TED During Follow-up (ITT Population)

| | Placebo | RV 001 |
|---|---|---|
| WEEK 28 | | |
| 0, NO DIPLOPIA | 19 (42.2%) | 16 (38.1%) |
| 1, INTERMITTENT | 7 (15.6%) | 6 (14.3%) |
| 2, INCONSTANT | 6 (13.3%) | 10 (23.8%) |
| 3, CONSTANT | 7 (15.6%) | 4 (9.5%) |
| Missing | 6 (13.3%) | 6 (14.3%) |
| CSS responder | 9 (20.0%) | 23 (54.8%) |
| CSS non-responder | 30 (66.7%) | 13 (31.0%) |
| Missing | 6 (13.3%) | 6 (14.3%) |
| Missing as non-responder | 36 (80.0%) | 19 (45.2%) |
| P-value Responder vs. non-responder | | 0.0004 |
| P-value Responder vs. non-responder/Missing | | 0.0008 |
| WEEK 72 | | |
| 0, NO DIPLOPIA | 21 (46.7%) | 20 (47.6%) |
| 1, INTERMITTENT | 7 (15.6%) | 3 (7.1%) |
| 2, INCONSTANT | 5 (11.1%) | 6 (14.3%) |
| 3, CONSTANT | 5 (11.1%) | 7 (16.7%) |
| Missing | 7 (15.6%) | 6 (14.3%) |
| CSS responder | 11 (24.4%) | 20 (47.6%) |
| CSS non-responder | 27 (60.0%) | 16 (38.1%) |
| Missing | 7 (15.6%) | 6 (14.3%) |
| Missing as non-responder | 34 (75.6%) | 22 (52.4%) |
| P-value Responder vs. non-responder | | 0.0204 |
| P-value Responder vs. non-responder/Missing | | 0.0241 |

Note:

Subject diplopia score is defined as 0, no diplopia;

1, intermittent, i.e. diplopia in primary position of gaze, when tired or when first awakening;

2, inconstant, i.e. diplopia at extremes of gaze;

3, constant, i.e. continuous diplopia in primary of reading position.

Subjects who received TED treatment in the follow-up were treated as non-responders from the time of TED treatment forward.

CSS responders are defined as subjects who had a decrease >=1 grade.

The p-values are from Chi square tests without continuity correction.

TABLE 15

ANCOVA Analysis of Change from Baseline in GO-QOL Transformed Total Score at WEEK s 28, 48 and 72 (ITT Population)

| | Placebo (N = 45) | RV 001 (N = 42) |
|---|---|---|
| WEEK 28 | | |
| n | 37 | 37 |
| Mean (SD) | 6.29 (24.080) | 21.58 (22.002) |
| Median | 9.38 | 20.62 |
| Q 1, Q 3 | −9.38, 25.00 | 9.38, 33.33 |
| Min, Max | −62.50, 48.96 | −21.88, 87.50 |
| WEEK 28 (ANCOVA) | | |
| LS Mean (SE) | 5.16 (3.201) | 22.12 (3.372) |
| Difference in LS Mean (SE) | | 16.96 (4.481) |
| 95% CI for Difference | | 8.027, 25.900 |
| P-value | | <0.001 |
| WEEK 48 | | |
| n | 33 | 37 |
| Mean (SD) | 12.82 (23.419) | 18.49 (21.887) |
| Median | 12.5 | 15.62 |
| Q 1, Q 3 | −6.25, 28.12 | 6.25, 30.00 |
| Min, Max | −25.00, 83.33 | −25.00, 87.50 |
| WEEK 48 (ANCOVA) | | |
| LS Mean (SE) | 9.71 (3.267) | 18.49 (3.227) |
| Difference in LS Mean (SE) | | 8.78 (4.412) |

TABLE 15-continued

| ANCOVA Analysis of Change from Baseline in GO-QOL Transformed Total Score at WEEK s 28, 48 and 72 (ITT Population) | | |
|---|---|---|
| | Placebo (N = 45) | RV 001 (N = 42) |
| 95% CI for Difference | | −0.030, 17.586 |
| P-value | | 0.0508 |
| WEEK 72 | | |
| n | 32 | 33 |
| Mean (SD) | 14.69 (20.140) | 12.72 (20.719) |
| Median | 12.5 | 12.5 |
| Q 1, Q 3 | 3.12, 26.56 | 0.00, 24.17 |
| Min, Max | −31.25, 77.08 | −53.12, 50.00 |
| WEEK 72 (ANCOVA) | | |
| LS Mean (SE) | 12.08 (3.429) | 13.82 (3.502) |
| Difference in LS Mean (SE) | | 1.74 (4.761) |
| 95% CI for Difference | | −7.780, 11.262 |
| P-value | | 0.7159 |

Note:
Separate ANCOVA (Analysis of Covariance) models were applied to WEEK 28, WEEK 49, and WEEK 72 data. The ANCOVA included Baseline values and smoke status as covariates.
Subjects who received TED treatment in the follow-up were excluded from the analyses from the time of TED treatment forward.

TABLE 16

| Summary of Graded Proptosis Response at WEEK 28 | | | | |
|---|---|---|---|---|
| | Placebo | | RV 001 | |
| | N | | | |
| | 45 | | 42 | |
| | No. subjects | % | No. subjects | % |
| High Response | 3 | 6.67% | 23 | 54.76% |
| Response | 3 | 6.67% | 8 | 19.05% |
| Low Response | 10 | 22.22% | 4 | 9.52% |
| No Response | 22 | 48.89% | 1 | 2.38% |
| Missing | 7 | 15.56% | 6 | 14.29% |
| Total | 45 | 100.00% | 42 | 100.00% |

Note 1:
high response (proptosis reduction ≥ 3 mm); response (2 mm ≤ proptosis reduction < 3 mm); low response (1 mm ≤ proptosis reduction < 2 mm); no response (proptosis reduction < 1 mm).
Note 2:
Subjects who received additional TED treatment prior to WEEK 28 were considered as no response. This rule would apply to two Placebo subjects. One subject was not a responder (proptosis was increased by 2.5 mm at WEEK 28); one subject (proptosis was reduced by 2 mm at WEEK 28) would be a responder but was considered as no response in the summary table.

Example 2. A Randomized, Double-Masked, Placebo-Controlled, Phase 3 Study of the Safety and Efficacy of Teprotumumab A randomized, double-masked, placebo-controlled, Phase 3 multicenter study was conducted in which the safety and efficacy of teprotumumab given every three weeks for 24 weeks was compared to placebo. The primary outcome was the percentage of patients with ≥2 mm proptosis reduction at Week—24. Other outcomes included overall responder rate, percentage of patients with clinical activity score (CAS) of 0 or 1, percent with improved diplopia score, average change in proptosis and in GO-QOL score from baseline at Week—24.

Participants

Patients were diagnosed with GD, aged 18-80 years with active, moderate-to-severe TED. Ocular symptoms began≤9 months prior to enrollment, clinical activity score (CAS)≥4, frequently associated with at least one of the following: lid retraction≥2 mm, moderate/severe soft tissue involvement, proptosis≥3 mm above normative values for race/gender and/or periodic or constant diplopia in the more proptotic (study) eye. Inclusion allowed mild hypo- or hyperthyroidism at baseline.

Key exclusion criteria: previous orbital irradiation or surgery for TED; recently decreasing visual acuity or visual field defect, color vision defect from optic nerve involvement within the previous 6 months; steroid use (cumulative dose equivalent to ≥1 g of methylprednisolone for the treatment of TED); immunosuppressive use for any indication within 3 months of screening.

Complete inclusion/exclusion criteria are provided below. Eligible patients must have met/provided all of the following inclusion criteria:

Written informed consent.

Patient between the ages of 18 and 80 years, inclusive, at Screening.

Clinical diagnosis of Graves' disease associated with active TED with a CAS≥4 (on the 7-item scale) for the most severely affected eye at Screening and Baseline.

Moderate-to-severe active TED (not sight-threatening but has an appreciable impact on daily life), usually associated with one or more of the following: lid retraction≥2 mm, moderate or severe soft tissue involvement, exophthalmos≥3 mm above normal for race and gender, and/or inconstant or constant diplopia.

Onset of active TED symptoms (as determined by patient records) within 9 months prior to Baseline.

Patients must be euthyroid with the thyroid function under control, or have mild hypo- or hyperthyroidism (defined as free thyroxine [FT4] and free triiodothyronine [FT3] levels<50% above or below the normal limits) at Screening. Every effort should be made to correct mild hypo- or hyperthyroidism promptly and to maintain the euthyroid state for the duration of the clinical trial.

Does not require immediate surgical ophthalmological intervention and is not planning corrective surgery/irradiation during the course of the study.

Alanine aminotransferase (ALT) or aspartate aminotransferase (AST)≤3 times the upper limit of normal (ULN) or serum creatinine<1.5 times the ULN according to age at Screening Diabetic patients must have HbA1c<9.0% with no new diabetic medication [oral or insulin] or more than a 10% change in the dose of a currently prescribed diabetic medication within 60 days prior to Screening).

Women of childbearing potential (including those with an onset of menopause<2 years prior to Screening, non-therapy-induced amenorrhea for <12 months prior to Screening, or not surgically sterile [absence of ovaries and/or uterus]) must have a negative serum pregnancy test at Screening and negative urine pregnancy tests at all protocol-specified timepoints (i.e., prior to each dose and through Week—48 of the Follow-Up Period); patients who are sexually active with a non-vasectomized male partner must agree to use 2 reliable forms of contraception during the trial, one of which is recommended to be hormonal, such as an oral contraceptive. Hormonal contraception must be started at least one full cycle prior to Baseline and continue for 180 days after the last dose of study drug. Highly effective contraceptive methods (with a failure rate less than 1% per year), when used consistently and correctly, includes implants, injectables, combined oral contraceptives, some intrauterine devices (IUDs), sexual abstinence or vasectomized partner.

Male patients must be surgically sterile or, if sexually active with a female partner of childbearing potential, must agree to use a barrier contraceptive method from Screening through 180 days after the last dose of study drug.

Patient is willing and able to comply with the prescribed treatment protocol and evaluations for the duration of the study.

Patients were ineligible for study participation if they met any of the following criteria:

Decreased best corrected visual acuity due to optic neuropathy as defined by a decrease in vision of 2 lines on the Snellen chart, new visual field defect, or color defect secondary to optic nerve involvement within the last 6 months.

Corneal decompensation unresponsive to medical management.

Decrease in CAS of ≥2 points in the study eye between Screening and Baseline.

Decrease in proptosis of ≥2 mm in the study eye between Screening and Baseline.

Previous orbital irradiation or surgery for TED.

Any steroid use (intravenous [IV] or oral) with a cumulative dose equivalent to ≥1 g of methylprednisolone for the treatment of TED. Previous steroid use (IV or oral) with a cumulative dose of <1 g methylprednisolone or equivalent for the treatment of TED and previous use of steroid eye drops is allowed if discontinued at least 4 weeks prior to Screening.

Corticosteroid use for conditions other than TED within 4 weeks prior to Screening (topical steroids for dermatological conditions and inhaled steroids are allowed).

Selenium and biotin must be discontinued 3 weeks prior to Screening and must not be restarted during the clinical trial; however, taking a multivitamin that includes selenium and/or biotin is allowed.

Any previous treatment with rituximab (Rituxan® or MabThera®) or tocilizumab (Actemra® or Roactemra®). Use of any other non-steroid immunosuppressive agent within 3 months prior to Screening.

Use of an investigational agent for any condition within 60 days prior to Screening or anticipated use during the course of the trial.

Identified pre-existing ophthalmic disease that, in the judgment of the Investigator, would preclude study participation or complicate interpretation of study results.

Bleeding diathesis that in the judgment of the Investigator would preclude inclusion in the clinical trial.

Malignant condition in the past 12 months (except successfully treated basal/squamous cell carcinoma of the skin).

Pregnant or lactating women.

Current drug or alcohol abuse, or history of either within the previous 2 years, in the opinion of the Investigator or as reported by the patient.

Biopsy-proven or clinically suspected inflammatory bowel disease (e.g., diarrhea with or without blood or rectal bleeding associated with abdominal pain or cramping/colic, urgency, tenesmus, or incontinence for more than 4 weeks without a confirmed alternative diagnosis OR endoscopic or radiologic evidence of enteritis/colitis without a confirmed alternative diagnosis).

Known hypersensitivity to any of the components of teprotumumab or prior hypersensitivity reactions to monoclonal antibodies.

Any other condition that, in the opinion of the Investigator, would preclude inclusion in the study.

Previous enrollment in this study or participation in a prior teprotumumab clinical trial.

Human immunodeficiency virus (HIV), hepatitis C or hepatitis B infections.

Use of certain medications and therapies was restricted as were specific pre-existing medical conditions, and are shown below in Table 17.

TABLE 17

| Medication/Therapy | Restricted Dose or Time period |
|---|---|
| Orbital irradiation for TED | Any history or planned procedure during entire study duration (Screening through Week 72 of Follow-Up Period). |
| Eye surgery for TED | Any history or planned procedure during entire study duration (Screening through Week 72 of Follow-Up Period). |
| Steroids for treatment of TED | Any history of steroid use (IV or oral) with a cumulative dose equivalent to 21 g of methylprednisolone for the treatment of TED. |
| | Previous steroid use (IV or oral) with a cumulative dose <1 g methylprednisolone or equivalent for the treatment of TED was allowed if the corticosteroid was discontinued at least 4 weeks prior to Screening. |
| | Steroid eye drops were discontinued at least 4 weeks prior to screening. |
| | Steroids (IV or oral) for treatment of TED and steroid eye drops were not allowed during the entire study duration. |
| Steroids for conditions other | Previous steroid use for conditions other than TED was allowed but must have been discontinued at least 4 weeks prior to Screening. |
| than TED | Topical steroids for dermatological conditions and inhaled steroids were allowed during the study. |
| | IV dexamethasone for infusion-associated AEs was allowed |
| Non-steroid eye drops | Vasoconstrictor eye drops were not allowed during the study. |
| | Other non-steroid drops such as saline or methylcellulose were allowed but not on the day of a clinic visit. |
| Selenium or biotin for TED | 3 weeks prior to Screening through study completion. A multivitamin containing selenium and/or biotin was allowed. |
| Rituximab or tocilizumab | Any previous use or anticipated use during the study. |

TABLE 17-continued

| Medication/Therapy | Restricted Dose or Time period |
|---|---|
| Non-steroid immunosuppressive agent (other than rituximab or tocilizumab) | 3 months prior to Screening through study completion. |
| Investigational agent | 60 days prior to Screening through study completion. |
| Illicit drug/alcohol use | History of abuse within the past 2 years or abuse during study. |

Randomization and Masking

Following screening patients were randomized (1:1) to receive 8 infusions of either teprotumumab (10 mg/kg for the first infusion and 20 mg/kg for subsequent infusions) or placebo every 3 weeks over 24 weeks. A follow-up period lasted an additional 48 weeks to Week 72, during which clinic visits occurred. Randomization was generated by an interactive web response system [Bioclinica eClinical Solutions (CRO)]. Patients, investigators, and all study site personnel (excluding formulating pharmacist) were masked to assignment and remained masked through follow-up data analysis and site-close-out visit completion.

Outcomes and Assessments (all from Baseline)

The primary endpoint was proptosis responder rate (percentage of patients with ≥2 mm reduction in the study eye without ≥2 mm increase in the fellow eye) at Week—24 for teprotumumab versus placebo.

Key secondary outcomes were: overall responder rate (defined as the percentage of patients with both ≥2-point reduction in CAS AND ≥2 mm reduction in proptosis, without corresponding increase [≥2-point/≥2 mm] in the fellow eye), percentage of patients with CAS 0 or 1, average change in proptosis, and diplopia improvement through Week—24. QOL was assessed by the average change in the Graves' ophthalmopathy QOL (GO-QOL) questionnaire overall score (Text, Supplementary Appendix). Outcomes were also captured for the fellow eye.

Proptosis was measured in mm using the same Hertel instrument and observer at each study site. Inflammation was quantified using the CAS 7-point scale. Diplopia changes were assessed using the Gorman Score. Patients completed GO-QOL with two sub-scales (visual and appearance).

Safety was monitored, including adverse events (AEs) of special interest.

After 24 weeks, proptosis non-responders could enter an open-label extension study and receive 8 additional infusions of teprotumumab Patients not in the extension were followed for 48 weeks. Responders who relapse during follow-up could enter the extension study.

Statistical Analysis

The sample size was based on the Phase 2 trial of Example 1, where a 51% difference between teprotumumab and placebo was observed at Week—24 for proptosis reduction of ≥2 mm. The sample size of 38 patients per group provided 90% power at the 2-sided alpha 0.05 level to detect a difference of 39% between teprotumumab and placebo adjusted to allow for a 16% discontinuation rate.

All analyses included the intent-to-treat (ITT) population (all patients undergoing randomization). The per protocol (PP) population (those receiving ≥1 infusion with at least one post-baseline value and completed treatment) evaluated the sensitivity of the ITT analysis.

Week—24 efficacy data were included, regardless of premature discontinuation of study drug. Patients missing Week—24 data were considered non-responders. The primary proptosis responder rate assessed the stratified difference (according to tobacco use) in the proportions of responders between the treatment groups. Cochran-Mantel-Haenszel (CMH) weighting estimated the common risk difference within strata and the standard error (SE) of the risk difference.

To reduce Type 1 error rate, all measures were tested in a hierarchical stepwise fashion as outlined in the SAP. For the secondary endpoints of proptosis and GO-QOL (as continuous variables) a mixed-model repeated-measures (MMRM) analysis of covariance (ANCOVA) was used. The scores from each set of 8 questions in GO-QOL were transformed to a scale from 0 to 100 for visual functioning, appearance and overall combined score. Model terms included baseline score, tobacco use, treatment, and visit (including by-treatment/baseline-score interactions).

Results

A total of 107 patients were screened and 83 underwent randomization. (FIG. 1). All assigned patients were included in the efficacy analysis. Ninety-five percent of each group completed the study. Baseline characteristics were similar (Table 18).

TABLE 18

Baseline Characteristics of Patients

| | Teprotumumab (N = 41) | Placebo (N = 42) |
|---|---|---|
| Sex, n (%) | | |
| Male | 12 (29.3) | 11 (26.2) |
| Female | 29 (70.7) | 31 (73.8) |
| Age, years, mean (SD) | 51.6 (12.63) | 48.9 (12.96) |
| 265 years, n (%) | 9 (22.0) | 4 (9.5) |
| <65 years, n (%) | 32 (78.0) | 38 (90.5) |
| Ethnic origin, n (%) | | |
| White | 35 (85.4) | 37 (88.1) |
| Black | 4 (9.8) | 2 (4.8) |
| Asian | 2 (4.9) | 1 (2.4) |
| Other | 0 (0.0) | 2 (4.8) |
| Duration of TED, months, mean (SD) | 6.20 (2.328) | 6.42 (2.377) |
| Time since Diagnosis of Graves' Discase, years, mean (SD) | 3.5 (6.13) | 2.2 (3.19) |
| Smoking status, n (%) | | |
| Smokers | 9 (22.0) | 8 (19.0) |
| Non-smokers | 32 (78.0) | 34 (81.0) |
| Proptosis, mm, mean (SD) | 22.62 (3.322) | 23.20 (3.208) |
| Clinical activity score [CAS, 7 point scale], mean (SD) | 5.1 (0.88) | 5.3 (0.98) |
| Prior intravenous steroid therapy | 0 (0.0) | 0 (0.0) |
| Thyroid hormone level, pmol/L, mean (SD)* | | |
| Free triiodothyronine (FT3) | 5.10 (1.754) | 5.29 (1.718) |
| Free thyroxine (FT4) | 16.46 (5.319) | 16.20 (4.808) |

*Normative range for FT4 was 11.5-22.7 pmol/L and for FT3 was 3.5-6.5 pmol/L

Overall results appear in Table 19.

TABLE 19

Overall results, Phase 3

| Endpoint | Teprotumumab | Placebo | Difference* (95% CD) | P value |
|---|---|---|---|---|
| Primary endpoint | | | | |
| % proptosis responder Week 24 (ITT) | 34/41 (82.9%) | 4/42 (9.5%) | 73.45% (58.89, 88.01%) | <0.001 |
| % proptosis responder Week 24 (PP) | 29/33 (87.9%) | 4/34 (11.8%) | 76.11% (60.58, 91.65%) | <0.001 |
| Secondary endpoints (ITT) | | | | |
| Overall responder Week 24 | 32/41 (78.0%) | 3/42 (7.1%) | 70.82% (55.89, 85.75%) | <0.001 |
| % with CAS 0 or 1 Week 24 | 24/41 (58.5%) | 9/42 (21.4%) | 36.03% (17.39, 54.67%) | <0.001 |
| Change in proptosis from baseline through Week 24 (mm) § | −2.82 + 0.19 | −0.54 ± 0.19 | −2.28 (−2.77, −1.80) | <0.001 |
| Diplopia responder Week 24¥ | 19/28 (67.9%) | 8/28 (28.6%) | 39.29% (15.55, 63.02%) | 0.001 |
| Change in GO-QOL from baseline through Week 24 ‡§ | 13.79 + 2.07 | 4.43 + 2.10 | 9.36 (4.08, 14.64) | <0.001 |

Results from the study showed that teprotumumab administered every 3 weeks was significantly more effective than placebo in every key outcome evaluated in this 24-week assessment of moderate-to-severe, active TED. The effect of teprotumumab was rapid across endpoints, evident at the first post-baseline assessment (Week—6), with continued improvement over the 24-week treatment period. Teprotumumab has a favorable benefit-risk profile, improved patient QOL and represents a suitable first-line, potentially disease-modifying treatment for patients with active TED.

Figure 11:
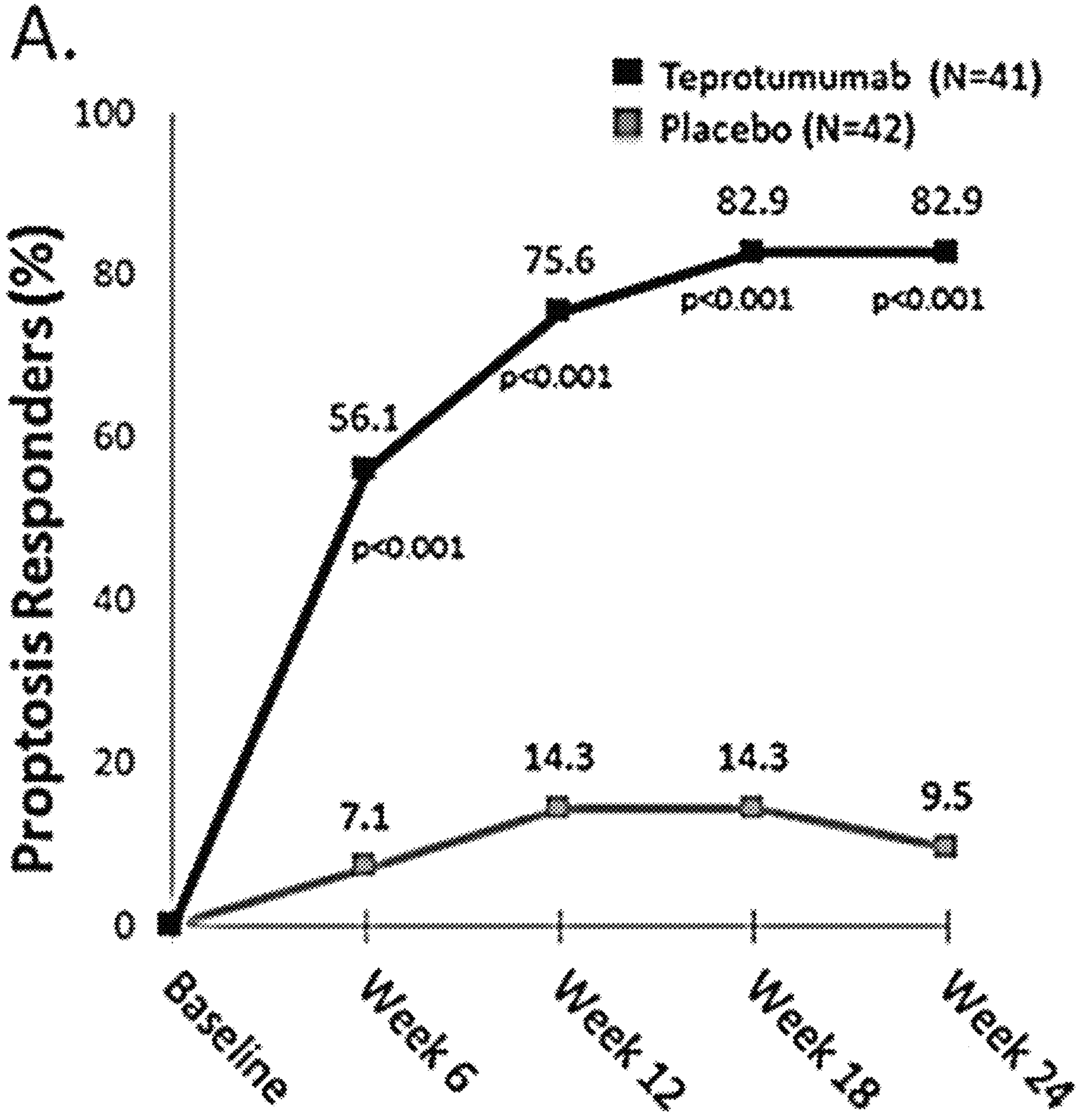
Figure 12:
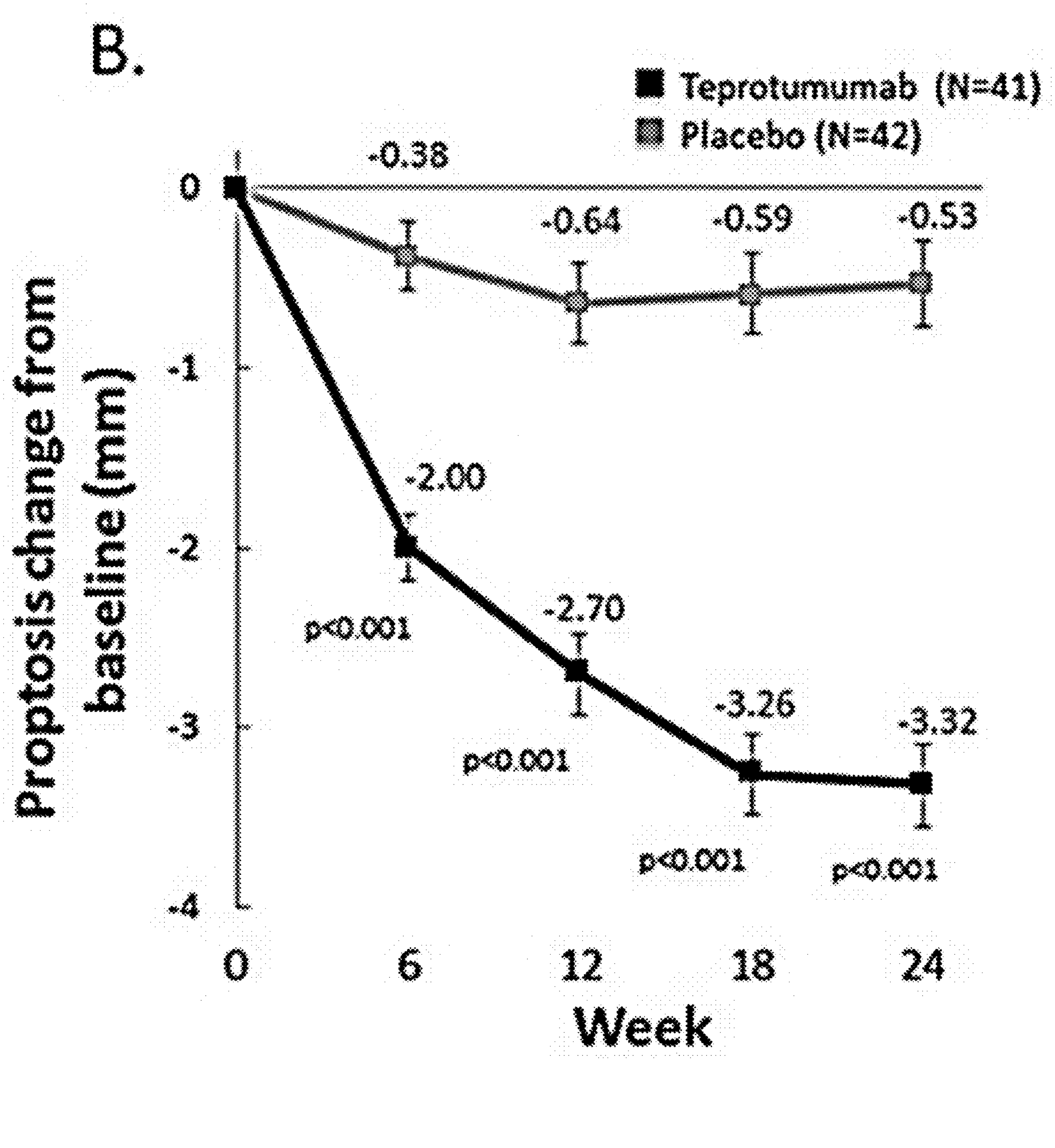

The primary outcome was achieved in 82.9% of patients in the teprotumumab group compared to 9.5% in the placebo group (difference of 73.45%, p<0.001) of the ITT population. The PP cohort results were similar. The response occurred early and improved throughout the trial. (FIG. 11). The initial response for the majority of teprotumumab treated patients occurred at Week—6 (±3 days), with median response of 45 days. Mean change was-3.32 mm at Week—24, comparable to the best results attained with single wall decompression surgery, and was significantly different from placebo at all evaluations (FIG. 12). All patients receiving teprotumumab had some improvement in proptosis at Week—24. Efficacy was demonstrated, regardless of initial proptosis.

Figure 13:
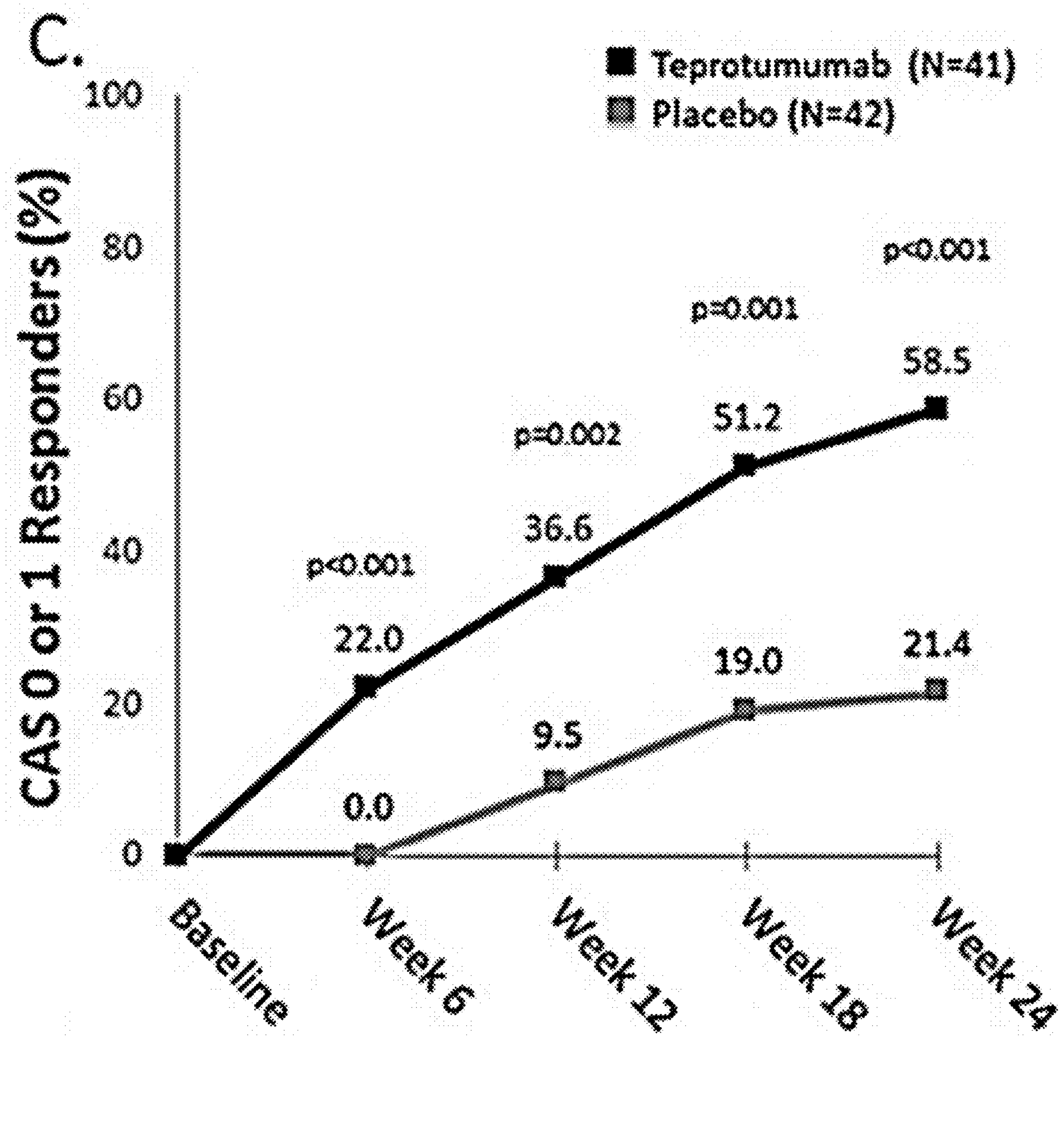
Figure 14:
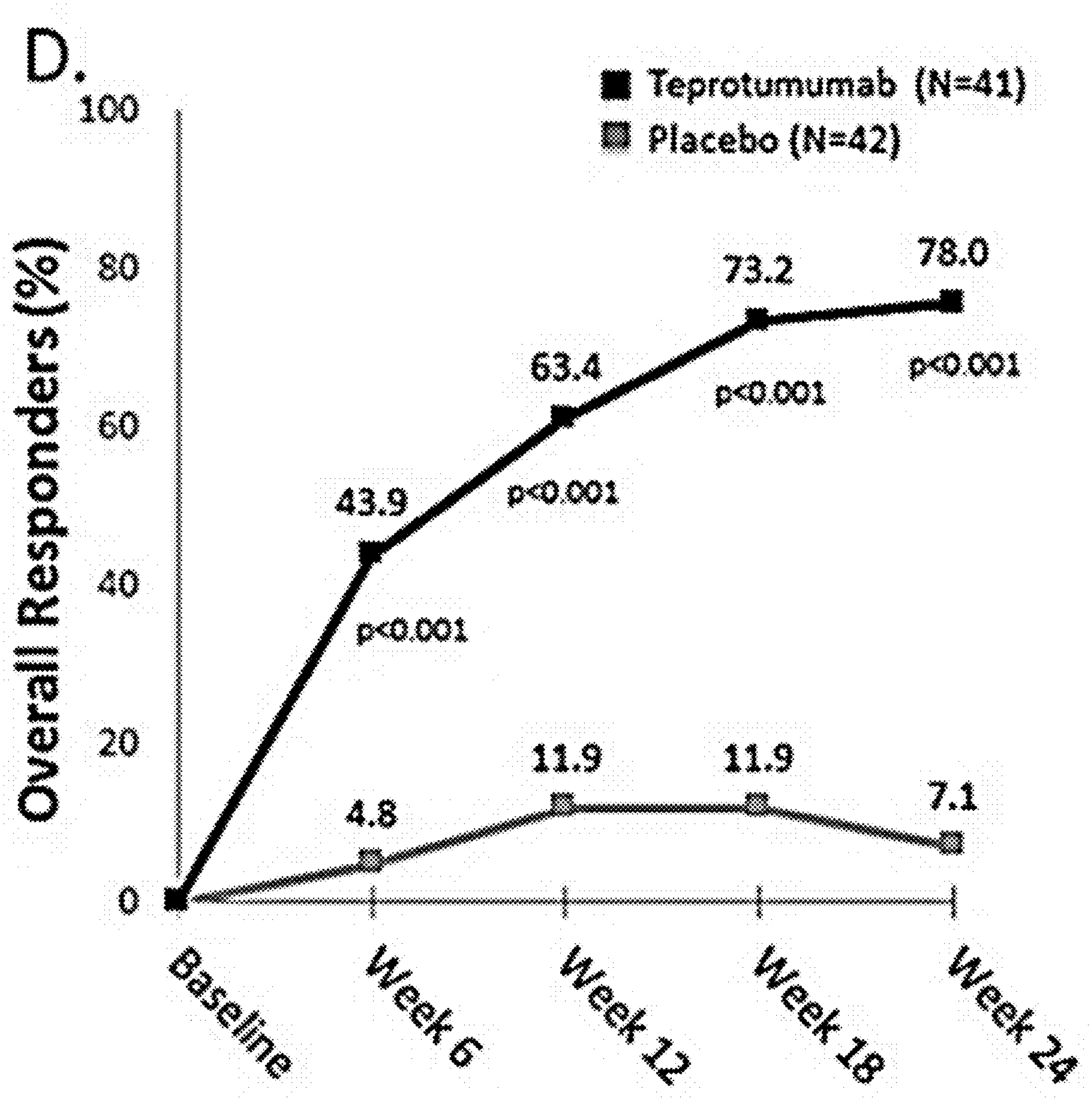

Significantly more patients receiving teprotumumab versus placebo achieved key secondary outcomes. The number of patients with a CAS of 0 or 1 and overall responders increased in the teprotumumab group throughout the treatment period, with significant differences from placebo at all visits (FIGS. 13 and 14).

Figure 15:
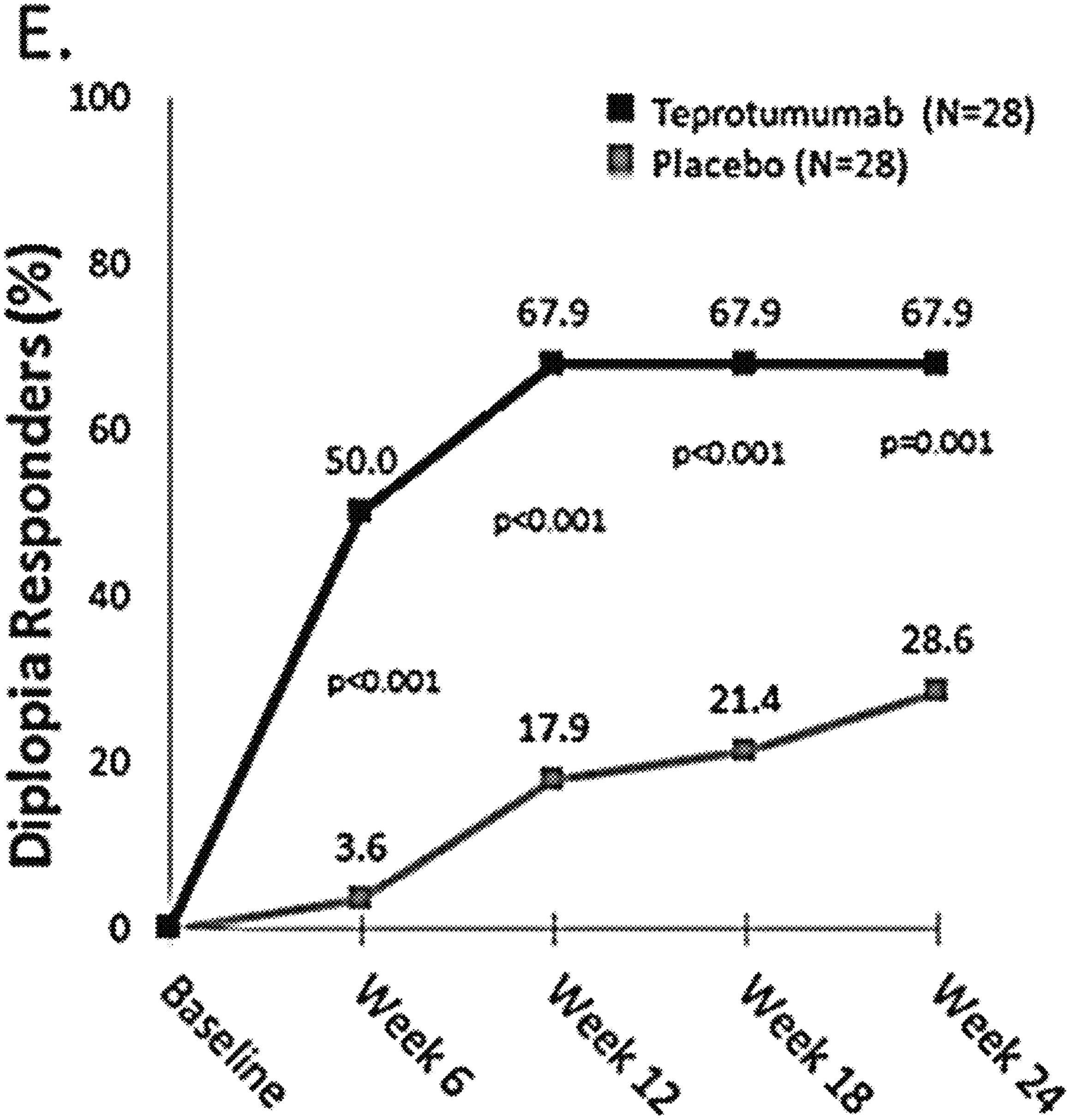
Figure 22:
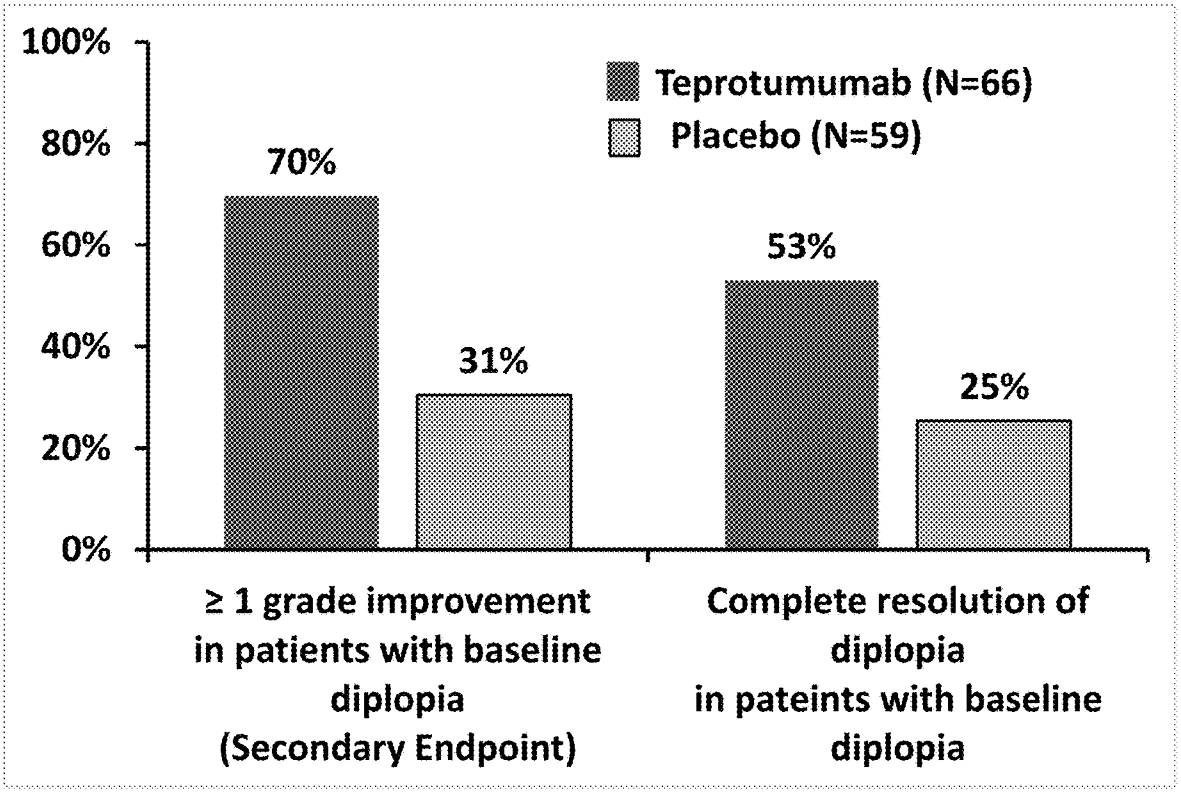

Twenty-eight patients per group experienced diplopia at baseline. Reduction of at least 1 diplopia grade occurred in 50.0% and 3.6% of patients receiving teprotumumab and placebo, respectively at Week—6, with significant differences seen at each time point (FIG. 15); this difference increased to 68% by week 24. Some patients achieved a complete resolution of diplopia. FIG. 22 shows a comparison of achievement of a≥1 grade improvement in 70% of patients and compete resolution of diplopia in 53% of patients with baseline diplopia.

Figure 16:
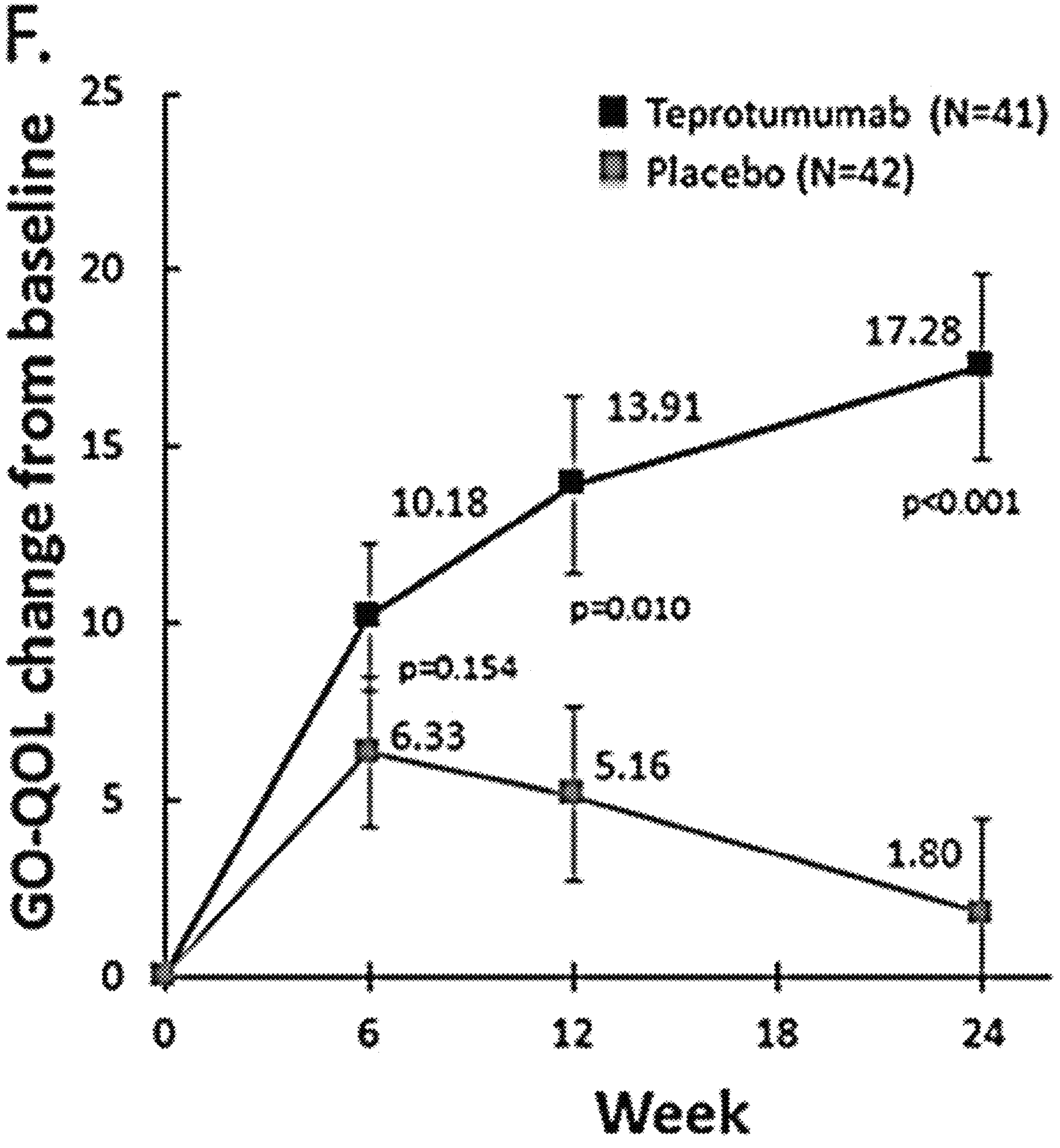
Figure 17:
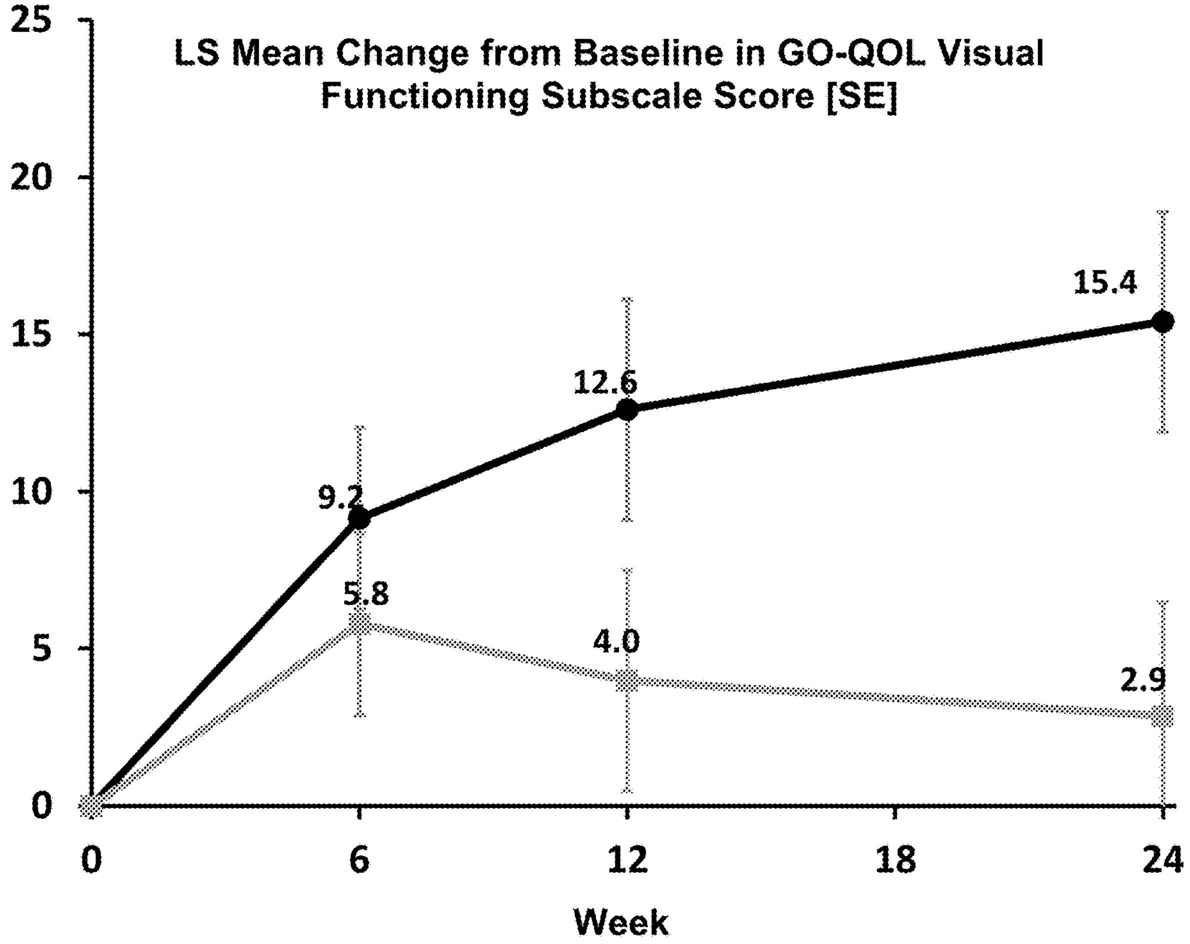
Figure 18:
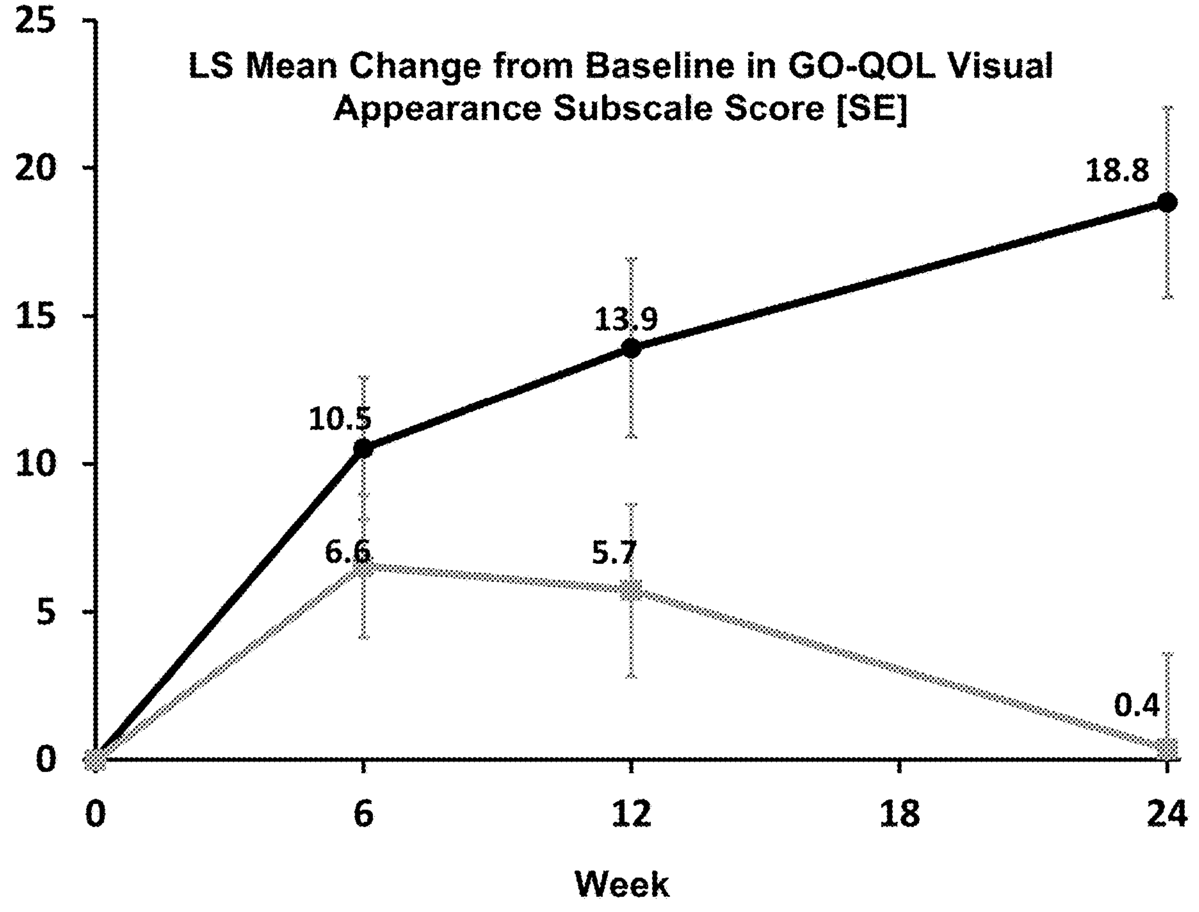

The GO-QOL score improved in patients treated with teprotumumab versus placebo over the study, reaching significance at Week—12 and 24 (FIG. 16). The change in both visual functioning and appearance were >12 with teprotumumab versus about 2 with placebo (FIGS. 17 and 18, respectively). The threshold for clinical importance in non-invasive therapy such as teprotumumab is a change of 6 points.

At one study site, six patients underwent either orbital CT or MRI scans before and after a 24 week treatment with teprotumumab. Extraocular muscle (EOM) and orbital fat volumes were assessed using 3-dimensional analysis. Proptosis reduction was associated with decreased orbital muscle volume and/or orbital fat volume. All patients demonstrated significantly decreased orbital muscle volume (35% mean decrease). Patients with predominant muscle expansion due to TED (4 of 6 patients) demonstrated the largest reduction in volume with relatively little change in fat volume (<10% fat volume change). EOMs can be selectively involved in the disease. The inferior rectus muscle volume exhibited the largest reduction in 4 of 6 patients. Reduction in muscle volume of the most affected muscle was 46% (range 29-62%). Orbital fat volume reduction was observed in two patients. (44%/40%).

Figure 19:
Figure 19:
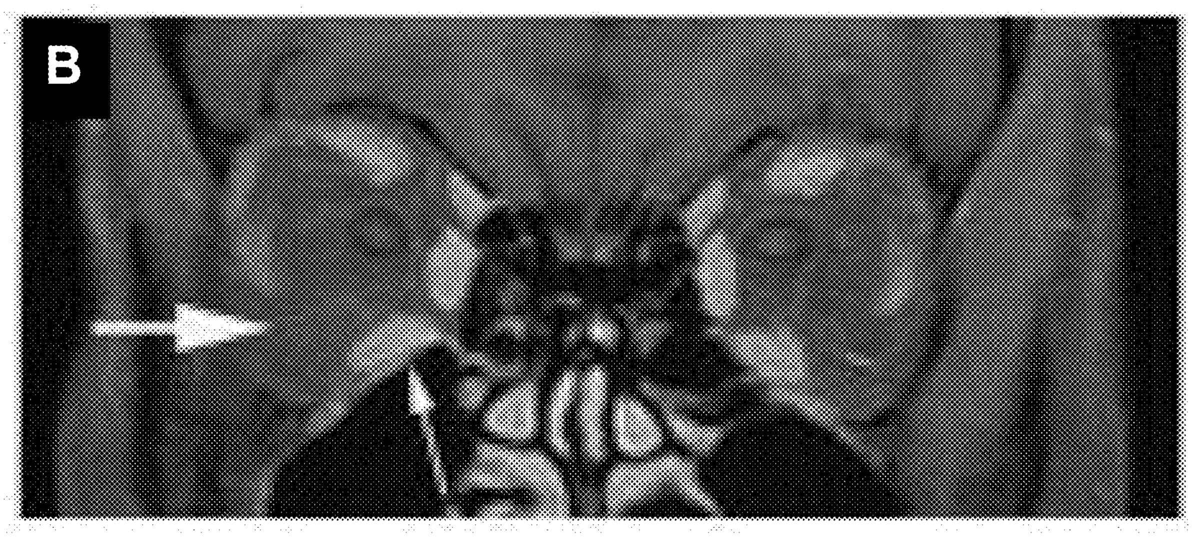

An illustrative example in FIG. 19, which shows Coronal T1 post fat saturation in FIG. 19A, pre-treatment, and FIG. 19B, post-treatment with teprotumumab. Pre-treatment MRI demonstrates marked enhancement of the inferior rectus muscle (thin white arrow) and orbital fat (thick white arrow) indicative of inflammation/edema; in addition, there is enlargement of the inferior rectus muscle (thin white arrow). The patient had 23 mm proptosis, CAS of 5, and Gorman Diplopia Score of 3. F. Post-treatment MRI demonstrates resolution of enhancement of the inferior rectus muscle (thin white arrow) and orbital fat (thick white arrow) indicative of resolved inflammation/edema; there is also a reduction in the size of the inferior rectus muscle by 48.7% by volumetric analysis (thin white arrow), and the medial rectus muscle volume was also reduced by 41%. At this time, the patient had proptosis of 18 mm, CAS of 0, and Gorman Diplopia score of 0.

Figure 20:
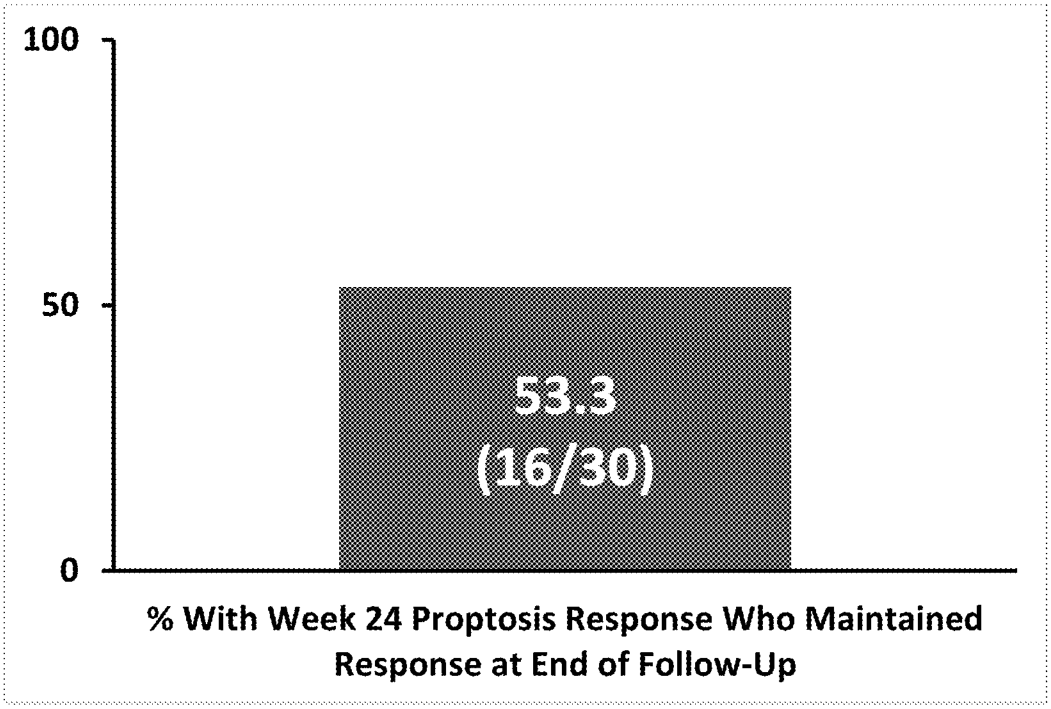
Figure 21:
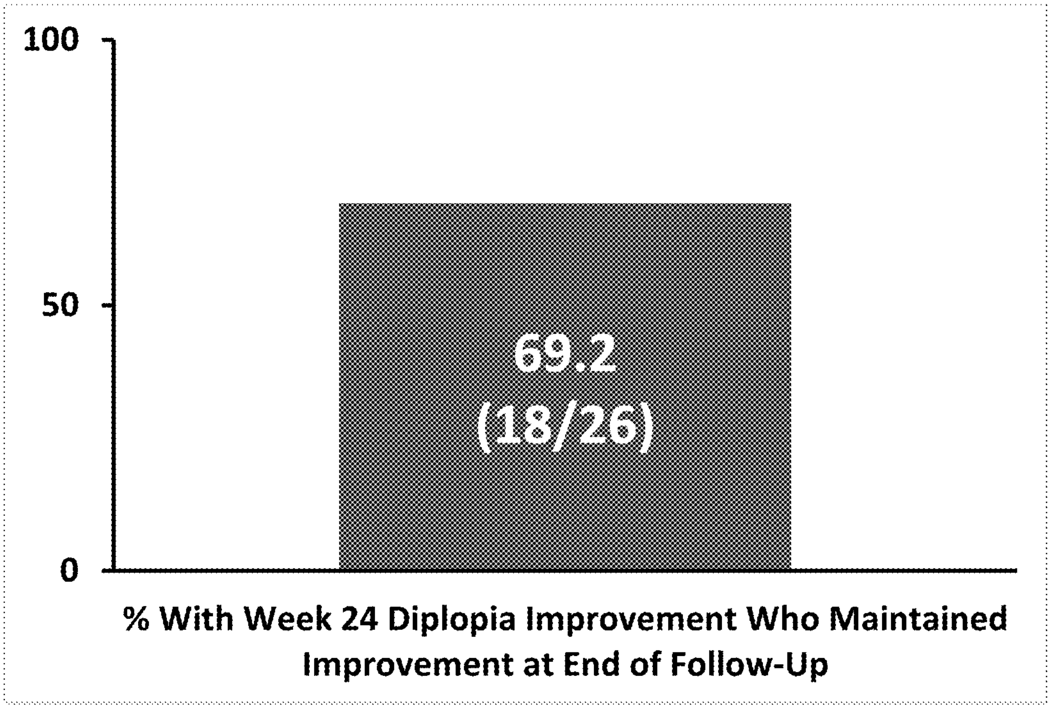
Figure 23:
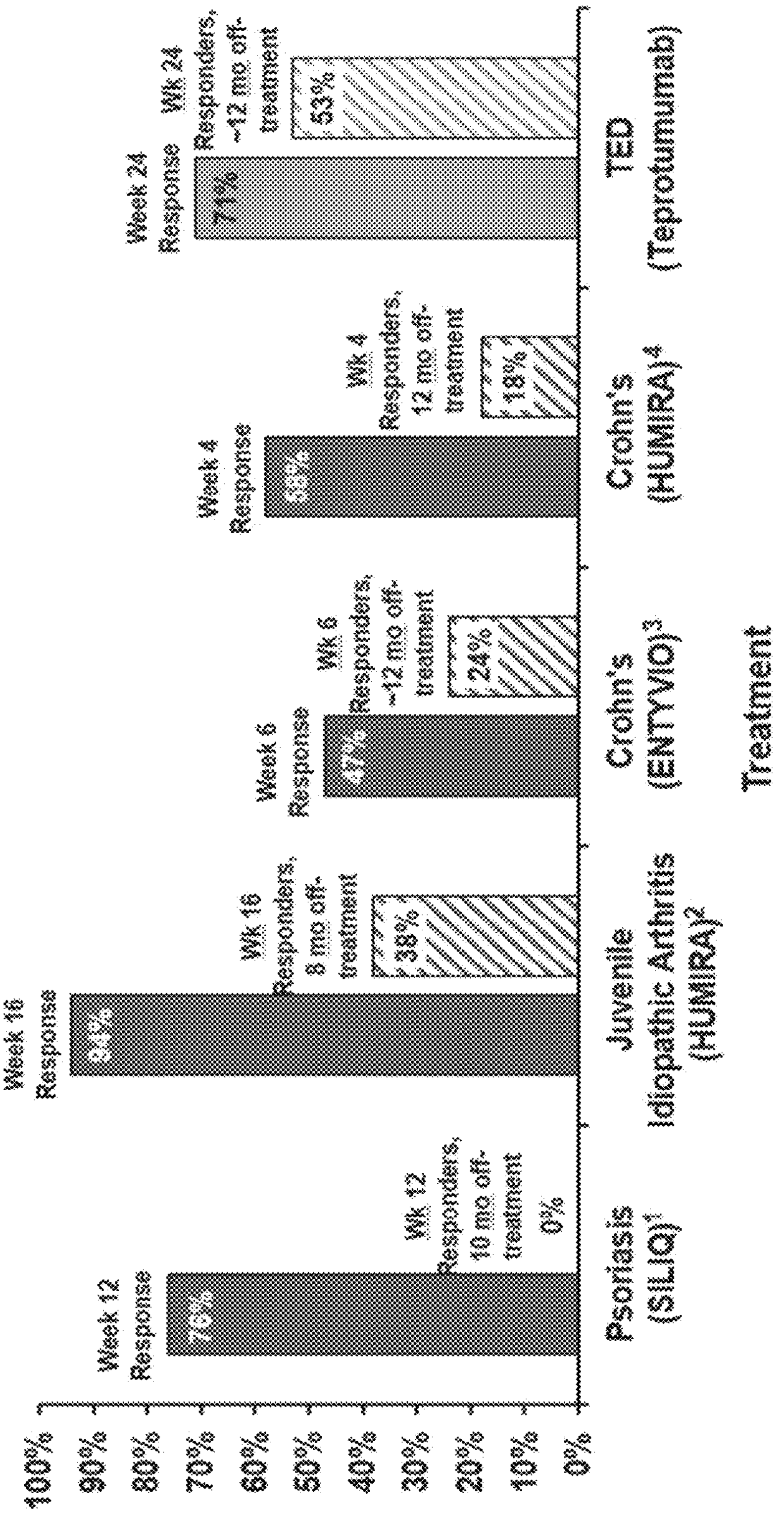

The effects of treatment with teprotumumab were also long-lasting. At week 72, 53% of patients who showed at least a 2 mm improvement from baseline maintained that improvement (FIG. 20), and 73% showed at least somewhat reduced proptosis from their baseline level and did not receive any additional treatment, like steroids or surgery, for their thyroid eye disease. Additionally, 69.2% of patients who were responders in diplopia maintained the improvement (FIG. 21). This duration of response compares favorably with some other biologics clinically tested for the treatment of other diseases (FIG. 23).

Safety.

Adverse Events (AEs) within 21 days of the final dose reported in ≥5% of patients are provided in Table 19.

TABLE 19

| | Teprotumumab (N = 41) Number of patients (%) | Placebo (N = 42) Number of patients (%) |
|---|---|---|
| Adverse Events (AEs) | 35 (85.4) | 29 (69.0) |
| Muscle Spasm | 13 (31.7) | 4 (9.5) |
| Alopecia | 8 (19.5) | 5 (11.9) |
| Nausea | 6 (14.6) | 4 (9.5) |
| Fatigue | 5 (12.2) | 1 (2.4) |
| Diarrhea | 4 (9.8) | 5 (11.9) |
| Headache | 4 (9.8) | 4 (9.5) |
| Dry skin | 4 (9.8) | 0 (0.0) |
| Dysgeusia | 4 (9.8) | 0 (0.0) |
| Stomatitis | 3 (7.3) | 1 (2.4) |
| Amenorrhoea | 3 (7.3) | 0 (0.0) |
| Dizziness | 3 (7.3) | 0 (0.0) |
| Cough | 2 (4.9) | 3 (7.1) |
| Abdominal Pain Upper | 2 (4.9) | 3 (7.1) |
| Influenza | 1 (2.4) | 3 (7.1) |
| Serious Adverse Events (SAEs) | 2 (4.9) | 1 (2.4) |
| Infusion reaction | 1 (2.4) | 0 (0.0) |
| Pneumothorax | 1 (2.4) | 0 (0.0) |
| Visual field defect | 0 (0.0) | 1 (2.4) |

Most treatment-emergent AEs (TEAEs) were mild to moderate. There were 6 and 4 potential infusion reactions of special interest in the teprotumumab and placebo groups, respectively. Two were considered teprotumumab infusion TEAEs during the initial infusion; one patient experienced a non-anaphylaxis reaction and discontinued the trial; the other was pre-medicated during the subsequent infusions with a slower rate and completed the trial.

TEAEs of special interest, based on other monoclonal antibodies and IGF-1R antibody studies, occurring in ≤5% of patients included two (4.9%) patients receiving teprotumumab who developed hyperglycemia (both cases mild). Hearing impairment was reported in 4 patients receiving teprotumumab; two with hypoacusis (resolved), one deafness (resolved), and one tinnitus (occurring with sore throat, and remains unresolved). No auditory issues occurred with placebo. Five patients (4 females) receiving teprotumumab experienced ≥5.0 kg weight loss during the study. Baseline weights for these patients ranged from 59.9 kg to 98.2 kg and overall weight loss ranged from −5.7 kg to −19.0 kg. The 19 kg weight loss was intentional. No TEAEs associated with decreased weight were reported for these patients.

No deaths occurred. Two serious AEs (SAEs) in the teprotumumab group were pneumothorax (unrelated to study drug) and infusion reaction (led to study discontinuation). One placebo patient reported a SAE (visual field defect leading to decompression surgery) and discontinued the study.

No anti-drug antibodies were detected in teprotumumab-treated patients.

At baseline, 8 teprotumumab-treated patients had abnormal slit lamp exams with clinically significant abnormalities consistent with TED, primarily keratitis, and punctate keratopathy/epithelial erosions. At last assessment, 3 had normal slit lamp examinations, 1 had abnormal clinically insignificant findings, and 4 had abnormal, significant findings. Three placebo patients had baseline abnormalities with 1 having abnormal, not significant findings and 2 having abnormal significant findings at last evaluation.

Example 3. Description of Open-Label Clinical Trial to Determine the Efficacy and Safety of Teprotumumab in Relapsers/Nonresponders (Antibody 1)

It is expected that treatment of patients who have previously undergone treatment with an antibody, or an antigen binding fragment thereof, that specifically binds to and/or inhibits insulin like growth factor-I receptor (IGF-1R), e.g., teprotumumab, and either did not respond to said prior treatment or responded to said prior treatment and later relapsed, will respond to treatment with an IGF-1R inhibitor antibody, e.g., teprotumumab. The clinical trial protocol below is one way in which this effect could be demonstrated.

A multi-center, open-label extension study of the study described above as the prior or lead-in trial is being conducted at study centers in the United States and Europe to examine the safety and efficacy of teprotumumab in the treatment of TED in adult subjects. Subjects who completed the 24-week double-masked Treatment Period in the lead-in trial and were proptosis non-responders or were proptosis responders at Week 24 but meet the criteria for re-treatment due to relapse during the follow-up period of the lead-in trial/study are eligible for enrollment. The study treatment previously administered in the lead-in trial/study (teprotumumab or placebo) remained masked throughout this extension study.

All subjects who choose to participate receive up to 8 infusions of teprotumumab (10 mg/kg for the first infusion followed by 20 mg/kg for the remaining 7 infusions) in an open-label fashion, with the number of infusions determined by the investigator's clinical judgment (but not to exceed 8 infusions). The Baseline (Day 1) visit of this extension study occurs within 14 days after the final visit of the lead-in study (Week 24 for proptosis non-responders and up to Week 72 for subjects who relapsed). During the open-label Treatment Period, study drug infusions are scheduled for Day 1 (Baseline), and Weeks 3, 6, 9, 12, 15, 18, and 21 (with a final visit at Week 24 of the 24-Week Treatment Period).

All study drug dosing is performed at the clinic under the supervision of clinic staff, and at any scheduled infusion, the infusion rate may be reduced or the dose may be interrupted or held based on decreased tolerability (as described in examples below). On each dosing day, scheduled assessments (except for adverse event (AE) and concomitant medication use monitoring, which is monitored throughout the clinic visit) are completed prior to study drug dosing. After each of the first 2 infusions, subjects are contacted by phone/email the following day and returned to the clinic 1 week after the infusion (Weeks 1 and 4) for safety and tolerability assessments; additional phone/email contacts and clinic visits are also conducted for any subject experiencing an infusion-associated event.

After completion of the Treatment Period, subjects who are proptosis non-responders in the lead-in trial enter a 24-week Follow-Up Period, during which study drug is not administered and clinic visits are scheduled for 1, 3, and 6 months (Visits Month 7, 9 and 12) after Week 24; subjects discontinued from the Follow-Up Period prior to the Month 12 Visit, return to the clinic and undergo the scheduled Month 12 assessments prior to study discharge. Those who complete the Month 12 Visit will be contacted 6 and 12 months later via phone or email by research staff to enquire if any treatment for TED has been received since last study contact. If yes, subject will be questioned regarding type of treatment and outcome/response. Subjects who relapsed during the follow-up period of the lead-in trial and choose to enter this extension study do not participate in the Follow-Up Period. For these subjects, the last clinic visit is at Week 24. Those who complete the Week 24 Visit will be contacted 6 and 12 months later via phone or email by research staff to enquire if any treatment for TED has been received since last study contact. If yes, subject will be questioned regarding type of treatment and outcome/response.

The study is monitored by a Data Safety Monitoring Board (DSMB), which advises regarding the continuing safety of study subjects and potential subjects as well as continuing validity and scientific merit of the trial.

Study Objectives

The overall objective is to evaluate the safety and efficacy of teprotumumab in the treatment of TED in subjects who participated in the lead-in study and who were either proptosis non-responders at the end of the above mentioned studies or were proptosis responders but met the criteria for re-treatment due to relapse during the Follow-Up Period of the above mentioned study.

The primary objective is to evaluate the effect of teprotumumab on the proptosis responder rate (i.e., the percentage of subjects with a ≥2 mm reduction from baseline in the study eye without deterioration [≥2 mm increase] of proptosis in the fellow eye) at Week 24.

Secondary objectives evaluated the effect of teprotumumab on the following:

(1) Percentage of subjects with a Clinical Activity Score (CAS) value of 0 or 1 at Week 24 in the study eye;

(2) Mean change from baseline to Week 24 in proptosis measurement in the study eye;

(3) Diplopia responder rate (i.e., the percentage of subjects with baseline diplopia>0 in study eye who have a reduction of ≥1 grade with no corresponding deterioration [≥1 grade worsening] in the fellow eye) at Week 24; and (4) Mean change from baseline to the Week 24 in the Graves' Ophthalmopathy Quality of Life (GO-QoL) questionnaire overall score.

Exploratory objectives evaluate the effect of teprotumumab on the following:

(1) The overall responder rate (percentage of subjects with ≥2-point reduction in CAS AND ≥2 mm reduction in proptosis from Baseline, provided there is no corresponding deterioration [≥2-point/mm increase] in CAS or proptosis in the fellow eye) at Week 24.

(2) Clinical Measures of Severity individual response status frequencies and percentage of responders for each component of clinical severity at Week 24.

(3) Mean change from Baseline to Week 24 in the CAS.

(4) Overall responder rate at Week 24 stratified by the level of response (high responders, responders, low responders, and non-responders; see Section 9.6.3.2.1 for definitions).

(5) Mean change from Baseline to Week 24 in the GO-QoL questionnaire visual functioning (VF) and appearance (A) subscale scores.

(6) Mean change from Baseline to Week 24 on the motility component of the Clinical Measures of Severity.

(7) Evaluate pharmacokinetic (PK) parameters of teprotumumab to estimate exposure and understand PK-PD relationships.

Study Design and Plan

Infusions of Teprotumumab (10 mg/kg on Day 1 followed by 20 mg/kg once every 3 weeks (q3W) for the remaining infusions) are provided to the subjects. The number of infusions is individualized for each subject and is based on the investigator's clinical judgment. The Day 1 Visit occurs within 14 days after the final visit of the prior trial. Visit windows are ±1 day for Weeks 1 and 4, ±3 days for Weeks 3, 6, 9, 12, 15, 18, 21, and 24. The Follow-up period is meant for subjects who were proptosis non-responders in the prior trial only; subjects who relapsed in the prior trial did not participate in the Follow-Up Period. Visit windows during the Follow-up period are ±7 days.

Subjects are contacted by phone/email the day following the first and second infusions for safety and tolerability assessments; phone/email contacts also occur the day after any clinic visit where a subject experiences an infusion-related adverse effect (AE). When the investigator determines that dosing is complete, or if the subject wishes to discontinue dosing, the subject returns to the clinic 3 weeks after the last dose and undergoes the scheduled assessments. Subjects who relapsed in the prior study are discharged from the study after completion of the assessments. If a subject participated in the Follow-Up Period and prematurely discontinued prior to Month 12, he/she returns to the clinic and undergoes the assessments prior to study discharge.

Details regarding the study population are provided below. The measurements used in this study for the primary and secondary endpoints (proptosis, CAS, and GO-QOL questionnaire) are established and well-validated endpoints that have been shown to correlate significantly with TED.

This is an open-label extension study. In order to maintain the study mask in the lead-in trial, all subjects in this open-label extension study undergo the same dosing regimen of teprotumumab (10 mg/kg on Day 1 followed by 20 mg/kg q3W for the remaining infusions), regardless if they received teprotumumab or placebo in the prior study.

Given the teratogenic effects of teprotumumab noted in a monkey embryo-fetal development toxicity study in past studies, all subjects (men and women) are required to use adequate contraception and report any pregnancies for at least 6 months after the last dose of study drug. Specifically, female subjects of childbearing potential who are sexually active with a non-vasectomized male partner must agree to use 2 reliable forms of contraception, one of which is recommended to be hormonal, during the trial and for 180 days after the last of study drug. Male subjects who are sexually active with a female partner of childbearing potential must agree to use a barrier contraceptive method from Baseline through 180 days after the last dose of study drug. Six months after the last dose, the estimated plasma concentration (0.2 μg/mL) is considered reasonably safe with a low risk of teratogenicity. Furthermore, a 6-month waiting period is in line with recommendations given for other teratogens, such as cytostatic chemotherapy.

Subject Population

Subjects with TED who had completed the 24-week double-masked Treatment Period in the prior trial above and were proptosis non-responders (<2 mm reduction in proptosis in the study eye) or were proptosis responders at Week 24 in the prior study, but who meet criteria for re-treatment due to relapse during the Follow-Up Period are eligible to enter this open-label extension study. The study population enrolled in the prior trial was well-defined and consistent with the expected target population for whom teprotumumab will be indicated (adult subjects with active moderate-to-severe TED).

The sample size is not based on statistical considerations. Subjects who were proptosis non-responders at Week 24 of the prior trial or who were proptosis responders at Week 24 but meet the criteria for re-treatment due to relapse during the follow-up period of the prior trial are eligible for enrollment.

Subject Inclusion Criteria

Eligible subjects must meet/provide all of the following criteria: (1) written informed consent; (2) completed the 24-week double-masked Treatment Period in the lead-in study; (3) proptosis non-responder (<2 mm reduction in proptosis in the study eye) at Week 24 of the lead-in study or proptosis responder at Week 24 who relapsed during the follow-up period of the prior trial; (4) subject is euthyroid with the baseline disease under control, or has mild hypo- or hyperthyroidism (defined as free thyroxine [FT4] and free triiodothyronine [FT3] levels<50% above or below the normal limits) at the most recent clinic visit (and every effort will be made to correct the mild hypo- or hyperthyroidism promptly and to maintain the euthyroid state for the full duration of this clinical trial); (5) alanine aminotransferase (ALT) or aspartate aminotransferase(AST)≤3 times the upper limit of normal (ULN) or serum creatinine<1.5 times the ULN (according to age) at the most recent clinic visit; (6) diabetic subjects must have well-controlled disease (defined as HgbA1c<9.0% at most recent clinic visit); (7) does not require immediate surgical ophthalmological intervention and is not planning corrective surgery/irradiation during the course of the study; (8) women of childbearing potential must have a negative urine pregnancy test at Baseline/Day 1 and must agree to use 2 reliable forms of contraception during the trial and continue for 180 days after the last dose of study drug (one of the 2 forms of contraception is recommended to be hormonal, such as an oral contraceptive; hormonal contraception is to be in use for at least one full cycle prior to Baseline; highly effective contraceptive methods, when used consistently and correctly, include implants, injectables, combined oral contraceptives, some intrauterine devices (IUDs), sexual abstinence or vasectomized partner; (9) male subjects must be surgically sterile or, if sexually active with a female of childbearing potential, must agree to use a barrier contraceptive method from Baseline through 180 days after the last dose of study drug; (10) subject is willing and able to comply with the prescribed treatment protocol and evaluations for the duration of the study.

Subject Exclusion Criteria

Subjects are ineligible if, in the opinion of the investigator, they are unlikely to comply with the study protocol or have a concomitant disease or condition that could interfere with the conduct of the study or potentially put the subject at unacceptable risk. Exclusion criteria from the lead-in trial (excluding screening criteria) also apply to this open-label extension study.

Removal of Subjects from Therapy or Assessment

All subjects are free to withdraw from study participation at any time, for any reason, and without prejudice to their further medical care. In addition, the investigator may terminate a subject from the study at any time. The primary reason for discontinuation from the study and/or study drug should be recorded, e.g. using one of the following categories:

Adverse Event (AE).

The subject experiences an AE that imposes an unacceptable risk to the subject's health, or the subject is unwilling to continue because of an AE. AEs requiring permanent study drug discontinuation per the protocol include: a drug-related anaphylactic reaction; a persistently severe drug-related AE that does not abate to mild or moderate intensity at least 2 weeks prior to the next scheduled dose; severe drug-related hyperglycemia (e.g., blood glucose>250 mg/dL) that does not abate to mild or moderate intensity with anti-diabetic treatment (dose may be skipped up to 2 times prior to permanently discontinuing study drug; diagnosed or suspected IBD (e.g., diarrhea with or without blood or rectal bleeding associated with abdominal pain or cramping/colic, urgency, tenesmus, or incontinence for more than 4 weeks without a confirmed alternative diagnosis or endoscopic or radiologic evidence of enteritis/colitis without a confirmed alternative diagnosis).

Lack of Efficacy:

The Investigator determines that study drug administration is not benefitting the subject, and continued participation poses an unacceptable risk to the subject.

Non-Compliance with Study Drug/Other/Protocol Deviations.

The subject has a significant protocol deviation, does not comply with study drug administration schedule, or fails to adhere to other study requirements as stated in the protocol.

Lost to Follow-Up.

The subject does not return to the clinic for scheduled assessments, and does not respond to the site's attempts to contact the subject.

Voluntary Withdrawal.

The subject wishes to withdraw from the study. The clinical site should attempt to determine the underlying reason for the voluntary withdrawal and document it; if the underlying reason is documented as an AE or lack of efficacy, the category of withdrawal should be marked in the corresponding category and not as voluntary withdrawal.

Study Terminated by Sponsor.

The sponsor, IRB, or regulatory agency terminates the study.

Pregnancy.

When treatment is complete, the subjects will undergo the scheduled Week 24 assessments.

Subjects who relapsed during the lead-in study were discharged after completion of the Week 24 assessments.

Subjects who were proptosis non-responders in the lead-in study will participate in the Follow-Up Period. Subjects who enter the Follow-Up Period but prematurely discontinue study participation prior to Month 12 will return for a final visit and undergo the scheduled Month 12 assessments prior to study discharge. Subjects who discontinue due to an AE should be followed until resolution or stabilization of the AE, or an adequate explanation for the event is obtained.

No subject prematurely discontinued from the study for any reason is replaced.

Criteria for Responders Who Relapse

If subjects met the response criteria at Week 24 of the prior study but subsequently experience a disease relapse during the 48-week follow-up period of the lead-in/prior study, they will have the option to enter this open-label extension study and receive 8 infusions of teprotumumab. The criteria to determine relapse is the following:

- Increase in proptosis of ≥2 mm in the study eye since Week 24 of the prior study, or
- An increase in CAS of ≥2 points since Week 24 with an absolute CAS of ≥4 in the study eye following Week 24 of the prior study.

In addition to one of the bullet points above, the investigator also considered the subject's symptomology to ensure a relapse had occurred (e.g., new onset of double vision).

Dose Regimen and Route of Administration

All study drug dosing is performed at the clinic under the supervision of clinic staff. Subjects receive 8 infusions of teprotumumab (10 mg/kg on Day 1 followed by 20 mg/kg once every 3 weeks (q3W) for the remaining infusions) in an open-label fashion.

The infusion rate may be reduced and the dose may be interrupted or held based on tolerability (as described below). The first and second IV infusions are administered over approximately 90 minutes (but not less than 80 minutes). Subsequent infusions are administered over an approximately 60-minute period (but not less than 50 minutes) providing there are no significant infusion-associated events.

Dosage Form, Strength Formulation and Storage

Teprotumumab 500 mg is provided in single-dose 20 mL glass vials as a freeze-dried powder containing, in addition to the drug substance, 20 mmol/L histidine-histidine chloride, 250 mmol/L trehalose, and 0.01% polysorbate 20 (w/w). Prior to administration, each vial containing 500 mg teprotumumab freeze-dried powder is reconstituted with 10 mL of water for injection. The resulting solution has an approximate concentration of 50 mg/mL teprotumumab. Reconstituted teprotumumab solution is further diluted in 0.9% (w/v) sodium chloride (NaCl) solution prior to administration (as described in more detail below).

Doses up to 1800 mg are administered in a total infusion volume of 100 mL, and those above 1800 mg are administered in a total infusion volume of 250 mL. To maintain a constant volume in the infusion bags, a volume equal to the volume of teprotumumab to be placed into the infusion bag is first removed from the infusion bag using a sterile syringe and needle. The appropriate volume of reconstituted drug product solution based on the subject's dose and body weight is withdrawn and the teprotumumab reconstituted drug product solution is diluted with normal saline (0.9% NaCl) in the infusion bag.

Recommended storage conditions for the freeze-dried teprotumumab drug product are between 2° C. to 8° C. (36° F. to 46° F.), protected from light. Storage at ambient temperature of the reconstituted teprotumumab solution is limited to 4 hours.

The IV infusion is administered at room temperature (20° C. to 24° C. [68° F. to 75° F.]). The diluted product is used within 4 hours of preparation. However, if not used within 4 hours, and if dilution has taken place under controlled and validated aseptic conditions, the infusion solution can be stored for up to 24 hours at 2° C. to 8° C. (36° F. to 46° F.). An Investigational Pharmacy Manual will be provided to all sites and further describe these processes in detail.

The volume of study drug to be administered is determined by the Electronic Data Capture (EDC) system and is based on the subject's weight. The first dose is 10 mg/kg, and subsequent doses are 20 mg/kg. Weight is measured on Day 1 and Weeks 12 and 24 during the Treatment Period. The dose on Day 1 may be based on the weight determined at the most recent clinic visit, provided the most recent visit was within the prior 3 weeks. The doses on Week 3 through Week 9 is based on the weight determined on Day 1, the weight used in the Week 12 dose calculation can be the weight determined on Day 1 or the weight obtained at Week 12. The weight obtained at Week 12 can be used to adjust the dose beginning at Week 12 or Week 15 through Week 21, as appropriate.

Duration of Treatment and Follow-Up

The duration of the Treatment Period is 24 weeks (6 months), during which 8 infusions of teprotumumab are administered.

Subjects who were proptosis non-responders in the lead-in study are scheduled to participate in a 6-month Follow-Up Period in this extension study; subjects who relapsed in the lead-in study and are retreated in this extension study will not participate in the Follow-Up Period.

Dose Modifications, Interruptions, and Delays

Subjects are monitored for immediate infusion-associated events (e.g., nausea, vomiting, facial flushing, warmth, dyspnea, dizziness, hypertension, hypotension, pruritus) and delayed infusion-associated events (e.g., rash). If immediate infusion-associated events are noted, the infusion rate is slowed or interrupted, symptomatic treatment (e.g., antipyretics, antihistamines, beta-agonists, oxygen, IV fluid) is administered, and vital signs (temperature, blood pressure, pulse, and respiratory rate) are monitored every 5 minutes until stable and then every 15 minutes for 2 additional determinations. The infusion may be restarted upon complete resolution of symptoms; however, study drug dosing is permanently discontinued if the event is an anaphylactic reaction.

If delayed infusion-associated events are noted, subjects may continue dosing at the investigator's discretion; however, if a rash worsens following repeated dosing or other signs of serum sickness (e.g., delayed fever, myalgias, arthralgias) are present, study drug dosing is permanently discontinued.

Following the appearance of either immediate or delayed infusion-associated events, subsequent doses may be pretreated with diphenhydramine (1 to 1.25 mg/kg IV; maximum of 50 mg), ranitidine (50 mg IV), famotidine (0.5 mg/kg IV), dexamethasone (0.4 mg/kg IV; maximum of 20 mg), and/or acetaminophen (500 mg). All subsequent infusions are administered over approximately 90 minutes (but not less than 8-minutes) with vital signs monitored every 15 minutes from the start of the infusion through 60 minutes after infusion completion.

In general, the decision to continue dosing should take into consideration the potential benefit and risk to a subject.

Any severe drug-related AE must revert to mild or moderate in intensity at least 2 weeks prior to the next scheduled dose in order for the dose to be administered; if the AE remains severe in intensity within 2 weeks of the next scheduled dose, the subject will be withdrawn from treatment.

Increase in blood glucose is a known AE observed in previous clinical trials with teprotumumab and other IGF-1R antagonists and is known to respond to treatment. Since a referral for treatment of hyperglycemia may take some time, if the Investigator considered it appropriate to continue the subject in the study, the next scheduled infusion visit may be skipped to allow modified anti-diabetic treatment to show its activity and hyperglycemia to return to mild/moderate level before dosing. The subject is then dosed at the next scheduled visit (i.e., 6 weeks after the previous infusion). Fasting blood glucose levels must return to mild/moderate severity before the next scheduled infusion. The above process of withholding a scheduled infusion is permitted only twice during the study.

Restricted Therapy and Medications

Subjects with a previous orbital irradiation or surgery for TED or who had a planned orbital irradiation or surgery for TED over the course of this study are not eligible for study enrollment. In addition, oral corticosteroids, selenium, biotin, immunosuppressive agents, investigational agents, and illicit drug/alcohol use are restricted as shown in Table 20.

TABLE 20

Restricted Medications and Therapies

| Medication/Therapy | Restricted Dose or Time Period |
|---|---|
| Orbital irradiation for TED | Any history or planned procedure during entire study duration (Screening through Week 48 of Follow-Up Period). |
| Eye surgery for TED | Any history or planned procedure during entire study duration (Screening through Week 48 of Follow-Up Period). |
| IV steroid for TED | Any history or planned use during study (IV dexamethasone may be administered for infusion-associated AEs. |
| Oral steroid for TED | Cumulative dose prior to study should not exceed the equivalent of 1 g of methylprednisolone. Oral steroids for TED are not allowed during the entire study duration. |
| IV/oral steroid for conditions other than TED | 3 months prior to Screening of lead-in study through present extension study completion (topical steroids for dermatological conditions and IV dexamethasone for infusion-associated AEs are allowed). |
| Selenium or biotin for TED | 3 weeks prior to Screening of lead-in study through present extension study completion. A multivitamin (taken maximally once daily) containing selenium and/or biotin is allowed. |
| Rituximab (Rituxan ® or Mab Thera ®) or tocilizumab (Actemra ® or Roactemra ®) | Any previous use or anticipated use during the study. |
| Immunosuppressive agent (other than rituximab or tocilizumab) | 3 months prior to Screening of lead-in study through present extension study completion. |
| Investigational agent | 60 days prior to Screening lead-in study through present extension study completion. |
| Illicit drug/alcohol use | History of abuse within the past 2 years or abuse during study. |

Hearing loss and/or ototoxicity is not considered to be an adverse event causally associated with the use of teprotumumab. However, it may be reasonable to avoid ototoxic medications such as systemic administration of aminoglycoside and platinum-based chemotherapy during the study. The following medications may cause muscle spasm/cramps and should be avoided during the study: donepezil, neostigmine, and vincristine.

All concomitant treatment (for TED and other conditions) in the Treatment Period and the Follow-Up Period should be documented.

Criteria for Evaluation

Efficacy assessments will be performed for both eyes at each assessment time point. The "study eye" (i.e., the more severely affected eye) will remain the same as that identified at the Baseline (Day 1) Visit of the prior study. Both eyes are assessed for efficacy but the study eye will be used to assess the primary outcome measure.

Efficacy is assessed by proptosis (measured as exophthalmos evaluation of the Clinical Measures of Severity using a Hertel instrument for consistency in measurement), CAS (7-item scale), diplopia (measured as part of the Clinical Measures of Severity) and Clinical Measures of Severity (including motility restriction assessments).

Quality of life is assessed using the GO-QOL questionnaire.

Safety is assessed via AE and concomitant medication use monitoring, immunogenicity testing, physical and ophthalmic examinations, vital signs, clinical safety laboratory evaluations (complete blood count, chemistry (including thyroid panel and HbA1C), and urinalysis), pregnancy testing (if applicable), and electrocardiograms (ECG). The study is also monitored by a Data Safety Monitoring Board (DSMB).

Proptosis (Exophthalmos) Assessment

Proptosis assessments is performed using a Hertel exophthalmometer for consistency in measurement, and (except when strictly unavoidable) the same Hertel instrument and same observer is used at each evaluation for the full duration of the study. Additionally, the same intercanthal distance (ICD) is used on each occasion.

Proptosis is measured for each eye on Day 1 and Weeks 6, 12, 18, and 24 (or premature withdrawal [PW]) during the Treatment Period, and at Months 7, 9, and 12 (or PW) during the Follow-Up Period. Measurements are recorded on the Clinical Measures of Severity eCRF under exophthalmos.

Clinical Measures of Severity

Based on the EUGOGO Consensus Statement (Bartalena et al, 2008; Wiersinga et al, 2006; see also Mouritis et al., 1989), the CAS is assessed on Day 1 and Weeks 6, 12, 18, and 24 (or PW) during the Treatment Period, and at Months 7, 9, and 12 (or PW) during the Follow-Up Period (see Table 21). Except when strictly unavoidable, the same observer should conduct each evaluation of severity measure for the full duration of the study.

TABLE 21

| Clinical Measures of Severity | |
|---|---|
| Item and Assessment Scale | Minimum change required for classifying overall response |
| Exophthalmos (measured in mm using the same Hertel exophthalmometer provided by the Sponsor for consistency in measurement and same intercanthal distance for each individual patient) | Decrease ≥ 2 mm |
| Lid aperture (distance between the lid margins in mm with the patient looking in the primary position, sitting relaxed and with distant fixation) | Decrease ≥ 2 mm |
| Swelling of the eyelids (absent, mild, moderate, severe) | Decrease ≥ One grade |
| Redness of the eyelids (absent, present) | Decrease ≥ One grade |
| Redness of the conjunctiva (absent, present) | Decrease ≥ One grade |
| Conjunctival edema (absent, present) | Decrease ≥ One grade |
| Inflammation of the caruncle or plica (absent, present) | Decrease ≥ One grade |
| Subjective diplopia score 0 = no diplopia; 1 = intermittent (diplopia in primary position of gaze, when tired or when first awakening); 2 = inconstant (diplopia at extremes of gaze); 3 = constant (continuous diplopia in primary or reading position) | Decrease ≥ One grade |
| Eye muscle involvement (ductions in degrees) | Increase ≥ 8° in at least one direction of gaze |
| Corneal involvement (absent/punctate keratopathy/ulcer) | Decrease ≥ One grade |
| Optic nerve involvement Best corrected visual acuity Color vision Optic disc Relative afferent pupillary defect (APD) (absent/present) Visual fields if optic nerve compression is suspected. | Change of best corrected visual acuity by ≥2 lines on Snellen chart, or substantial color vision change, or significant change of visual fields, or significant change in optic disc appearance, or (Dis-) appearance of relative afferent pupillary defect |

Each item (spontaneous orbital pain, gaze evoked orbital pain, eyelid swelling that is considered to be due to active (inflammatory phase) TED/GO, eyelid erythema, conjunctival redness that is considered to be due to active (inflammatory phase) TED/GO (ignore "equivocal" redness), chemosis, and inflammation of caruncle or plica) is scored (1=present; 0=absent) and scores for each item are summed for total score.

Motility Restriction—Details for Measurement

Motility is examiner assessed by estimating the degrees of restriction in eye movements. It is assessed at the same time points as the Clinical Measures of Severity described above.

Monocular excursions in horizontal and vertical directions of gaze are recorded using the light reflex (LR) test [Dolman et al, 2012].

The clinician shines a pen light in line with the eye being examined in ambient room light and observes the subject's eye along the light's axis. The subject is asked to look in the 4 cardinal directions and the position of the light reflex is viewed on the surface of the cornea. If the light touches the limbus, the eye is assessed to be turned 45 degrees, if half way between the limbus and pupil edge, the eye is assessed at 30 degrees, and if it is at the pupil edge, it is assessed at 15 degrees. Intermediate ductions are judged by estimating the light position between these points to the nearest 5 degrees.

The monocular ductions of each eye (degrees) are recorded for adduction, abduction, supraduction and infraduction.

Except when strictly unavoidable, the same observer should conduct each duction evaluation for the full duration of the study.

Evaluation of Graves' Ophthalmopathy Quality of Life (GO-QOL)

Quality of life is evaluated with the use of the GO QOL questionnaire. The GO-QOL questionnaire [C. B. Terwee et al, 1998] is completed on Day 1 and Weeks 6, 12, and 24 (or PW) during the Treatment Period, and at Months 7 and 12 (or PW) during the Follow-Up Period.

The GO-QoL is a 16-item self-administered questionnaire divided into two self-assessment subscales; one covering impact of visual function on daily activities, the other assesses the impact of self-perceived appearance. The visual function subscale covers activities such as driving, walking outdoors, reading, watching television. The appearance subscale asks the subject questions such as whether ophthalmopathy has altered the subject's appearance, caused other people to have a negative reaction to the subject, caused social isolation, and caused the subject to try to mask his or her appearance. Each subscale has 8 questions which are answered with: yes—very much so; yes—a little; or no—not at all. Each question is scored 0-2, respectively, and the total raw score is then mathematically transformed to a 0-100 scale, where 0 represents the most negative impact on quality of life, and 100 represents no impact. A change of >8 points on the 0-100 scale has been shown to be clinically meaningful. The combined score takes raw scores from both subscales and again transforms them to a single 0-100 scale.

Adverse Events

According to ICH, an adverse event (AE) is any untoward medical occurrence in a subject or clinical investigation subject administered a pharmaceutical product and which does not necessarily have a causal relationship with this treatment. An AE can therefore be any unfavorable and unintended sign (including an abnormal laboratory finding), symptom, or disease temporally associated with the use of a medicinal (investigational) product, whether or not considered related to the medicinal (investigational) product.

Pre-existing conditions that worsen during a study are reported as AEs. New findings reported from the on-study ophthalmic examinations are not reported as AEs if, according to the investigator, the abnormalities are related to TED and not considered related to the investigational product.

Unchanged, chronic conditions are not considered AEs and are not recorded on the AE pages of the eCRF unless there is a clear exacerbation of a chronic condition.

Disease progression is considered as a worsening of a subject's condition attributable to the disease for which the study drug is being studied (i.e., TED). It may be an increase in the severity of the disease under study and/or increases in the symptoms of the disease. The development of worsening proptosis may be considered as disease progression and not an AE. Events, which are unequivocally due to disease progression, are reported as AEs if they fulfill any of the SAE criteria or are the reason for discontinuation of treatment with the study drug.

Serious and Non-Serious Adverse Event:

A Treatment-emergent adverse event (TEAE), baseline event, or suspected adverse reaction is considered serious if, in the view of either the investigator or sponsor, it results in any of the following outcomes:

- Death. This includes any death that occurs during the conduct of a clinical study, including deaths that appear to be completely unrelated to the study drug (e.g., car accidents).
- Life-threatening adverse experience. An AE or suspected adverse reaction is considered life-threatening if, in the view of either the Investigator or the Sponsor, its occurrence places the subject at immediate risk of death. It does not include an AE or suspected adverse reaction that, had it occurred in a more severe form, might have caused death.
- Persistent or significant disability or incapacity.
- Inpatient hospitalization or prolongation of an existing hospitalization.
- Congenital anomaly or birth defect.
- Other medically important event which, according to appropriate medical judgment, may require medical or surgical intervention to prevent one of the outcomes listed above.

Surgical procedures or other therapeutic interventions themselves are not AEs, but the condition for which the surgery/intervention is required is an AE and is documented accordingly.

Elective surgeries that require hospitalization and treatment received at an emergency room or similar facility are not considered as SAEs unless one of the definitions of an SAE listed above is met.

In addition, hospitalizations for planned procedures are not considered an AE unless they are prolonged hospitalizations, and emergency room visits less than 24 hours in duration are not considered hospitalizations.

A non-serious AE includes any AE that is not described in the previous SAE category.

Unexpected Adverse Event:

An AE or suspected adverse reaction is considered unexpected if it is not listed in the Reference Safety Information section of the IB or is not listed with the specificity or severity that has been observed. Unexpected, as used in this definition, also refers to AEs or suspected adverse reactions that are mentioned in the Reference Safety Information as occurring with a class of drugs or as anticipated from the pharmacological properties of the drug, but are not specifically mentioned as occurring with the particular drug under investigation.

Adverse Events of Special Interest:

Based on previous clinical experience in TED, the following AESIs are identified for this study:

- Infusion reactions (e.g., nausea, vomiting, facial flushing, warmth, dyspnea, dizziness, hypertension, hypotension, pruritus)
- Hyperglycemia
- Muscle spasms
- Diarrhea.

Documentation of Adverse Events:

Adverse events that are ongoing at the completion of the prior study and/or occur prior to dosing on Day 1 of the present study will be considered pre-dose AEs. The TEAE reporting period begins with administration of the first dose of study medication on Day 1 and continues until 3 weeks after the last dose of study drug, and the follow-up AE reporting period begins 3 weeks after the last dose of study drug through completion of the follow-up period (Month 12 or PW). All pre-dose AEs, TEAEs, and AEs during the follow-up period must be recorded in the source documents and in the subject's eCRF.

If the Investigator observes an SAE after study completion that he/she believed was possibly caused by the study medication, the investigator will report this SAE.

Detailed information regarding all SAEs is recorded. Whenever possible, the investigator should group together into a single term the signs and symptoms that constitute a single diagnosis. For example, cough, rhinitis, and sneezing might be grouped together as "upper respiratory infection" if the investigator is confident of the diagnosis.

Intensity of Adverse Events:

Intensity of AEs may be graded on a 5-point scale (mild, moderate, severe, life-threatening, death).

TABLE 22

Intensity of Adverse Events

| Intensity | Definition | Corresponding NCI Grade |
|---|---|---|
| Mild | discomfort noticed but no disruption of normal daily activity | 1 |
| Moderate | discomfort sufficient to reduce or affect daily activity | 2 |
| Severe | inability to work or perform normal daily activity | 3 |
| Life-Threatening | represents an immediate threat to life | 4 |
| Fatal | results in death | 5 |

Relationship of Adverse Event to Study Drug

The relationship of the study drug to each AE is determined by the investigator and the sponsor based on the following definitions:

- No reasonable causal relationship (probably not related):
  - There is no plausible temporal relationship or there is another explanation that unequivocally provides a more plausible explanation for the event.
- Yes, reasonable causal relationship (possibly related):
  - There is evidence in favor of a causal relationship (i.e., there is a plausible time course) and at least one of the following criteria apply:
  - There is a reasonable pharmacological relationship (or known class effect)
  - There is no other more plausible explanation There is a positive de-challenge (without active treatment of the event)

There is a positive re-challenge

There is a distinguishable dose effect

Within the reporting requirement under 21 CFR 312.32 (c)(1)(i), the FDA provides the following examples of types of evidence that would suggest a causal relationship between the drug and the AE.

A single occurrence of an event that is uncommon and known to be strongly associated with drug exposure (e.g., angioedema, hepatic injury, Stevens-Johnson Syndrome).

One or more occurrences of an event that is not commonly associated with drug exposure, but is otherwise uncommon in the population exposed to the drug (e.g., tendon rupture).

An aggregate analysis of specific events observed in a clinical trial (such as known consequences of the underlying disease or condition under investigation or other events that commonly occur in the study population independent of drug therapy) that indicates those events occur more frequently in the drug treatment group than in a concurrent or historical control group.

Follow-Up of Adverse Events

Any ongoing study drug-related AE present at the time of study termination, including a clinically significant laboratory test abnormality, is followed until resolved or until the event stabilizes and the overall clinical outcome has been ascertained.

In the event of unexplained, treatment-emergent, clinically significant abnormal laboratory test results or clinically significant changes in laboratory test results, the tests are repeated immediately and followed until the values return to within the reference range or to Baseline for that subject.

Medication Error and Overdose

An overdose is defined as a known deliberate or accidental administration of investigational drug, to, or by a study subject, at a dose≥5% above that which is assigned to that individual subject according to the study protocol. In the event of drug overdose, the subject is treated with symptomatic and supportive care as required.

Pregnancy Reporting

Urine pregnancy testing is performed for women of childbearing potential (including those with an onset of menopause<2 years prior to Screening of the lead-in study, non-therapy-induced amenorrhea for <12 months prior to Screening of the lead-in study, or not surgically sterile [absence of ovaries and/or uterus]) at all clinic visits. Urinary pregnancy tests are performed locally.

If a female subject becomes pregnant during the Treatment Period, she should immediately notify the investigator, and teprotumumab dosing should be permanently discontinued. Pregnancy occurring in the partner of a male subject participating in the study should be reported to the investigator and the sponsor. Monitoring of the partner should continue until conclusion of the pregnancy.

Pregnancies occurring up to 180 days after the last dose should also be reported to the Investigator. The investigator should counsel the subject and discuss the possible risks of continuing the pregnancy. If pregnancy continues, monitoring should also be continued to the conclusion of the pregnancy.

Subjects should be instructed to continue contraception for 180 days after their last dose of study drug.

Vital Signs

Vital signs (heart rate, blood pressure, respiratory rate, temperature) are measured at all clinic visits. Vital signs are measured pre- and post-infusion on Day 1 and Week 3, and predose on any other infusion day. In addition, if immediate infusion-associated events are noted during the infusion, vital signs are monitored every 5 minutes until stable and then every 15 minutes for 2 additional determinations. Also, vital signs are monitored every 15 minutes from the start of the infusion through 60 minutes after infusion completion for any subsequent infusions after the previous occurrence of immediate or delayed infusion-associated events.

Blood pressure and pulse measurements are obtained with the subject's arm unconstrained by clothing or other material and while the subject is sitting up. When possible, the same arm is used for measurements in all study visits. Temperature is obtained orally or via the ear.

Physical and Ophthalmic Examinations, Height, and Weight

A physical examination, including complete undilated ophthalmic examination, is performed at Baseline (Day 1) and thereafter at Weeks 1, 6, 12, 18, and 24 (or PW) during the Treatment Period and Month 12 (or PW) of the follow-up period.

The ophthalmic exam includes best-corrected visual acuity, pupil exam, color vision assessment, Ishihara color plates (or equivalent) or related red desaturation, intraocular pressure and slit lamp exam. If significant abnormalities are noted compared with previous visits, including a loss of 2 lines or more of vision, development of pupil abnormalities including afferent pupillary defect (APD), rise in intraocular pressure, development of corneal infiltrates or other abnormalities not here specified but of concern to the ophthalmologist, further investigations of visual function are conducted according to the ophthalmologist decision.

New findings reported from on-study ophthalmic examinations are not reported as AEs if, according to the investigator, the abnormalities are related to TED and not related to the study drug.

Physical exam includes assessment of presence or absence of pretibial myxedema on Day 1 and Week 24 of the Treatment Period and Month 12/EOS of the follow-up period. If present, measurements of instep and calf are taken.

Weight is measured at Baseline and every 12 weeks throughout the study (Weeks 12 and 24 (or PW) during the Treatment Period and Months 9 and 12 [or PW] of the Follow-Up Period). The dose on Day 1 may be based on the weight determined at the most recent clinic visit, provided the most recent visit was within the prior 3 weeks. The doses on Week 3 through Week 9 are based on the weight determined on Day 1. The weight used in the Week 12 dose calculation can be the weight determined on Day 1 or the weight obtained at Week 12. The weight obtained at Week 12 can be used to adjust the dose beginning at Week 12 or Week 15 through Week 21, as appropriate.

ECGs 12-lead ECGs are performed at Baseline, Weeks 3, 6, 12, and 24 (or PW) of the Treatment Period, and Month 12 (or PW) of the Follow-Up Period. At infusion visits, the ECG is performed prior to the infusion. The results are recorded as normal or abnormal on the eCRF and all abnormal results will be evaluated as clinically (CS) or not clinically significant (NCS) by the Investigator. A copy of the ECG tracing remains with the source documents.

Immunogenicity Testing

Blood samples are collected in a 5 mL SST collection tube for immunogenicity testing (ADA and possibly Neutralizing Antibodies [NAb]) from all subjects prior to dosing on Day 1, prior to dosing on Weeks 3 and 9, and at Week 24 (or PW) of the Treatment Period, and Months 9 and 12 (or PW) of the Follow-Up Period. Samples are collected, processed, and stored at ≥−70° C. at the site until shipment to the central laboratory (Eurofins Global Central Laboratory). Samples are stored at ≥−70° C. until (transport for) immunogenicity testing. If a subject tests positive for ADA after confirmatory and reactive titer testing, the sample is then tested for NAb. If the subject tests positive for NAb, he/she is followed until levels either revert to Baseline or the subject's value decreases or remains stable. Any subject with a positive NAb test at Month 12 (or EOS) of the follow-up period continues to be followed until the subject's value decreases or remains stable.

Study Procedures

Subjects who provide informed consent and who meet all the entry criteria for participation in this study may be enrolled in the open-label extension study.

Day 1/Baseline: The Baseline (Day 1) Visit must occur within 14 days of the final visit of lead-in trial. If Day 1 of the extension study occurs on the same day as the final visit of the lead-in study and an assessment is scheduled for both visits, assessments do not need to be repeated, and the final assessments from the lead-in study will serve as the Baseline assessments for the extension study.

Potential study subjects will be informed fully regarding the nature of the study and possible AEs, and will receive a copy of the informed consent form (ICF) for review. Potential study subjects must read the ICF and sign the document after the investigator has answered all questions to the study candidate's satisfaction. Further procedures begin only after the ICF has been signed. The original signed ICF is retained by the Investigator and a copy will be given to the study subject.

Study candidates are evaluated for study entry according to the stated inclusion and exclusion criteria. The investigator evaluates the results of all examinations, including clinical laboratory tests, from the most recent clinic visit and will determine each candidate's suitability for the study. The investigator reviews these results before determining that a candidate is eligible for study drug treatment. The Baseline urine pregnancy test performed for all female candidates of childbearing potential must be negative in order for subjects to be eligible for treatment. The following procedures are performed at Baseline to establish each candidate's general health and eligibility for enrollment into the study:

- Obtain signed, written informed consent and permission to use Protected Health Information (in accordance with the Health Insurance Portability and Accountability Act [HIPAA]) Refusal to provide this permission excludes an individual from eligibility for study participation. Record date informed consent is given and who conducted the process on the appropriate source documentation.
- Determine study eligibility through review of the inclusion/exclusion criteria.
- Obtain predose blood samples for hematology and chemistry (including thyroid, glucose, and HbA1C) analysis.
- Collect predose blood samples for immunogenicity and PK testing.
- Collect predose urine sample for urinalysis and also for a pregnancy test for females of childbearing potential; the pregnancy test must be negative for the subject to receive study drug.
- Enquire about signs and symptoms within previous 2 weeks.
- Enquire about prior medication use during the previous 2 weeks.
- Perform predose physical and ophthalmic examinations.
- Measure weight.
- Perform predose 12-lead ECG.
- Perform predose Baseline efficacy assessments (proptosis, CAS, diplopia, Clinical Measures of Severity including motility restriction).
- Administer the predose GO-QoL questionnaire.
- Register enrollment in EDC, obtain study medication vial assignment, and to determine the volume of study drug to be administered.
- Monitor vital signs prior to and at the end of the infusion. Additional vital sign monitoring may be performed in the event of infusion-associated AEs.
- Administer the first dose of study drug and record date, volume and rate of infusion, and start/stop times of dosing.
- Monitor subjects regarding treatment-emergent signs and symptoms.
- Collect blood samples for PK analyses at the end of the infusion.

Subjects are discharged from the study center after all of the Study Day 1 procedures had been completed and are contacted the following day to enquire about AEs and concomitant medication use.

Week 1:

- Collect blood samples for hematology and glucose testing.
- Perform physical and ophthalmic examinations, including vital signs.
- Enquire about AEs and concomitant medication use.
- Collect blood sample for PK analyses. Record date/time of sample collection.

Subjects are released from the study center after all of the visit procedures have been completed and are instructed to return to the clinic at Week 3.

Week 3:

- Obtain predose blood samples for hematology and chemistry (including thyroid, glucose, but not HbA1C) analysis.
- Collect predose urine sample for urinalysis and also for a pregnancy test for females of childbearing potential; the pregnancy test must be negative for the subject to receive study drug.
- Collect predose blood sample for immunogenicity and PK testing.
- Enquire about signs and symptoms and concomitant medications throughout the visit.
- Perform predose 12-lead ECG.
- Contact IWRS to obtain study medication vial assignment and to determine volume of study drug to be administered.
- Monitor vital signs prior to and at the end of the infusion. Additional vital sign monitoring may be performed in the event of infusion-associated AEs.
- Administer study drug and record date, volume and rate of infusion, and start/stop times of dosing.
- Collect blood samples for PK analyses at the end of the infusion.

Subjects are discharged from the study center after all of the procedures are completed and are contacted the following day to enquire about AEs and concomitant medication use. Subjects are instructed to return to the clinic at Week 4.

Week 4:

- Collect blood samples for hematology and glucose testing.
- Collect vital signs.
- Enquire about AEs and concomitant medication use.
- Collect blood sample for PK analyses. Record date/time of sample collection.

Subjects are released from the study center after all of the visit procedures are completed and are instructed to return to the clinic at Week 6.

Week 6:

- Obtain predose blood samples for hematology and chemistry (including thyroid, glucose, but not HbA1C) analysis.
- Collect predose urine sample for urinalysis and also for a pregnancy test for females of childbearing potential; the pregnancy test must be negative for the subject to receive study drug.
- Enquire about signs and symptoms and concomitant medications throughout the visit.
- Perform predose 12-lead ECG.
- Perform predose physical and ophthalmic examinations, including vital signs. Additional vital sign monitoring may be performed in the event of infusion-associated AEs.
- Perform predose efficacy assessments (CAS, Clinical Measures of Severity including proptosis, diplopia and motility restriction).
- Administer predose GO-QoL questionnaire.
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return for a clinic visit at Week 9.

Week 9:

- Obtain predose blood samples for hematology and chemistry (including thyroid, glucose, but not HbA1C) analysis.
- Collect predose urine sample for urinalysis and also for a pregnancy test for females of childbearing potential; the pregnancy test must be negative for the subject to receive study drug.
- Collect predose blood samples for immunogenicity and PK testing.
- Enquire about signs and symptoms and concomitant medications throughout the visit.
- Collect predose vital signs. Additional vital sign monitoring may be performed in the event of infusion-associated AEs.
- Obtain study medication vial assignment and volume of study drug to be administered from EDC.
- Administer study drug and record date, volume and rate of infusion, and start/stop times of dosing.
- Collect blood samples for PK analyses at the end of the infusion.

Subjects are discharged from the study center after all of the procedures have been completed and are instructed to return for a clinic visit at Week 12.

Week 12:

- Obtain predose blood samples for hematology and chemistry (including thyroid, glucose, and HbA1C) analysis.
- Collect predose urine sample for urinalysis and also for a pregnancy test for females of childbearing potential; the pregnancy test must be negative for the subject to receive study drug.
- Enquire about signs and symptoms and concomitant medications throughout the visit.
- Perform predose 12-lead ECG.
- Perform predose physical and ophthalmic examinations, including vital signs. Additional vital sign monitoring may be performed in the event of infusion-associated AEs.
- Measure weight.
- Perform predose efficacy assessments (CAS, Clinical Measures of Severity including proptosis, diplopia and motility restriction).
- Administer predose GO-QoL questionnaire.
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return to the clinic at Week 15.

Week 15:

- Obtain predose blood samples for hematology and glucose analysis.
- Perform predose urine pregnancy test for females of childbearing potential; the pregnancy test must be negative for the subject to receive study drug.
- Enquire about signs and symptoms and concomitant medications throughout the visit.
- Collect predose vital signs. Additional vital sign monitoring may be performed in the event of infusion-associated AEs.
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return to the clinic at Week 18.

Week 18:

- Obtain predose blood samples for hematology and chemistry (including thyroid, glucose, but not HbA1C) analysis.
- Collect predose urine sample for urinalysis and also for a pregnancy test for females of childbearing potential; the pregnancy test must be negative for the subject to receive study drug.
- Enquire about signs and symptoms and concomitant medications throughout the visit.
- Perform predose physical and ophthalmic examinations, including vital signs. Additional vital sign monitoring may be performed in the event of infusion-associated AEs.
- Perform predose efficacy assessments (CAS, Clinical Measures of Severity including proptosis, diplopia, and motility restriction).
- Obtain study medication vial assignment and volume of study drug to be administered from EDC.
- Administer study drug and record date, volume and rate of infusion, and start/stop times of dosing.

Subjects are discharged from the study center after all of the procedures are completed and are instructed to return to the clinic at Week 21.

Week 21:

- Obtain predose blood samples for hematology and glucose analysis.
- Collect predose urine sample for a pregnancy test for females of childbearing potential. The pregnancy test must be negative for those subjects to receive study drug.
- Enquire about signs and symptoms and concomitant medications throughout the visit.
- Collect predose vital signs. Additional vital sign monitoring may be performed in the event of infusion-associated AEs.

Obtain study medication vial assignment and volume of study drug to be administered from EDC.

Administer study drug and record date, volume and rate of infusion, and start/stop times of dosing.

Subjects are discharged from the study center after all of the procedures are completed and are instructed to return to the clinic at Week 24.

Week 24/Premature Withdrawal: the final visit of the Treatment Period. Study drug is not administered.

Obtain blood samples for hematology and chemistry (including thyroid, glucose, and HbA1C) analysis.

Collect urine sample for urinalysis and also for a pregnancy test for females of childbearing potential.

Collect blood sample for immunogenicity testing (only subjects who complete the Treatment Period, not those who prematurely discontinue study drug administration).

Enquire about signs and symptoms and concomitant medications throughout the visit.

Perform 12-lead ECG.

Perform physical and ophthalmic examinations, including vital signs.

Measure weight.

Perform efficacy assessments (CAS, Clinical Measures of Severity including proptosis, diplopia, and motility restriction).

Administer GO-QoL questionnaire.

Collect blood sample for PK analyses (only subjects who complete the Treatment Period, not those who prematurely discontinue study drug administration).

Subjects who relapsed during the Follow-Up Period of the lead-in study and chose to enter this extension study are discharged from the study following completion of the assessments (they will not participate in the Follow-Up Period). Subjects who were proptosis non-responders in Study the lead-in study will enter the Follow-Up Period and were instructed to return to the clinic in one month for the first follow-up visit.

Month 7-Follow-Up Period:

Collect urine sample for a pregnancy test for females of childbearing potential.

Enquire about signs and symptoms and concomitant medications throughout the visit.

Collect vital signs.

Perform efficacy assessments (CAS, Clinical Measures of Severity including proptosis, diplopia, and motility restriction).

Administer GO-QoL questionnaire.

Subjects are discharged from the study center after all of the procedures are completed and are instructed to return to the clinic for the Month 9 Follow-Up Visit.

Month 9-Follow-Up Period:

Obtain blood samples for hematology and chemistry (including thyroid, glucose, and HbA1C) analysis.

Collect urine sample for urinalysis and also for a pregnancy test for females of childbearing potential.

Enquire about signs and symptoms and concomitant medications throughout the visit.

Collect blood sample for immunogenicity testing.

Collect vital signs.

Perform efficacy assessments (CAS, Clinical Measures of Severity including proptosis, diplopia, and motility restriction).

Measure weight.

Subjects are discharged from the study center after all of the procedures are completed and are instructed to return to the clinic at Month 12.

Month 12/Premature Withdrawal-Follow-Up Period

For Proptosis Non-Responders in Lead-In Study:

Obtain blood samples for hematology and chemistry (including thyroid, glucose, and HbA1C) analysis.

Collect urine sample for urinalysis.

Collect urine sample for a pregnancy test for females of childbearing potential if the subject discontinued from the study prior to Month 9 of the Follow-Up Period.

Collect blood sample for immunogenicity testing.

Enquire about signs and symptoms and concomitant medications throughout the visit.

Perform 12-lead ECG.

Perform physical and ophthalmic examinations, including vital signs.

Measure weight.

Perform efficacy assessments (CAS, Clinical Measures of Severity including proptosis, and motility restriction).

Administer GO-QoL questionnaire.

For Proptosis Subjects Who Relapsed in Lead-In Study: subjects who complete the Week 24 Visit will be contacted 6 months later via phone or email by research staff to enquire if any treatment for TED has been received since last study contact. If yes, subject will be questioned regarding type of treatment and outcome/response.

Month 18-Follow-Up Period:

For Proptosis Non-responders in Lead-In Study: Subjects who complete the Month 12 Visit will be contacted 6 months later via phone or email by research staff to enquire if any treatment for TED has been received since last study contact. If yes, subject will be questioned regarding type of treatment and outcome/response.

For Subjects Who Relapsed in the Lead-In Study: Subjects who complete the Week 24 Visit will be contacted 12 months later via phone or email by research staff to enquire if any treatment for TED has been received since last study contact. If yes, subject will be questioned regarding type of treatment and outcome/response. This is the final contact for subjects who relapsed in the Lead-In Study.

Month 24—Follow-Up Period: For Proptosis Non-responders in Lead-In Study

Subjects who complete the Month 12 Visit will be contacted 12 months later via phone or email by research staff to enquire if any treatment for TED has been received since last study contact. If yes, subject will be questioned regarding type of treatment and outcome/response. This is the final contact for proptosis non-responders the Lead-In Study. The end of the trial is defined as the date of the last subject contact at Month 24.

Statistical Analyses

The primary analyses are conducted on the Intent-to-Treat (ITT) population. All efficacy and safety endpoints are summarized using descriptive statistics, and summaries are stratified by the treatment received in the lead-in trial as well as overall. Study endpoints are evaluated for all subjects from Baseline to the Week 24 Visit. The Clinical Measures of Severity results for each item will be summarized at each designated visit for each eye with the number and percentage of subjects being classified as responders on each individual criterion.

Primary Efficacy Endpoint:

The primary outcome measure is the proptosis responder rate (percentage of subjects with a≥2 mm reduction from Baseline in proptosis in the study eye, without deterioration [≥2 mm increase] of proptosis in the fellow eye) at Week 24.

Secondary Efficacy Endpoints: Secondary Efficacy Endpoints Included:

- the percentage of subjects with a CAS value of 0 or 1 at Week 24;
- the mean changes from Baseline to Week 24 in proptosis the study eye;
- the diplopia responder rate (percentage of subjects with baseline diplopia≥0 in study eye who have a reduction of ≥1 grade with no corresponding deterioration [≥1 grade worsening] in the fellow eye) at Week 24; and
- the mean change from Baseline to Week 24 in the GO-QoL questionnaire overall score.

Exploratory Efficacy Endpoints:

- The overall responder rate (percentage of subjects with ≥2-point reduction in CAS AND≥2 mm reduction in proptosis from Baseline, provided there is no corresponding deterioration [≥2 point/mm increase] in CAS or proptosis in the fellow eye) at Week 24.
- The Clinical Measures of Severity individual response status frequencies and percentage of responders for each component of clinical severity at Week 24.
- The mean change from Baseline to Week 24 in the CAS (CAS will be measured as a continuous variable and will be summarized at each designated visit).
- The overall responder rate at Week 24 stratified by the level of response (high responders, responders, low responders, and non-responders.
- The mean change from Baseline to Week 24 in the GO-QOL questionnaire VF and A subscale scores.
- The mean change from Baseline to Week 24 on the motility component of the Clinical Measures of Severity.
- Evaluate pharmacokinetic (PK) parameters of teprotumumab to estimate exposure and understand PK-PD relationships.

Stratification of Proptosis and CAS Response into Four Responses Categories

To further explore the response based on both proptosis and CAS reduction, each subject is classified into one of 4 response categories at Week 24:

- High responders: Subjects who have a reduction in both proptosis and CAS of 3 or more (>3) from Baseline in the study eye, and no deterioration in the fellow eye (i.e., increase in CAS≥2 points or increase in proptosis>2 mm).
- Responders: Subjects who have a reduction in both CAS and proptosis of 2 or more (but less than 3) from Baseline in the study eye, and no deterioration in the fellow eye.
- Low Responders: Subjects who have a reduction in both CAS and proptosis of 1 or more (but less than 2) from Baseline in the study eye, and no deterioration in the fellow eye.
- Non-Responders: Subjects who do not fit into any of the above categories, or were not present for the Week 24 evaluation.

Pharmacokinetic Measurements

Blood samples are collected in 5 mL serum separator tube (SST) collection tubes to evaluate PK at the following time points: pre- and post-infusion on Day 1 and Weeks 3 and 9 of the Treatment Period; single samples will also be collected at Weeks 1, 4, and 24 (but not PW) of the Treatment Period. Samples are collected, processed, and stored at ≥−70° C. at the site until shipment to a laboratory, where they are stored at ≥−70° C. until PK testing.

Results.

It is expected that an antibody, or an antigen binding fragment thereof, that specifically binds to and/or inhibits insulin like growth factor-I receptor (IGF-IR), for example

- one having one or more CDRs chosen from SEQ ID NO.s 1-9,
- one having a heavy chain comprising CDR1, CDR2 and CDR3 and a light chain comprising CDR1, CDR2 and CDR3, from SEQ ID NO.s 1-9,
- one having heavy chain CDR1, CDR2, and CDR3 amino acid sequences and light chain CDR1, CDR2, and CDR3 amino acid sequences are at least 90% identical to (i) the amino acid sequences of SEQ ID NOs: 1-6, respectively; or (ii) the amino acid sequences of SEQ ID NOs: 1, 9, 3, 4, 10, 6,
- one having a heavy chain variable region having at least 80% sequence identity to the amino acid sequence of SEQ ID NO: 7 and a light chain variable region having at least 80% sequence identity to the amino acid sequence of SEQ ID NO: 8,
- one having a heavy chain variable region having at least 80% sequence identity to the amino acid sequence of SEQ ID NO: 11 and a light chain variable region having at least 80% sequence identity to the amino acid sequence of SEQ ID NO: 12,
- one having a heavy chain variable region comprising the amino acid sequence of SEQ ID NO: 7 and a light chain variable region comprising the amino acid sequence of SEQ ID NO: 8,
- one having a heavy chain variable region comprising the amino acid sequence of SEQ ID NO: 11 and a light chain variable region comprising the amino acid sequence of SEQ ID NO: 12,
- antibody 1, or an antigen binding fragment thereof,
- or antibody 2, or an antigen binding fragment thereof, or
- teprotumumab.

will, when administered to a subject with thyroid eye disease (TED) who has previously undergone prior treatment (for TED) with such an antibody, or an antigen binding fragment thereof, and either did not respond to said prior treatment or responded to said prior treatment and later relapsed, effectively:

- treat or reduce the severity of thyroid eye disease (TED) or a symptom thereof;
- reduce proptosis (e.g., by ≥2, 3, 4, or more mm);
- reduce CAS (e.g., by ≥2, 3, 4, or 5 points);
- not be accompanied by a proptosis deterioration of 2 mm or more in the other (or fellow eye);
- improve the subject's quality of life as measured by the GO-QOL, or either of its Functioning or Appearance subscales; and/or
- treat or reduce diplopia or the severity of diplopia.

SEQUENCES

TABLE 20

Sequences and SEQ ID Numbers

| SEQ ID NO | Description | Sequence |
|---|---|---|
| | Antibody 1 (teprotumumab) | |
| 1 | CDRH1 aa | Ser Tyr Gly Met His |
| 2 | CDRH2 aa | Ile Ile Trp Phe Asp Gly Ser Ser Thr Tyr Tyr Ala Asp Ser Val Arg Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |
| 5 | CDRL2 aa | Asp Ala Ser Lys Arg Ala Thr |
| 6 | CDRL3 aa | Gln Gln Arg Ser Lys Trp Pro Pro Trp Thr |
| 7 | VH aa | Gln Val Glu Leu Val Glu Ser Gly Gly Gly Val Val Gln Pro Gly Arg Ser Gln Arg Leu Ser Cys Ala Ala Ser Gly Phe Thr Phe Ser Ser Tyr Gly Met His Trp Val Arg Gln Ala Pro Gly Lys Gly Leu Glu Trp Val Ala Ile Ile Trp Phe Asp Gly Ser Ser Thr Tyr Tyr Ala Asp Ser Val Arg Gly Arg Phe Thr Ile Ser Arg Asp Asn Ser Lys Asn Thr Leu Tyr Leu Gln Met Asn Ser Leu Arg Ala Glu Asp Thr Ala Val Tyr Phe Cys Ala Arg Glu Leu Gly Arg Arg Tyr Phe Asp Leu Trp Gly Arg Gly Thr Leu Val Ser Val Ser Ser |
| 8 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Lys Arg Ala Thr Gly Ile Pro Ala Arg Phe Ser Gly Ser Gly Ser Gly Thr Asp Phe Thr Leu Thr Be Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ser Lys |
| | Antibody 2 | |
| 1 | CDRH1 aa | Ser Tyr Gly Met His |
| 9 | CDRH2 aa | Ile Ile Trp Phe Asp Gly Ser Ser Lys Tyr Tyr Gly Asp Ser Val Lys Gly |
| 3 | CDRH3 aa | Glu Leu Gly Arg Arg Tyr Phe Asp Leu |
| 4 | CDRL1 aa | Arg Ala Ser Gln Ser Val Ser Ser Tyr Leu Ala |
| 10 | CDRL2 aa | Asp Ala Ser Asn Arg Ala Thr |
| 6 | CDRL3 aa | Gln Gln Arg Ser Lys Trp Pro Pro Trp Thr |
| 11 | VH aa | Gln Val Gln Leu Val Glu Ser Gly Gly Gly Val Val Gln Pro Gly Arg Ser Leu Arg Leu Ser Cys Ala Ala Ser Gly Phe Thr Phe Ser Ser Tyr Gly Met His Trp Val Arg Gln Ala Pro Gly Lys Gly Leu Glu Trp Met Ala Ile Ile Trp Phe Asp Gly Ser Ser Lys Tyr Tyr Gly Asp Ser Val Lys Gly Arg Phe Thr Ile Ser Arg Asp Asn Ser Lys Asn Thr Leu Tyr Leu Gln Met Asn Ser Leu Arg Ala Asp Asp Thr Ala Val Tyr Tyr Cys Ala Arg Glu Leu Gly Arg Arg Tyr Phe Asp Leu Trp Gly Arg Gly Thr Leu Val Thr Val Ser Ser |
| 12 | VL aa | Glu Ile Val Leu Thr Gln Ser Pro Ala Thr Leu Ser Leu Ser Pro Gly Glu Arg Ala Thr Leu Ser Cys Arg Ala Ser Gln Ser Val Ser Ser Tyr Leu Ala Trp Tyr Gln Gln Lys Pro Gly Gln Ala Pro Arg Leu Leu Ile Tyr Asp Ala Ser Asn Arg Ala Thr Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Lys Trp Pro Pro Trp Thr Phe Gly Gln Gly Thr Lys Val Glu Ile Lys |

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A pharmaceutical composition, comprising:

an antibody comprising a heavy chain comprising a CDRH1 as set forth in SEQ ID NO: 1, a CDRH2 as set forth in SEQ ID NO: 9, and a CDRH3 as set forth in SEQ ID NO: 3, and a light chain comprising a CDRL1 as set forth in SEQ ID NO: 4, a CDRL2 as set forth in SEQ ID NO: 10, and a CDRL3 as set forth in SEQ ID NO: 6, wherein said antibody specifically binds to and inhibits insulin like growth factor-I receptor (IGF-1R); and a pharmaceutically acceptable excipient, wherein the pharmaceutical composition is configured to be intravenously administered to a subject at a dose of about 10 mg/kg or about 20 mg/kg.

2. The pharmaceutical composition of claim 1, wherein the antibody comprises a heavy chain variable region having at least 80% sequence identity to the amino acid sequence of SEQ ID NO: 11.

3. The pharmaceutical composition of claim 2, wherein the antibody comprises a heavy chain variable region comprising the sequence of SEQ ID NO: 11.

4. The pharmaceutical composition of claim 1, wherein the antibody comprises a light chain variable region having at least 80% sequence identity to the amino acid sequence of SEQ ID NO: 12.

5. The pharmaceutical composition of claim 4, wherein the antibody comprises a light chain variable region comprising the sequence of SEQ ID NO: 12.

6. The pharmaceutical composition of claim 1, wherein the pharmaceutical composition is configured to be intravenously administered to a subject at a dose of 10 mg/kg.

7. The pharmaceutical composition of claim 1, wherein the pharmaceutical composition is configured to be intravenously administered to a subject at a dose of 20 mg/kg.

8. The pharmaceutical composition of claim 1, wherein the antibody comprises a heavy chain variable region comprising the sequence of SEQ ID NO: 11 and a light chain variable region comprising the sequence of SEQ ID NO: 12.

9. The pharmaceutical composition of claim 8, wherein the antibody is a human antibody.

10. The pharmaceutical composition of claim 9, wherein the antibody is a human monoclonal antibody.

11. The pharmaceutical composition of claim 10, wherein the antibody is an IgG antibody.

12. The pharmaceutical composition of claim 11, wherein the antibody is an IgG1 antibody.

13. The pharmaceutical composition of claim 1, further comprising histidine-histidine chloride, trehalose, and polysorbate 20.

14. The pharmaceutical composition of claim 13, wherein the composition is lyophilized.

15. The pharmaceutical composition of claim 1, wherein the composition is lyophilized.

* * * * *

SEQUENCE LISTING

```
Sequence total quantity: 12
SEQ ID NO: 1           moltype = AA  length = 5
FEATURE                Location/Qualifiers
source                 1..5
                       mol_type = protein
                       organism = Homo sapiens
SEQUENCE: 1
SYGMH                                                              5

SEQ ID NO: 2           moltype = AA  length = 17
FEATURE                Location/Qualifiers
source                 1..17
                       mol_type = protein
                       organism = Homo sapiens
SEQUENCE: 2
IIWFDGSSTY YADSVRG                                                 17

SEQ ID NO: 3           moltype = AA  length = 9
FEATURE                Location/Qualifiers
source                 1..9
                       mol_type = protein
                       organism = Homo sapiens
SEQUENCE: 3
ELGRRYFDL                                                          9

SEQ ID NO: 4           moltype = AA  length = 11
FEATURE                Location/Qualifiers
source                 1..11
                       mol_type = protein
                       organism = Homo sapiens
SEQUENCE: 4
RASQSVSSYL A                                                       11

SEQ ID NO: 5           moltype = AA  length = 7
FEATURE                Location/Qualifiers
source                 1..7
                       mol_type = protein
                       organism = Homo sapiens
SEQUENCE: 5
DASKRAT                                                            7

SEQ ID NO: 6           moltype = AA  length = 10
FEATURE                Location/Qualifiers
source                 1..10
                       mol_type = protein
                       organism = Homo sapiens
SEQUENCE: 6
QQRSKWPPWT                                                         10

SEQ ID NO: 7           moltype = AA  length = 118
FEATURE                Location/Qualifiers
source                 1..118
                       mol_type = protein
                       organism = Homo sapiens
SEQUENCE: 7
QVELVESGGG VVQPGRSQRL SCAASGFTFS SYGMHWVRQA PGKGLEWVAI IWFDGSSTYY  60
ADSVRGRFTI SRDNSKNTLY LQMNSLRAED TAVYFCAREL GRRYFDLWGR GTLVSVSS    118

SEQ ID NO: 8           moltype = AA  length = 108
FEATURE                Location/Qualifiers
source                 1..108
                       mol_type = protein
                       organism = Homo sapiens
SEQUENCE: 8
EIVLTQSPAT LSLSPGERAT LSCRASQSVS SYLAWYQQKP GQAPRLLIYD ASKRATGIPA  60
RFSGSGSGTD FTLTISSLEP EDFAVYYCQQ RSKWPPWTFG QGTKVESK               108
```

-continued

```
SEQ ID NO: 9            moltype = AA  length = 17
FEATURE                 Location/Qualifiers
source                  1..17
                        mol_type = protein
                        organism = Homo sapiens
SEQUENCE: 9
IIWFDGSSKY YGDSVKG                                                17

SEQ ID NO: 10           moltype = AA  length = 7
FEATURE                 Location/Qualifiers
source                  1..7
                        mol_type = protein
                        organism = Homo sapiens
SEQUENCE: 10
DASNRAT                                                           7

SEQ ID NO: 11           moltype = AA  length = 118
FEATURE                 Location/Qualifiers
source                  1..118
                        mol_type = protein
                        organism = Homo sapiens
SEQUENCE: 11
QVQLVESGGG VVQPGRSLRL SCAASGFTFS SYGMHWVRQA PGKGLEWMAI IWFDGSSKYY  60
GDSVKGRFTI SRDNSKNTLY LQMNSLRADD TAVYYCAREL GRRYFDLWGR GTLVTVSS    118

SEQ ID NO: 12           moltype = AA  length = 108
FEATURE                 Location/Qualifiers
source                  1..108
                        mol_type = protein
                        organism = Homo sapiens
SEQUENCE: 12
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSKWPPWTFG QGTKVEIK              108
```